United States Patent
Ko

(10) Patent No.: US 11,891,621 B2
(45) Date of Patent: Feb. 6, 2024

(54) METHOD FOR DIFFERENTIATING PLURIPOTENT STEM CELLS INTO DESIRED CELL TYPE

(71) Applicant: KEIO UNIVERSITY, Tokyo (JP)

(72) Inventor: Minoru Ko, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 498 days.

(21) Appl. No.: 17/065,541

(22) Filed: Oct. 8, 2020

(65) Prior Publication Data

US 2021/0024887 A1 Jan. 28, 2021

Related U.S. Application Data

(62) Division of application No. 15/555,559, filed as application No. PCT/JP2016/057420 on Mar. 9, 2016, now Pat. No. 10,836,997.

(30) Foreign Application Priority Data

Mar. 9, 2015 (JP) .................................. 2015-046318

(51) Int. Cl.
| | |
|---|---|
| *C12N 5/00* | (2006.01) |
| *C12N 5/0793* | (2010.01) |
| *C12N 5/071* | (2010.01) |
| *C12N 5/0735* | (2010.01) |
| *C12N 5/0797* | (2010.01) |
| *C12N 5/07* | (2010.01) |

(52) U.S. Cl.
CPC ............ *C12N 5/0619* (2013.01); *C12N 5/06* (2013.01); *C12N 5/0606* (2013.01); *C12N 5/067* (2013.01); *C12N 5/0623* (2013.01); *C12N 5/0672* (2013.01); *C12N 2501/60* (2013.01); *C12N 2501/65* (2013.01); *C12N 2506/02* (2013.01); *C12N 2506/45* (2013.01); *C12N 2510/00* (2013.01)

(58) Field of Classification Search
None
See application file for complete search history.

(56) References Cited

U.S. PATENT DOCUMENTS

| 8,497,124 B2 | 7/2013 | Angel et al. |
| 2002/0090603 A1 | 7/2002 | Lipton et al. |
| 2011/0280844 A1 | 11/2011 | Yu et al. |
| 2016/0046905 A1 | 2/2016 | Inoue et al. |
| 2018/0127714 A1 | 5/2018 | Ko |

FOREIGN PATENT DOCUMENTS

| EP | 2495320 A1 * | 10/2010 | ............ C12N 5/067 |
| JP | 2004-016109 A | 1/2004 | |
| JP | 2013-252081 A | 12/2013 | |
| WO | 2013025963 A2 | 2/2013 | |

OTHER PUBLICATIONS

International Search Report and Written Opinion (English Translation) issued in corresponding International Patent Application No. PCT/JP2016/057420 dated Jun. 7, 2016 (14 pages).
Berg et al., "Beta-Catenin Regulates Mesenchymal Progenitor Cell Differentiation During Hepatogenesis," Journal of Surgical Research, 2010, vol. 164, pp. 276-285.
Kim et al., "Overexpression of SOX9 in mouse embryonic stem cells directs the immediate chondrogenic commitment," Experimental and Molecular Medicine, 2005, vol. 37, No. 4, pp. 261-268.
Kim et al., "OVOL2 is a critical regulator of ER71/ETV2 in generating FLK1+, hematopoietic, and endothelial cells from embryonic stem cells," Blood, 2014, vol. 124, No. 19, pp. 2948-2952.
Nakatake et al., "Hito Es-saibo ni Okeru Tensa Inshi Yudo no Morateki Kaiseki," Regenerative Medicine, 2015, vol. 14, Suppl., p. 231 (English translation) (1 page).
Yamamizu et al., "Tensha Inshi o Mochiita Tanosei Kansaibo kara Nin'i Saibo eno Bunka Yudoho no Kaihatsu," Experimental Medicine, 2015, vol. 33, No. 2 (special extra issue), pp. 87-94 (English translation ) (1 page).

* cited by examiner

*Primary Examiner* — Marcia S Noble
(74) *Attorney, Agent, or Firm* — Kilyk & Bowersox, P.L.L.C.

(57) ABSTRACT

Provided is a method of differentiating a pluripotent stem cell of mammalian origin into a desired cell type by predicting the direction of cell differentiation to be caused by induction of expression of a transcription factor. A human gene expression correlation matrix using human cells has been newly created, and further, it has been confirmed that human pluripotent stem cells can be differentiated into a desired cell type by introducing, into the human pluripotent stem cells, a transcription factor cocktail selected from the matrix.

7 Claims, 21 Drawing Sheets

Specification includes a Sequence Listing.

Fig. 4A

| TFs | Fetal_brain | TFs | Pituitary | TFs | Cerebellum_Peduncles | TFs | Cerebellum |
|---|---|---|---|---|---|---|---|
| SOX11 | 21.723 | SOX17 | 14.881 | NEUROG2 | 19.986 | NEUROG2 | 19.964 |
| NEUROG2 | 19.583 | SOX2 | 14.85 | NEUROG3 | 17.822 | NEUROG3 | 17.869 |
| MXI1 | 17.840 | SOX7 | 11.823 | TAL1 | 14.751 | TAL1 | 16.187 |
| NEUROG1 | 16.646 | CDX2 | 11.432 | NEUROG1 | 14.58 | BLZF1 | 15.251 |
| NEUROG3 | 16.373 | ASCL1 | 11.288 | BLZF1 | 14.02 | NEUROG1 | 15.188 |
| SOX7 | 15.856 | SOX15 | 11.128 | NEUROD1 | 12.891 | NEUROD1 | 13.451 |
| HOXA2 | 12.893 | NANOG | 10.975 | ZNF280B | 12.245 | NRF1 | 12.821 |
| POU3F2 | 11.370 | HOXA2 | 10.987 | NRF1 | 11.273 | MXI1 | 12.372 |
| NEUROD2 | 11.578 | NR2F2 | 10.029 | HOXA2 | 11.285 | ZNF280B | 12.098 |
| RARA | 11.498 | HOXA1 | 9.965 | ASCL1 | 10.878 | HOXA2 | 12.02 |
| FOXI1 | 11.395 | DLX4 | 9.546 | NEUROD6 | 10.821 | FOXD1 | 11.797 |
| PLI1 | 10.828 | SOX18 | 9.287 | MXI1 | 10.818 | PITX2 | 11.578 |
| FOXS1 | 10.818 | FOXA2 | 9.153 | FOXD1 | 10.739 | NEUROD6 | 11.397 |
| MEIS2 | 10.57 | EED | 8.968 | KLF15 | 10.21 | ASCL1 | 11.378 |
| SOX17 | 10.521 | E2F6 | 8.978 | PITX2 | 9.343 | SNAPC1 | 11.213 |
| HDAC3 | 10.503 | POX1 | 9.934 | NEUROD2 | 9.802 | NEUROD2 | 10.785 |
| NEUROD1 | 10.415 | PKNOX3 | 8.842 | SNAPC1 | 9.51 | KLF15 | 10.078 |
| EED | 10.284 | DLX3 | 8.78 | YBX1 | 9.083 | NFIB | 10.80 |
| NR2F1 | 10.242 | HOXD3 | 8.644 | PROM1 | 9.04 | YBX1 | 10.018 |
| NEUROD6 | 10.217 | FOXS1 | 7.848 | SMAD7 | 9.016 | CREB1 | 9.988 |
| LHX1 | 10.171 | ZBED4 | 7.851 | ATOH1 | 8.885 | PROM1 | 9.881 |
| GLIS2 | 10.04 | NR2F1 | 7.566 | SOX7 | 8.439 | ATOH1 | 9.865 |
| YBX1 | 8.891 | SOX11 | 7.492 | MAB21L3 | 8.393 | MAX | 8.862 |
| HOXA3 | 8.843 | POU2F2 | 7.401 | POU4F1 | 8.341 | TCF4 | 8.818 |
| PKGXF2 | 8.752 | MYOD1 | 7.397 | TCF4 | 8.17 | SMAD7 | 8.829 |
| ZBED4 | 8.478 | NEUROG1 | 7.192 | CREB1 | 8.123 | TCF12 | 8.816 |
| SOX2 | 8.121 | DLX2 | 7.088 | MAX | 8.115 | ERG | 8.725 |
| ETV5 | 8.047 | FOXC1 | 6.675 | FOXS1 | 8.195 | GLIS2 | 8.536 |
| POU4F1 | 8.74 | TCF12 | 6.645 | SOX11 | 7.845 | SOX11 | 8.497 |
| HOXD3 | 8.671 | RARA | 6.318 | TCF12 | 7.801 | UGP2 | 8.388 |

Fig. 4B

| TFs | Whole_Brain | TFs | Brain_Thalamus | TFs | Hypothalamus | TFs | Prefrontal_Cortex |
|---|---|---|---|---|---|---|---|
| NEUROG2 | 18.951 | NEUROG2 | 13.928 | SOX7 | 14.169 | NEUROG2 | 18.806 |
| NEUROG3 | 14.357 | HOXA2 | 11.582 | NEUROG2 | 13.727 | NEUROG3 | 15.867 |
| NEUROG1 | 13.249 | NEUROG3 | 11.269 | SOX17 | 13.71 | MXI1 | 15.838 |
| NRF1 | 13.235 | NEUROG1 | 10.96 | SOX2 | 12.873 | SOX7 | 15.827 |
| MXI1 | 11.998 | SOX7 | 10.798 | HOXA2 | 12.571 | YBX1 | 15.382 |
| ZNF280B | 10.978 | GLIS2 | 10.374 | SOX18 | 12.317 | NEUROG1 | 15.103 |
| HOXA2 | 10.708 | SOX37 | 10.221 | NEUROG1 | 11.888 | SOX37 | 14.149 |
| PITX2 | 10.339 | NRF1 | 10.178 | GLIS2 | 10.84 | HOXA2 | 14.087 |
| KLF15 | 10.23 | KLF15 | 9.7 | NEUROG3 | 10.81 | SOX11 | 13.448 |
| NEUROD1 | 9.774 | ASCL1 | 8.428 | MXI1 | 9.807 | SOX2 | 12.44 |
| ASCL1 | 9.127 | SOX18 | 8.402 | SOX11 | 9.405 | ASCL1 | 11.753 |
| GLIS2 | 8.878 | POU4F1 | 8.381 | ASCL1 | 9.298 | SOX18 | 11.703 |
| POU4F1 | 8.881 | FOXD1 | 7.983 | SOX8 | 9.089 | PDX1 | 11.480 |
| SOX7 | 8.715 | MXI1 | 7.898 | PDX1 | 8.762 | POU4F1 | 10.866 |
| NFIB | 8.551 | SOX2 | 7.862 | NRF1 | 8.574 | NRF1 | 10.262 |
| FOXD1 | 8.544 | PITX2 | 7.628 | SOX15 | 8.155 | GLIS2 | 10.066 |
| BLZF1 | 8.078 | SREBF2 | 7.403 | NR2F1 | 7.988 | HOXD3 | 10.05 |
| POU2AF1 | 8.061 | RNF2 | 7.172 | E2F6 | 7.98 | NEUROD2 | 9.681 |
| TAL1 | 8.02 | PPARGC1A | 6.942 | NANOG | 7.822 | KLF15 | 9.898 |
| ZNF281 | 7.982 | TCF12 | 6.888 | CDX2 | 7.804 | TAL1 | 9.804 |
| PPARGC1A | 7.813 | E2F6 | 6.757 | POU4F1 | 7.772 | FOXS1 | 9.434 |
| NEUROD6 | 7.795 | REPIN1 | 6.710 | FOXS1 | 7.884 | CREB1 | 9.310 |
| HOXD3 | 7.674 | SOX11 | 6.679 | HOXD3 | 7.551 | CDX2 | 9.093 |
| CREB1 | 7.509 | NEUROD6 | 6.530 | RARA | 7.462 | NEUROD2 | 9.08 |
| EGR1AM | 7.44 | YY1 | 6.390 | TCF12 | 7.42 | PROM1 | 8.477 |
| MAX | 7.431 | FOXI1 | 6.373 | SREBF2 | 7.416 | BLZF1 | 8.655 |
| SNAPC1 | 7.383 | NEUROD1 | 6.14 | NR2F2 | 6.846 | NANOG | 8.426 |
| TCF4 | 7.318 | NFIB | 6.121 | POU3F1 | 6.804 | NFIB | 8.337 |
| VDR | 7.239 | ZNF281 | 6.108 | HOXA3 | 6.581 | PITX2 | 8.248 |

Fig. 4C

| TFs | Occipital_Lobe | TFs | Brain_Amygdala | TFs | Cauda_tenuicus | TFs | Cingulate_Cortex |
|---|---|---|---|---|---|---|---|
| NEUROG2 | 18.185 | NEUROG2 | 18.398 | NEUROG2 | 14.487 | NEUROG2 | 18.932 |
| NEUROG1 | 15.454 | NEUROG1 | 15.287 | HOXA2 | 13.472 | NEUROG1 | 16.428 |
| HOXA2 | 15.034 | SOX7 | 15.048 | SOX7 | 12.298 | NEUROG1 | 15.039 |
| SOX7 | 14.856 | NEUROG3 | 14.895 | NEUROG3 | 11.731 | HOXA2 | 14.039 |
| NEUROG3 | 14.598 | HOXA2 | 14.872 | SOX17 | 11.872 | SOX7 | 12.772 |
| MXI1 | 14.202 | MXI1 | 14.287 | NRF1 | 11.683 | NRF1 | 12.326 |
| SOX17 | 14.098 | SOX17 | 14.147 | NEUROG1 | 11.843 | YBX1 | 12.011 |
| SOX2 | 12.204 | SOX2 | 13.431 | MXI1 | 11.43 | TAL1 | 11.815 |
| SOX11 | 11.831 | SOX18 | 12.081 | SOX2 | 11.13 | ASCL1 | 11.727 |
| PDX1 | 11.488 | PDX1 | 11.861 | GLIS2 | 10.877 | MXI1 | 11.564 |
| SOX18 | 11.351 | GLIS2 | 11.645 | SOX18 | 10.45 | SOX17 | 11.4 |
| GLIS2 | 10.348 | NRF1 | 11.424 | ASCL1 | 9.88 | KLF15 | 10.802 |
| POU4F1 | 10.098 | SOX11 | 10.938 | TCF12 | 9.286 | GLIS2 | 10.44 |
| HOXD3 | 9.38 | ASCL1 | 10.394 | RARA | 9.28 | NEUROD1 | 10.474 |
| YBX1 | 9.369 | HOXD3 | 10.122 | PDX1 | 9.253 | POU4F1 | 10.286 |
| ASCL1 | 8.904 | NEUROD1 | 9.545 | FOXD1 | 9.117 | SOX11 | 10.232 |
| NRF1 | 9.729 | NR2F1 | 9.434 | KLF15 | 8.792 | PDX1 | 9.977 |
| NEUROD1 | 9.541 | CDX2 | 9.38 | SOX11 | 8.518 | PRDM1 | 9.714 |
| POU3F2 | 9.184 | CREB1 | 9.232 | POU4F1 | 8.39 | FOXD1 | 9.43 |
| NR2F1 | 9.039 | NEUROD6 | 8.991 | FOXS1 | 8.148 | BLZF1 | 9.315 |
| CDX2 | 8.88 | E2F6 | 8.928 | E2F6 | 8.052 | NEUROD6 | 9.284 |
| NEUROD6 | 8.817 | POU4F1 | 8.847 | TAL1 | 8.05 | TCF12 | 9.079 |
| EED | 8.737 | MAX | 8.47 | PITX2 | 7.97 | ERG | 8.983 |
| NR2F2 | 8.534 | HOXB3 | 8.275 | MAX | 7.952 | RARA | 8.9 |
| HOXB3 | 8.37 | NANOG | 8.135 | FOXA1 | 7.813 | PITX2 | 8.858 |
| E2F6 | 8.31 | TCF12 | 8.091 | CREB1 | 7.501 | HOXD3 | 8.852 |
| FOXS1 | 8.285 | FOXS1 | 8.090 | HOXD3 | 7.5 | ETV5 | 8.468 |
| ETV5 | 8.218 | EED | 7.987 | BLZF1 | 7.824 | CREB1 | 8.239 |
| SOX15 | 8.217 | POU3F2 | 7.861 | NEUROD6 | 7.759 | RNF2 | 8.15 |
| FLI1 | 8.078 | NFIC | 7.863 | NFIB | 7.47 | SOX2 | 7.964 |

Fig. 4D

| TFs | Medulla_Oblongata | TFs | Globus_pallidus | TFs | Subthalamic_nucleus | TFs | Parietal_Lobe |
|---|---|---|---|---|---|---|---|
| NEUROG2 | 17.512 | NEUROG2 | 16.435 | NEUROG2 | 17.195 | NEUROG2 | 17.286 |
| HOXA2 | 15.884 | HOXA2 | 14.41 | HOXA2 | 15.168 | HOXA2 | 15.028 |
| SOX17 | 14.716 | NEUROG1 | 13.983 | NEUROG1 | 13.982 | NEUROG3 | 14.204 |
| SOX7 | 14.731 | NEUROG3 | 13.684 | NEUROG3 | 13.873 | NEUROG1 | 14.147 |
| NEUROG3 | 14.422 | NRF1 | 12.793 | NRF1 | 11.944 | SOX7 | 13.888 |
| NEUROG1 | 14.373 | SOX7 | 11.311 | SOX7 | 11.911 | SOX17 | 12.925 |
| NRF1 | 12.561 | MXI1 | 11.312 | MXI1 | 11.469 | MXI1 | 12.468 |
| MXI1 | 11.642 | SOX17 | 11.273 | SOX17 | 11.336 | NRF1 | 12.327 |
| GLIS2 | 11.705 | YBX1 | 10.378 | YBX1 | 11.148 | YBX1 | 12.112 |
| PDX1 | 11.673 | GLIS2 | 9.853 | SOX11 | 10.818 | GLIS2 | 11.121 |
| SOX11 | 11.424 | ASCL1 | 9.801 | ASCL1 | 10.288 | SOX11 | 10.016 |
| SOX2 | 11.225 | PDX1 | 9.572 | PDX1 | 9.724 | ASCL1 | 10.540 |
| ASCL1 | 10.608 | POU4F1 | 9.508 | POU4F1 | 9.848 | SOX2 | 9.886 |
| YBX1 | 10.508 | ETV5 | 9.358 | GLIS2 | 9.585 | PDX1 | 9.78 |
| SOX18 | 10.503 | SOX11 | 9.319 | TCF12 | 9.503 | SOX18 | 9.383 |
| CREB1 | 10.468 | CREB1 | 9.222 | RARA | 9.359 | ETV5 | 9.303 |
| NR2F1 | 9.752 | RARA | 9.196 | FOXD1 | 9.062 | CREB1 | 9.289 |
| HOXD3 | 9.460 | TAL1 | 4.777 | NEUROD1 | 9.017 | POU4F1 | 9.099 |
| NEUROD6 | 9.201 | SOX2 | 8.884 | ETV5 | 8.907 | RARA | 8.937 |
| FLI1 | 9.187 | FLI1 | 8.552 | CREB1 | 8.769 | NEUROD6 | 8.869 |
| NR2F2 | 9.08 | TCF12 | 8.428 | NEUROD6 | 8.6 | TCF12 | 8.312 |
| POU4F1 | 8.952 | NEUROD6 | 8.229 | E2F6 | 8.286 | TAL1 | 8.058 |
| RARA | 8.814 | ERG | 8.208 | TAL1 | 8.204 | HOXD3 | 8.029 |
| ETV5 | 8.731 | E2F6 | 8.17 | FOXS1 | 8.182 | E2F6 | 7.964 |
| CDX2 | 8.613 | FOXD1 | 8.053 | SOX2 | 8.088 | NEUROD1 | 7.903 |
| NEUROD1 | 8.550 | NEUROD1 | 7.893 | FLI1 | 7.880 | FOXS1 | 7.909 |
| SOX15 | 8.348 | REPIN1 | 7.881 | NR2F1 | 7.724 | FLI1 | 7.852 |
| E2F6 | 8.334 | RNF2 | 7.832 | ZBED4 | 7.752 | KLF15 | 7.846 |
| TCF12 | 8.281 | ZBED4 | 7.53 | HOXD3 | 7.516 | FOXD1 | 7.71 |
| NFIC | 8.032 | BLZF1 | 7.568 | KLF15 | 7.48 | BLZF1 | 7.686 |

Fig. 4E

| TFs | Temporal_Lobe | TFs | Pons | TFs | Olfactory_Bulb | TFs | Spinal_cord |
|---|---|---|---|---|---|---|---|
| NEUROG2 | 15.894 | HOXA2 | 16.458 | SOX9 | 19.528 | SOX18 | 16.162 |
| NRF1 | 14.733 | NRF1 | 15.134 | SOX18 | 17.216 | SOX9 | 14.953 |
| HOXA2 | 13.938 | NEUROG2 | 15.007 | NFIB | 16.085 | SOX17 | 13.833 |
| NEUROG3 | 13.001 | CREB1 | 12.773 | TBX2 | 14.018 | GLIS2 | 12.51 |
| NEUROG1 | 12.9 | GLIS2 | 12.7 | SOX17 | 13.542 | SOX2 | 11.859 |
| SOX7 | 10.287 | NEUROG1 | 12.442 | GLIS2 | 12.924 | SOX7 | 11.695 |
| GLIS2 | 9.735 | SOX17 | 12.352 | SOX2 | 12.081 | HOXA2 | 11.516 |
| CREB1 | 9.418 | NEUROG3 | 11.928 | HES1 | 11.757 | NFIB | 11.522 |
| MXI1 | 9.288 | SOX7 | 11.511 | JUNB | 11.525 | KLF15 | 10.193 |
| SOX17 | 9.183 | ERG | 10.474 | ARNT2 | 11.495 | ARNT2 | 9.18 |
| PBX3 | 9.056 | PARA | 10.184 | NFIC | 11.479 | TBX3 | 8.983 |
| SOX11 | 9.042 | FOX1 | 10.077 | TBX3 | 11.448 | TBX2 | 8.781 |
| FOXO3 | 8.841 | CTCF | 10.024 | KLF15 | 11.016 | TCF12 | 8.586 |
| REPIN1 | 8.741 | SOX11 | 9.782 | FOS | 10.715 | NR2F1 | 8.28 |
| RNF2 | 8.391 | TAL1 | 9.852 | FEV | 10.186 | NEUROG2 | 8.088 |
| NEUROD1 | 8.372 | FOXD1 | 9.637 | NR2F1 | 10.032 | MAX | 8.031 |
| PITX2 | 8.343 | MXI1 | 9.579 | TP73 | 10.008 | FOXA1 | 7.898 |
| NEUROG6 | 8.271 | TCF12 | 9.39 | FOXA2 | 9.180 | SREBF2 | 7.863 |
| ASCL1 | 8.266 | HES1 | 9.274 | SOX7 | 9.804 | E2F6 | 7.631 |
| KLF15 | 8.068 | YBX1 | 9.230 | CTCF | 9.864 | FEV | 7.611 |
| TAL1 | 8.010 | ASCL1 | 8.996 | HEY1 | 9.86 | HES1 | 7.58 |
| POU4F1 | 7.937 | ELI1 | 8.994 | TFAP2B | 9.852 | MXI1 | 7.578 |
| SNAPC3 | 7.71 | NR2F1 | 8.921 | GATA3 | 9.587 | NRF1 | 7.492 |
| RARA | 7.621 | MAX | 8.71 | IRF4 | 9.547 | RARA | 7.418 |
| PPARGC1A | 7.541 | REPIN1 | 8.693 | HNF1A | 9.428 | FOXC1 | 7.431 |
| TCF12 | 7.501 | SNAPC1 | 8.69 | FOXS1 | 9.337 | FOXA2 | 7.328 |
| ZNF281 | 7.402 | SOX2 | 8.872 | FOXA1 | 9.18 | FOXS1 | 7.297 |
| HOXA3 | 7.256 | NR2F2 | 8.686 | HOXA2 | 9.105 | LHX3 | 7.194 |
| SOX2 | 7.273 | KLF15 | 8.544 | POU1 | 8.815 | SOX18 | 7.873 |
| HOXD3 | 7.147 | PNF2 | 8.529 | NANOG | 8.985 | NEUROG1 | 7.833 |

Fig. 4F

| TFs | Heart | TFs | Skeletal_Muscle_Psoas | TFs | Tongue | TFs | Skin |
|---|---|---|---|---|---|---|---|
| TGIF1 | 25.533 | MYOG1 | 16.304 | MYOG1 | 14.122 | HES1 | 14.291 |
| ZNF2808 | 22.358 | NRF1 | 12.85 | TP73 | 13.982 | HEY1 | 13.685 |
| SALL4 | 21.804 | PPARGC1A | 12.221 | JUNB | 11.817 | TP73 | 13.266 |
| SOX14 | 21.464 | TAL1 | 11.918 | HES1 | 11.695 | JUNB | 12.97 |
| ESRRAM | 21.139 | SALL4 | 11.743 | KLF4 | 10.949 | CTCF | 10.866 |
| PITX2 | 20.408 | CREB1 | 11.636 | FOS | 10.683 | CREB1 | 12.037 |
| TAL1 | 19.841 | REPIN1 | 9.573 | SALL4 | 10.208 | GLIS2 | 11.921 |
| ZNF281 | 19.018 | CTCF | 9.448 | HESL1 | 9.898 | TFAP2C | 10.897 |
| AFIDJA | 18.613 | HOXA2 | 9.41 | FOSL2 | 9.731 | HOXA2 | 10.292 |
| PPARGC1A | 18.471 | ERG | 9.326 | NRF1 | 9.682 | NRF1 | 10.434 |
| CTCFL | 18.397 | ZNF281 | 9.174 | HEY1 | 9.461 | TBX5 | 10.431 |
| NKX2-1 | 17.703 | TP73 | 9.088 | TFAP2C | 9.285 | FOS | 9.985 |
| FTAFE | 17.306 | CTCF | 8.778 | ZNF281 | 9.086 | GRHL2 | 9.528 |
| KLF15 | 17.113 | HES1 | 8.522 | GRHL2 | 8.931 | NFIC | 9.279 |
| TFE1 | 16.714 | KLF1 | 8.486 | YBX5 | 8.69 | ESX1 | 9.254 |
| NFIB | 16.552 | BLZF1 | 8.145 | ESX1 | 8.651 | ELF1 | 9.023 |
| TP73 | 16.436 | FOXP1 | 7.977 | PPARGC1A | 8.615 | ERG | 9.018 |
| TCF4 | 16.135 | SOX14 | 7.919 | FOXP1 | 8.556 | CEBPA | 8.817 |
| FOS | 15.856 | YBX1 | 7.731 | GLIS2 | 8.542 | GATA2 | 8.779 |
| TBX5 | 15.697 | PRDM1 | 7.718 | NFIB | 7.89 | THAP11 | 8.698 |
| FOXP1 | 15.178 | TLX1 | 7.572 | HOXA2 | 8.177 | THAP7 | 8.604 |
| MAB21L3 | 14.686 | PTAFR | 7.493 | REPIN1 | 8.384 | FOXP1 | 8.541 |
| NRF1 | 14.218 | TCF3 | 7.478 | FEV | 8.099 | IRF5 | 8.515 |
| ELK1 | 13.873 | KLF3 | 7.31 | PTAFR | 7.988 | ZIC1 | 8.476 |
| ESX1 | 13.803 | PITX2 | 7.397 | ZIC1 | 7.941 | GATA3 | 8.307 |
| POU2AF1 | 13.361 | HEY1 | 7.184 | CREB1 | 7.784 | MEIS2 | 8.28 |
| FOSL2 | 13.255 | YY1 | 6.948 | TFE1 | 7.571 | PBXOT3 | 8.222 |
| MSX2 | 13.218 | NFIB | 6.038 | ELF1 | 7.402 | TBX2 | 8.141 |
| VDR | 13.083 | ZIC1 | 6.933 | GATA3 | 7.297 | FOSL1 | 8.1 |
| HOXA3 | 12.912 | PAX4 | 6.862 | ESRRB | 7.198 | FEV | 8.028 |

Fig. 4G

| TFs | Dorsal_root_ganglion | TFs | Appendix | TFs | Superior_Cervical_Ganglion | TFs | Atrioventricular_node |
|---|---|---|---|---|---|---|---|
| HES1 | 17.817 | HES1 | 16.988 | HES1 | 17.35 | HES1 | 16.167 |
| GLIS2 | 17.284 | HEY1 | 16.409 | YBX1 | 14.977 | HEY1 | 14.29 |
| HOXA2 | 16.038 | CTCF | 16.178 | HEY1 | 14.392 | HOXA2 | 14.817 |
| HEY1 | 14.199 | HOXA2 | 15.884 | CREB1 | 14.778 | CTCF | 13.879 |
| TBX2 | 13.919 | GLIS2 | 15.428 | CTCF | 14.453 | NRF1 | 13.827 |
| CTCF | 13.783 | SOX17 | 15.385 | HOXA2 | 14.313 | CREB1 | 13.334 |
| NRF1 | 13.565 | TBX2 | 13.96 | NRF1 | 14.172 | THAP7 | 11.758 |
| SOX17 | 12.698 | CREB1 | 13.521 | FLI1 | 12.884 | GLIS2 | 11.644 |
| REPIN1 | 11.946 | THAP7 | 13.237 | GLIS2 | 12.722 | ERG | 11.365 |
| NR2F1 | 11.528 | NR2F2 | 13.16 | ERG | 12.425 | NFIC | 11.019 |
| NR2F2 | 11.235 | NRF1 | 12.884 | TBX2 | 11.288 | TBX2 | 10.881 |
| RARA | 11.207 | JUNB | 12.898 | NFIC | 10.822 | TBX5 | 10.881 |
| JUNB | 11.078 | NFIC | 12.467 | TBX5 | 10.75 | SOX17 | 10.663 |
| TBX5 | 11.024 | TBX5 | 12.442 | TAL1 | 10.385 | TAL1 | 10.096 |
| ERG | 10.951 | ERG | 12.298 | NR2F2 | 10.393 | TP73 | 10.074 |
| CREB1 | 10.8 | TBX2 | 11.252 | MEIS2 | 10.573 | JUNB | 9.981 |
| TBX5 | 10.456 | FLI1 | 10.6 | SOX17 | 10.359 | YBX1 | 9.857 |
| NFIC | 10.397 | FBXO15 | 10.482 | GATA2 | 10.083 | FBXO15 | 9.77 |
| E2F8 | 10.315 | PDX1 | 10.459 | ETV5 | 9.972 | REPIN1 | 9.664 |
| TCF12 | 10.282 | NR4A2 | 10.261 | PDX1 | 9.941 | GATA2 | 9.346 |
| FEV | 9.872 | ARNT2 | 10.235 | REPIN1 | 9.843 | NR2F2 | 9.225 |
| THAP7 | 9.842 | NR2F1 | 10.195 | FBXO15 | 9.497 | THAP11 | 9.097 |
| FOS | 9.835 | ELF1 | 9.933 | JUNB | 9.423 | FLI1 | 9.036 |
| SOX2 | 9.375 | SOX15 | 9.773 | MKRN1 | 9.216 | TCF12 | 8.705 |
| NFIB | 9.303 | SOX2 | 9.753 | THAP7 | 8.372 | RARA | 8.559 |
| SREBF2 | 9.175 | GATA2 | 9.521 | SOX11 | 9.188 | NFIB | 8.471 |
| FOXI1 | 9.098 | REPIN1 | 9.498 | NR2F1 | 8.591 | TFAP2C | 8.413 |
| TAL1 | 8.983 | IRF1 | 9.367 | RNF2 | 9.09 | MKRN1 | 8.365 |
| ARNT2 | 8.78 | MEIS2 | 9.377 | TCF12 | 9.028 | TCEA3 | 8.371 |
| SOX10 | 8.548 | EGR3 | 9.363 | RARA | 9.028 | NR2F1 | 8.303 |

Fig. 4H

| TFs | Trigeminal_Ganglion | TFs | Ciliary_ganglion | TFs | Uterus_Corpus | TFs | Ovary |
|---|---|---|---|---|---|---|---|
| HES1 | 17.93 | HES1 | 21.195 | HES1 | 16.483 | HEY1 | 12.888 |
| HEY1 | 15.928 | GLIS2 | 18.412 | JUNB | 13.577 | HES1 | 12.724 |
| HOXA2 | 15.427 | NRF1 | 16.889 | FOS | 14.035 | TBX2 | 9.914 |
| NRF1 | 15.083 | CTCF | 16.983 | GLIS2 | 13.61 | CTCF | 9.839 |
| GLIS2 | 13.852 | HEY1 | 16.348 | HEY1 | 13.39 | TBX5 | 9.806 |
| CTCF | 13.766 | CREB1 | 15.98 | CTCF | 13.123 | THAP7 | 9.693 |
| CREB1 | 13.350 | HOXA2 | 15.801 | FOSL1 | 12.185 | GLIS2 | 9.687 |
| ERG | 11.741 | JUNB | 13.769 | ARNT2 | 11.635 | HOXA2 | 9.697 |
| JUNB | 11.403 | NFIC | 14.936 | THAP7 | 11.835 | JUNB | 8.725 |
| TBX2 | 11.451 | ARNT2 | 13.354 | CREB1 | 11.391 | FBXO15 | 8.514 |
| NR2F2 | 10.734 | TBX2 | 13.309 | JUN | 10.98 | NR2F2 | 8.398 |
| REPIN1 | 10.684 | ERG | 13.259 | ERG | 10.868 | CREB1 | 8.344 |
| TBX5 | 10.521 | NFIB | 13.898 | NRF1 | 10.864 | SOX17 | 8.332 |
| NFIC | 10.446 | FEV | 12.464 | NFIB | 10.867 | NR2F2 | 8.281 |
| SOX17 | 10.114 | FOS | 12.463 | TBX5 | 10.642 | NR4A2 | 8.225 |
| RARA | 10.106 | TCF12 | 12.13 | HOXA2 | 10.923 | NFIC | 7.753 |
| THAP7 | 10.041 | TBX5 | 11.972 | ZNF281 | 10.506 | ERG | 7.975 |
| TBX2 | 9.892 | SOX17 | 11.973 | THAP11 | 10.482 | TBX5 | 7.875 |
| TAL1 | 9.852 | REPIN1 | 11.825 | TBX2 | 10.469 | NRF1 | 7.851 |
| TCF12 | 9.106 | THAP7 | 11.596 | TBX5 | 10.173 | ARNT2 | 7.372 |
| NR2F1 | 8.868 | NR2F2 | 11.523 | ELF5 | 10.047 | CEBPD | 7.292 |
| TP73 | 8.812 | ZNF281 | 11.398 | NFIC | 9.28 | CEBPA | 7.252 |
| FLI1 | 8.817 | NR2F1 | 11.32 | TFAP2C | 9.868 | BHLHE40 | 6.993 |
| FBXO15 | 8.717 | TP73 | 10.708 | TP73 | 9.956 | ELF5 | 6.905 |
| ARNT2 | 8.674 | TBX5 | 10.473 | EGR2 | 8.828 | TFAP4 | 6.811 |
| FEV | 8.608 | FOSL1 | 10.361 | ZIC1 | 9.713 | ELF1 | 6.774 |
| ZNF281 | 8.636 | FOXP1 | 10.111 | MEIS1 | 9.303 | MSC | 6.719 |
| E2F8 | 8.587 | FBXO15 | 10.097 | ELF1 | 9.302 | PTAFR | 6.476 |
| ELF1 | 8.574 | TFAP2C | 9.976 | ESX1 | 9.28 | ZNF281 | 6.46 |
| YBX1 | 8.57 | IRF4 | 9.857 | PTAFR | 9.082 | GATA3 | 6.428 |

Fig. 4I

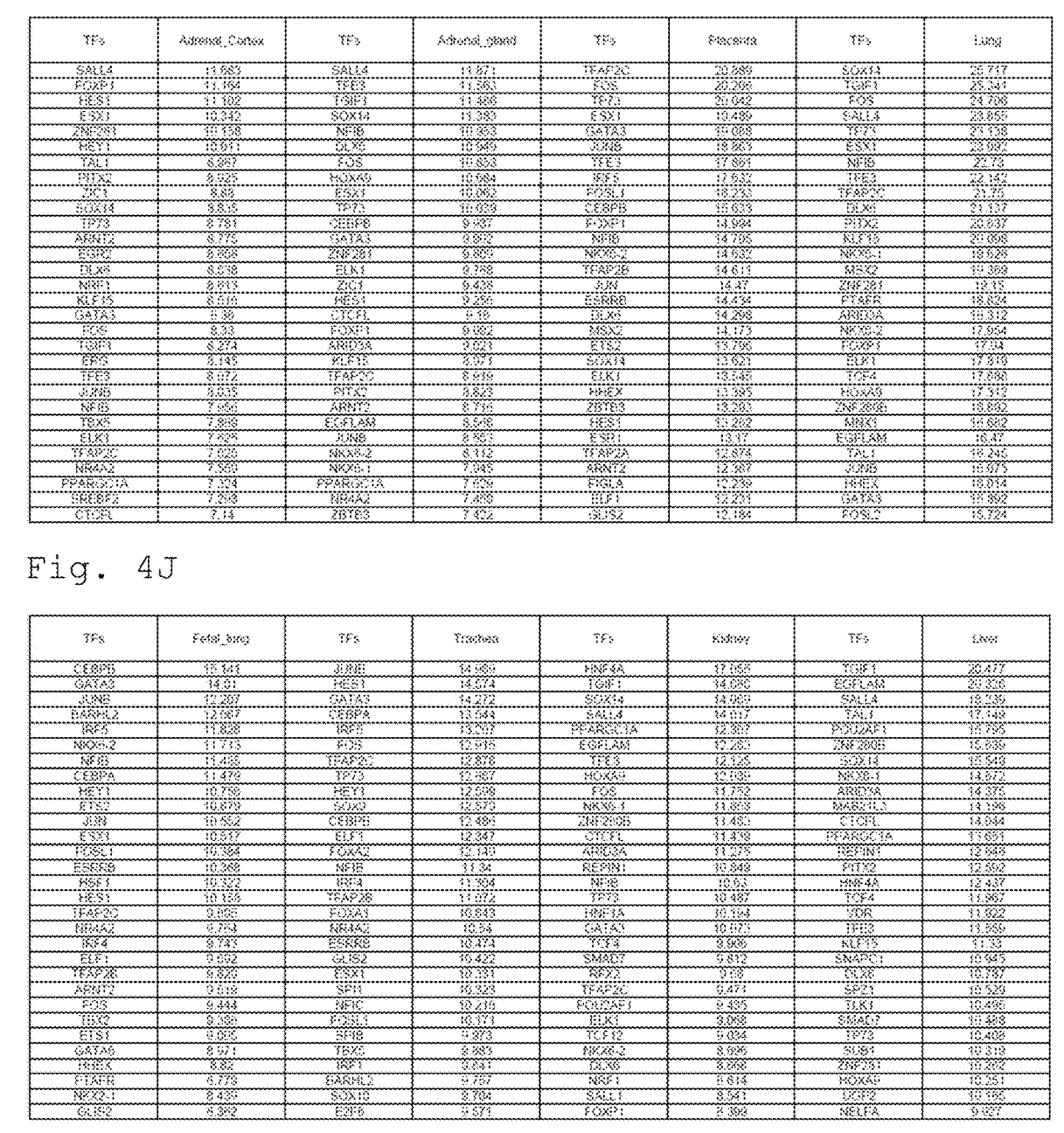

| TFs | Adrenal_Cortex | TFs | Adrenal_gland | TFs | Placenta | TFs | Lung |
|---|---|---|---|---|---|---|---|
| SALL4 | 11.683 | SALL4 | 11.871 | TFAP2C | 20.889 | SOX14 | 25.717 |
| FOXP1 | 11.164 | TFE3 | 11.563 | FOS | 20.208 | TGIF1 | 25.341 |
| HES1 | 11.102 | TGIF1 | 11.488 | TP73 | 20.042 | FOS | 24.708 |
| ESX1 | 10.342 | SOX14 | 11.389 | ESX1 | 19.489 | SALL4 | 23.855 |
| ZNF281 | 10.158 | NFIB | 10.893 | GATA3 | 19.008 | TP73 | 23.138 |
| HEY1 | 10.611 | DLX6 | 10.949 | JUNB | 18.863 | ESX1 | 23.092 |
| TAL1 | 8.987 | FOS | 10.893 | TFE3 | 17.891 | NFIB | 22.73 |
| PITX2 | 8.925 | HOXA9 | 10.584 | IRF5 | 17.632 | TFE3 | 22.142 |
| ZIC1 | 8.88 | ESX1 | 10.062 | FOSL1 | 16.233 | TFAP2C | 21.75 |
| SOX14 | 8.835 | TP73 | 10.039 | CEBPB | 15.633 | DLX6 | 21.137 |
| TP73 | 8.781 | CEBPB | 9.937 | FOXP1 | 14.924 | PITX2 | 20.637 |
| ARNT2 | 8.775 | GATA3 | 9.932 | NFIB | 14.705 | KLF15 | 20.098 |
| EGR2 | 8.658 | ZNF281 | 9.809 | NKX6-2 | 14.632 | NKX6-1 | 19.626 |
| DLX6 | 8.638 | ELK1 | 9.768 | TFAP2B | 14.611 | MSX2 | 19.389 |
| NRF1 | 8.613 | ZIC1 | 9.438 | JUN | 14.47 | ZNF281 | 19.15 |
| KLF15 | 8.516 | HES1 | 9.256 | ESRRB | 14.434 | PTAFR | 18.824 |
| GATA3 | 8.39 | CTCFL | 9.19 | DLX6 | 14.298 | ARID3A | 18.312 |
| FOS | 8.33 | FOXP1 | 9.082 | MSX2 | 14.173 | NKX6-2 | 17.954 |
| TGIF1 | 8.274 | ARID3A | 9.023 | ETS2 | 13.798 | FOXP1 | 17.94 |
| ERG | 8.145 | KLF15 | 8.971 | SOX14 | 13.621 | ELK1 | 17.918 |
| TFE3 | 8.072 | TFAP2C | 8.939 | ELK1 | 13.545 | TCF4 | 17.888 |
| JUNB | 8.035 | PITX2 | 8.823 | HHEX | 13.385 | HOXA9 | 17.312 |
| NFIB | 7.956 | ARNT2 | 8.716 | ZBTB3 | 13.283 | ZNF280B | 16.892 |
| TBX5 | 7.889 | EGFLAM | 8.548 | HES1 | 13.262 | MNX1 | 16.682 |
| ELK3 | 7.825 | JUNB | 8.553 | ESR1 | 13.17 | EGFLAM | 16.47 |
| TFAP2C | 7.620 | NKX6-2 | 8.112 | TFAP2A | 12.874 | TAL1 | 16.245 |
| NR4A2 | 7.559 | NKX6-1 | 7.945 | ARNT2 | 12.387 | JUNB | 16.075 |
| PPARGC1A | 7.324 | PPARGC1A | 7.629 | FIGLA | 12.239 | HHEX | 16.014 |
| SREBF2 | 7.283 | NR4A2 | 7.489 | ELF1 | 12.231 | GATA3 | 15.892 |
| CTCFL | 7.14 | ZBTB3 | 7.432 | GLIS2 | 12.184 | FOSL2 | 15.724 |

Fig. 4J

| TFs | Fetal_lung | TFs | Trachea | TFs | Kidney | TFs | Liver |
|---|---|---|---|---|---|---|---|
| CEBPB | 15.141 | JUNB | 14.989 | HNF4A | 17.058 | TGIF1 | 20.477 |
| GATA3 | 14.01 | HES1 | 14.574 | TGIF1 | 14.080 | EGFLAM | 20.326 |
| JUNB | 12.207 | GATA3 | 14.272 | SOX14 | 14.069 | SALL4 | 18.239 |
| BARHL2 | 12.087 | CEBPA | 13.544 | SALL4 | 14.017 | TAL1 | 17.149 |
| IRF5 | 11.828 | IRF5 | 13.097 | PPARGC1A | 12.307 | POU2AF1 | 15.795 |
| NKX6-2 | 11.733 | FOS | 12.915 | EGFLAM | 12.263 | ZNF280B | 15.639 |
| NFIB | 11.488 | TFAP2C | 12.878 | TFE3 | 12.125 | SOX14 | 15.548 |
| CEBPA | 11.478 | TP73 | 12.867 | HOXA9 | 12.039 | NKX6-1 | 14.672 |
| HEY1 | 10.759 | HEY1 | 12.599 | FOS | 11.752 | ARID3A | 14.375 |
| ETS2 | 10.679 | SOX9 | 12.579 | NKX6-1 | 11.603 | MAB21L3 | 14.196 |
| JUN | 10.552 | CEBPB | 12.486 | ZNF280B | 11.463 | CTCFL | 14.044 |
| ESX1 | 10.517 | ELF1 | 12.347 | CTCFL | 11.439 | PPARGC1A | 13.651 |
| FOSL1 | 10.384 | FOXA2 | 12.140 | ARID3A | 11.275 | REPIN1 | 12.646 |
| ESRRB | 10.369 | NFIB | 11.34 | REPIN1 | 10.849 | PITX2 | 12.592 |
| HSF1 | 10.322 | IRF4 | 11.304 | NFIB | 10.63 | HNF4A | 12.437 |
| HES1 | 10.156 | TFAP2B | 11.072 | TP73 | 10.487 | TCF4 | 11.967 |
| TFAP2C | 9.885 | FOXA1 | 10.843 | HNF1A | 10.194 | VDR | 11.622 |
| NR4A2 | 9.793 | NR4A2 | 10.54 | GATA3 | 10.073 | TFE3 | 11.359 |
| IRF4 | 9.743 | ESRRB | 10.474 | TCF4 | 9.905 | KLF15 | 11.33 |
| ELF1 | 9.692 | GLIS2 | 10.422 | SMAD7 | 9.812 | SNAPC1 | 10.945 |
| TFAP2B | 9.620 | ESX1 | 10.331 | RFX2 | 9.68 | DLX6 | 10.787 |
| ARNT2 | 9.518 | SPI1 | 10.323 | TFAP2C | 9.471 | SPZ1 | 10.529 |
| FOS | 9.444 | NFIC | 10.216 | POU2AF1 | 9.435 | ELK1 | 10.495 |
| TBX2 | 9.385 | FOSL1 | 10.171 | ELK1 | 9.068 | SMAD7 | 10.488 |
| ETS1 | 9.005 | SPIB | 9.873 | TCF12 | 9.034 | TP73 | 10.408 |
| GATA6 | 8.971 | TBX3 | 9.883 | NKX6-2 | 8.995 | SUB1 | 10.319 |
| HHEX | 8.82 | IRF1 | 9.841 | DLX6 | 8.868 | ZNF281 | 10.292 |
| PTAFR | 8.779 | BARHL2 | 9.757 | NRF1 | 8.614 | HOXA9 | 10.251 |
| NKX2-1 | 8.439 | SOX10 | 9.704 | SALL1 | 8.541 | UGP2 | 10.195 |
| GLIS2 | 8.382 | E2F6 | 9.571 | FOXP1 | 8.392 | NELFA | 9.927 |

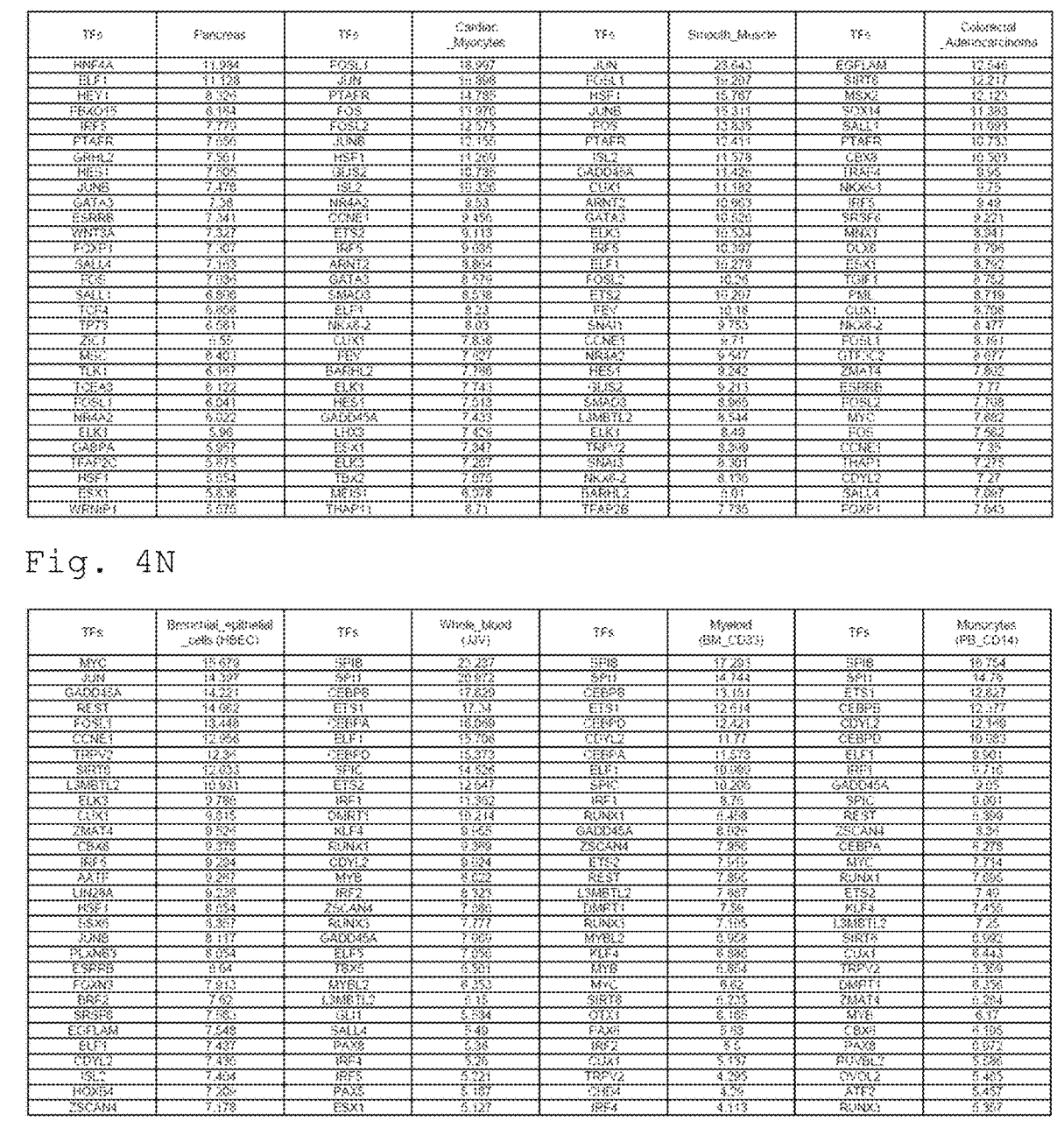

[Table with columns: TFs, Pancreas, TFs, Cardiac_Myocytes, TFs, Smooth_Muscle, TFs, Colorectal Adenocarcinoma — content illegible]

Fig. 4N

[Table with columns: TFs, Bronchial_epithelial_cells (HBEC), TFs, Whole_blood (AW), TFs, Myeloid (BM_CD33), TFs, Monocytes (PB_CD14) — content illegible]

| TFs | Leukemia_promyelocytic(hl60) | TFs | Leukemia_lymphoblastic(molt4) | TFs | Testis | TFs | Testis_Leydig_Cell |
|---|---|---|---|---|---|---|---|
| SSX6 | 24.121 | SSX6 | 20.643 | POU2AF1 | 11.302 | MYBL2 | 12.629 |
| MYC | 23.554 | REST | 20.205 | RFX2 | 10.914 | EED | 5.98 |
| SIRT6 | 21.801 | ZNF426 | 18.284 | TGIF1 | 10.18 | TCEA3 | 5.802 |
| REST | 21.449 | SIRT6 | 17.33 | EGFLAM | 10.058 | MYB | 5.538 |
| ZNF426 | 19.947 | GTF2F1 | 16.318 | CTCFL | 9.133 | E2F1 | 5.473 |
| ZFAND3 | 19.201 | RSPO1 | 15.87 | SALL4 | 8.046 | E2F4 | 5.424 |
| RSPO1 | 19.114 | SSX4B | 15.652 | MYBL2 | 8.481 | NR2F2 | 5.305 |
| Cebpb | 18.907 | NR3C1 | 15.598 | DLX6 | 7.543 | ZFAND1 | 5.258 |
| ZBTB45 | 18.728 | ATF2 | 15.083 | HOXA9 | 7.348 | SNAI3 | 5.248 |
| ATF2 | 18.686 | Cebpb | 14.686 | RFX5 | 7.242 | STRA8 | 5.058 |
| HDAC2 | 18.305 | E2F4 | 14.164 | SMAD7 | 7.198 | GTF2F1 | 4.947 |
| PML | 17.775 | ZBTB45 | 14.005 | MYB | 7.185 | STAG1 | 4.946 |
| LIN28A | 17.671 | HOPX | 13.926 | SOX14 | 6.758 | CRY2 | 4.923 |
| SSX4B | 17.581 | HDAC2 | 13.887 | MSX2 | 6.736 | WHSC1 | 4.896 |
| NR3C1 | 17.437 | VPS72 | 13.838 | MAB21L3 | 6.728 | SETDB1 | 4.838 |
| GTF2F1 | 16.34 | JARID2 | 13.641 | SALL1 | 6.685 | NFYB | 4.81 |
| AATF | 16.238 | RUVBL2 | 13.6 | ZNF280B | 6.507 | ZBED4 | 4.584 |
| RFXAP | 15.625 | DEDD2 | 13.578 | SMARCB1 | 6.234 | KDM5A | 4.540 |
| DEDD2 | 15.585 | ID1 | 13.557 | THAP1 | 5.936 | TP53 | 4.387 |
| VAX1 | 15.433 | AATF | 13.528 | ESX1 | 5.898 | SNAI1 | 4.375 |
| BRF2 | 15.43 | VAX1 | 13.381 | RUVBL2 | 5.873 | SIX5 | 4.375 |
| VPS72 | 15.303 | LMO1 | 13.275 | GTF3C2 | 5.707 | SAP30 | 4.378 |
| ID1 | 15.225 | MYC | 13.029 | FOXM1 | 5.686 | RFXAP | 4.124 |
| SRSF8 | 15.042 | RFXAP | 12.696 | ARID3A | 5.518 | RHOXF2 | 4.03 |
| SUZ12 | 15.011 | SMARCB1 | 12.445 | PITX2 | 5.369 | EGR1 | 4.025 |
| ZFP57 | 14.988 | PML | 12.373 | YY1 | 5.331 | SOX13 | 3.977 |
| LMO1 | 14.821 | CDYL2 | 12.385 | ATOH1 | 5.319 | REST | 3.958 |
| PLXNB3 | 14.797 | XRCC4 | 12.286 | NKX6-1 | 5.241 | YBX1 | 3.942 |
| JARID2 | 14.794 | ZBTB33 | 12.281 | BACH1 | 4.954 | MSGN1 | 3.896 |
| XRCC4 | 14.589 | ZFAND3 | 12.264 | ID3 | 4.731 | XRCC4 | 3.838 |

Fig. 4T

| TFs | Testis_Germ_Cell | TFs | Testis_Seminiferous_Tubule | TFs | Testis_Interstitial |
|---|---|---|---|---|---|
| MYBL2 | 13.174 | MYBL2 | 12.781 | MYBL2 | 13.584 |
| SNAI1 | 8.782 | E2F4 | 6.871 | E2F4 | 8.09 |
| SNAI3 | 8.674 | SNAI1 | 6.282 | WHSC1 | 7.796 |
| EED | 7.871 | SNAI3 | 6.18 | EED | 7.606 |
| REST | 6.27 | MYB | 6.169 | SNAI3 | 7.08 |
| WHSC1 | 6.203 | GTF2F1 | 5.738 | GTF2F1 | 6.446 |
| MYB | 6.159 | E2F1 | 5.68 | REST | 6.425 |
| L3MBTL2 | 5.598 | REST | 5.61 | MYB | 6.019 |
| STRA8 | 4.916 | WHSC1 | 5.458 | ZFAND3 | 5.962 |
| KDM5A | 4.815 | STRA8 | 5.108 | SNAI1 | 5.944 |
| E2F4 | 4.797 | YBX1 | 4.429 | NR2F2 | 5.792 |
| NR2F2 | 4.757 | ZFAND3 | 4.420 | E2F1 | 5.686 |
| MSGN1 | 4.646 | STAG1 | 4.393 | STRA8 | 5.633 |
| LHX4 | 4.446 | SSX4B | 4.388 | CRY2 | 5.328 |
| MXI1 | 4.409 | NFYB | 4.313 | SSX6 | 5.226 |
| EGR1 | 4.280 | RFXAP | 4.171 | STAG1 | 4.951 |
| ZBED4 | 4.011 | SSX6 | 4.080 | ZBED4 | 4.837 |
| WNT3A | 4.008 | YY1 | 3.983 | RFXAP | 4.585 |
| GATA6 | 3.989 | MSGN1 | 3.883 | SETDB1 | 4.55 |
| TCEA3 | 3.779 | SRSF8 | 3.812 | KDM5A | 4.523 |
| SETDB1 | 3.722 | MSI1 | 3.808 | RXRA | 4.433 |
| CDX2 | 3.718 | CRY2 | 3.801 | ZNF263 | 4.335 |
| PTF1A | 3.679 | HOPX | 3.727 | TCEA3 | 4.289 |
| CRY2 | 3.548 | ZBED4 | 3.723 | HOPX | 4.2 |
| PHOX2B | 3.545 | NEUROD1 | 3.72 | SIX5 | 4.181 |
| FOXS1 | 3.511 | HIST2H3C | 3.798 | SOX15 | 4.098 |
| HOPX | 3.49 | EED | 3.613 | XRCC4 | 4.024 |
| STAG1 | 3.441 | ZFP57 | 3.598 | RHOXF2 | 3.975 |
| SOX11 | 3.399 | SMARCA4 | 3.543 | TP53 | 3.917 |
| SSX6 | 3.373 | ZSCAN4 | 3.481 | HIST2H3C | 3.743 |

METHOD FOR DIFFERENTIATING PLURIPOTENT STEM CELLS INTO DESIRED CELL TYPE

The present invention relates to a method of differentiating a pluripotent stem cell into a desired cell type and a differentiation inducer to be used for the differentiation method.

The present application is a divisional of U.S. patent application Ser. No. 15/555,559, filed Dec. 27, 2017, which is a National Stage Application of PCT/JP2016/057420, filed Mar. 9, 2016, which claims priority from Japanese Patent Application No. 2015-046318, filed Mar. 9, 2015, which is incorporated herein by reference.

TECHNICAL FIELD

Background Art (Network of Transcription Factors)

A network of transcription factors (TF) can be modified by determining cell identity information and overexpressing a plurality of transcription factors in combination. It is difficult to select a combination of transcription factors that causes specific cell differentiation and prove that the combination causes the differentiation because possible combinations of transcription factors are as many as about 2,000 kinds.

One of the purposes of regenerative medicine is to generate differentiated cells of a desired type from pluripotent stem cells, such as embryonic stem (ES) cells and induced pluripotent stem (iPS) cells {Non Patent Literature 1: Nature 292, 154-156 (1981), Non Patent Literature 2: Proc Natl Acad Sci USA 78, 7634-7638 (1981), Non Patent Literature 3: Science 282, 1145-1147 (1998), Non Patent Literature 4: Cell 126, 663-676 (2006)}.

However, a great number and variety of complicated regulatory mechanisms of transcription factors pose a huge problem on a search for a right combination of transcription factors.

With a view to facilitating transcription factor network analysis, a systems biology approach has been applied {Non Patent Literature 9: Annu Rev Cell Dev Biol 26, 721-744 (2010)} to loss of function, i.e., knockout or suppression of a transcription factor of mouse ES cells {Non Patent Literature 5: Nat Genet 36, 543-544 (2004), Non Patent Literature 6: Nature 442, 533-538 (2006), Non Patent Literature 7: Cell 128, 9-13 (2007), Non Patent Literature 8: Sci Rep 3, 1390 (2013)}, followed by phenotypic analysis or extensive transcriptome analysis.

However, gain of function, i.e., an approach involving overexpression of a transcription factor is more preferred because modification of cell identity information has been able to be considerably achieved as described above by forcible induction of a combination of transcription factors {Non Patent Literature 10: Cell 51, 987-1000 (1987), Non Patent Literature 4: Cell 126, 663-676 (2006), Non Patent Literature 11: Proc Natl Acad Sci USA 105, 6057-6062 (2008), Non Patent Literature 12: Nature 468, 521-526 (2010), Non Patent Literature 13: Nature 463, 1035-1041 (2010), Non Patent Literature 14: Nature 476, 224-227 (2011), Non Patent Literature 15: Cell Stem Cell 9, 205-218 (2011), Non Patent Literature 16: Nature 475, 390-393 (2011), Non Patent Literature 17: Nature 475, 386-389 (2011)}. Therefore, the NIA Mouse ES Cell Bank {Non Patent Literature 18: Cell Stem Cell 5, 420-433 (2009), Non Patent Literature 19: Sci Rep 1, 167 (2011)} has been established. In the NIA Mouse ES Cell Bank, 137 kinds of transcription factors, i.e., 7% to 10% of all transcription factors encoded in a mouse genome (1,500 to 2,000 kinds of transcription factors) {Non Patent Literature 20: Biochem Biophys Res Commun 322, 787-793 (2004)} can each be induced by a method capable of tetracycline regulation. After 48 hours from forcibly induced expression of each transcription factor, an extensive gene expression profile (i.e., transcriptome) was measured in each of those ES cell lines {Non Patent Literature 19: Sci Rep 1, 167 (2011)}. Meanwhile, profiles of expression amounts of all genes expressed in various cell species, tissues, and organs are available as public domain databases. One of such databases includes expression profiles of a variety of cell types, provided by the Genomics Institute of the Novartis Research Foundation (GNF) {Non Patent Literature 21: Genome Biol 10, R130 (2009), Non Patent Literature 22: Proc Natl Acad Sci USA 99, 4465-4470 (2002)}. Through comparison between the transcription factor-induced gene expression profiles obtained by the above-mentioned experimentation and the gene expression profiles of the GNF, a matrix for showing correlations of gene expression levels (gene expression correlation matrix) has been created.

(Differentiation of Cell)

It is considered that a differentiation state of a cell is dictated by a set of specific transcription factors expressed in the cell and their expression levels. The transcription factors are factors directly regulating gene expression, and play an important role in forming a cell-specific gene network by binding to transcription regulatory regions, such as promoters and enhancers, to promote or suppress a process of transcribing genetic information of DNA into RNA.

In recent years, research has been actively conducted into development of a technology for inducing differentiation into arbitrary cells using induced pluripotent stem cells (iPS cells). However, there have been problems of low differentiation efficiency and coexistence of different cell lineages. Accordingly, it is an extremely important task to identify transcription factors capable of governing determination of cell differentiation and terminal differentiation.

(Network of Mouse Transcription Factors)

In order to elucidate the structure of a mouse transcription factor network that determines cell differentiation lineages, the inventor of the present invention has established the NIA Mouse ES Cell Bank (cell lines corresponding to 137 transcription factor genes), which allows expression of mouse transcription factor genes to be freely induced {Non Patent Literature 18: Cell Stem Cell 5, 420-433 (2009), Non Patent Literature 19: Sci Rep 1, 167 (2011)}.

In each of those cell lines, a single transcription factor can be forcibly expressed quickly and strongly by removing doxycycline from a culture solution through use of a Tet-off system. The inventor of the present invention has used those cell lines to comprehensively analyze changes in transcript amounts 48 hours after gene expression induction with a microarray. A comparison of the resultant gene expression profile to a gene expression pattern of each mouse organ or tissue (gene expression correlation matrix) has allowed clear observation of what cell lineage tends to be dictated by a change in the gene expression pattern caused by induction of expression of a single transcription factor. With this, it has been confirmed that the direction of cell differentiation to be caused by induction of expression of a transcription factor can be predicted with considerable accuracy.

CITATION LIST

Non Patent Literature

[NPL 1] Nature 292, 154-156 (1981)
[NPL 2] Proc Natl Acad Sci USA 78, 7634-7638 (1981)
[NPL 3] Science 282, 1145-1147 (1998)
[NPL 4] Cell 126, 663-676 (2006)
[NPL 5] Nat Genet 36, 543-544 (2004)
[NPL 6] Nature 442, 533-538 (2006)
[NPL 7] Cell 128, 9-13 (2007)
[NPL 8] Sci Rep 3, 1390 (2013)
[NPL 9] Annu Rev Cell Dev Biol 26, 721-744 (2010)
[NPL 10] Cell 51, 987-1000 (1987)
[NPL 11] Proc Natl Acad Sci USA 105, 6057-6062 (2008)
[NPL 12] Nature 468, 521-526 (2010)
[NPL 13] Nature 463, 1035-1041 (2010)
[NPL 14] Nature 476, 224-227 (2011)
[NPL 15] Cell Stem Cell 9, 205-218 (2011)
[NPL 16] Nature 475, 390-393 (2011)
[NPL 17] Nature 475, 386-389 (2011)
[NPL 18] Cell Stem Cell 5, 420-433 (2009)
[NPL 19] Sci Rep 1, 167 (2011)
[NPL 20] Biochem Biophys Res Commun 322, 787-793 (2004)
[NPL 21] Genome Biol 10, R130 (2009)
[NPL 22] Proc Natl Acad Sci USA 99, 4465-4470 (2002)

SUMMARY OF INVENTION

Technical Problem

It has been confirmed that, through use of a gene expression correlation matrix created using mouse ES cells developed and created by the inventor of the present invention, the direction of cell differentiation to be caused by induction of expression of a transcription factor can be predicted with considerable accuracy. However, it is known that humans and mice, though both are mammals, are significantly different in some respects of cell differentiation.

Solution to Problem

The inventor of the present invention has newly created a human gene expression correlation matrix using human cells, and further, has confirmed that human pluripotent stem cells can be differentiated into a desired cell type by introducing a transcription factor cocktail selected from the matrix into the human pluripotent stem cells. Thus, the present invention has been accomplished.

That is, the present invention includes the following.

1. A method of differentiating a pluripotent stem cell into a neural cell, including a step of introducing a transcription factor including any one of the following (1) to (5) into a pluripotent stem cell of mammalian origin:
   (1) five transcription factors selected from NEUROG1, NEUROG2, NEUROG3, NEUROD1, and NEUROD2;
   (2) four transcription factors selected from NEUROG1, NEUROG2, NEUROG3, NEUROD1, and NEUROD2;
   (3) three transcription factors selected from NEUROG1, NEUROG2, NEUROG3, NEUROD1, and NEUROD2;
   (4) two transcription factors selected from NEUROG1, NEUROG2, NEUROG3, NEUROD1, and NEUROD2; and
   (5) one transcription factor selected from NEUROG1, NEUROG2, NEUROG3, NEUROD1, and NEUROD2.
2. A method of differentiating a pluripotent stem cell into a neural cell according to the above-mentioned item 1, in which the neural cell includes a motor nerve.
3. A method of differentiating a pluripotent stem cell into a neural cell according to the above-mentioned item 1 or 2, in which the motor nerve is a cell present in a motor nerve.
4. A neural cell differentiation inducer, which is capable of differentiating a pluripotent stem cell of mammalian origin into a neural cell, the neural cell differentiation inducer including a transcription factor including any one of the following (1) to (5):
   (1) five transcription factors selected from NEUROG1, NEUROG2, NEUROG3, NEUROD1, and NEUROD2;
   (2) four transcription factors selected from NEUROG1, NEUROG2, NEUROG3, NEUROD1, and NEUROD2;
   (3) three transcription factors selected from NEUROG1, NEUROG2, NEUROG3, NEUROD1, and NEUROD2;
   (4) two transcription factors selected from NEUROG1, NEUROG2, NEUROG3, NEUROD1, and NEUROD2; and
   (5) one transcription factor selected from NEUROG1, NEUROG2, NEUROG3, NEUROD1, and NEUROD2.
5. A differentiation inducer according to the above-mentioned item 4, in which the neural cell is a peripheral motor nerve.
6. A differentiation inducer according to the above-mentioned item 4 or 5, in which the motor nerve is a cell present in a motor nerve.
7. A differentiation inducer according to any one of the above-mentioned items 4 to 6, in which the transcription factor is mRNA, synthetic mRNA, a nucleic acid, or a protein.
8. A method of differentiating a pluripotent stem cell into a hepatoblast and/or a liver cell, including a step of introducing a transcription factor including any one of the following (1) to (5) into a pluripotent stem cell of mammalian origin:
   (1) one transcription factor selected from TGIF, TCF4, PITX2, SALL4, and MEIS1;
   (2) two transcription factors selected from TGIF, TCF4, PITX2, SALL4, and MEIS1;
   (3) three transcription factors selected from TGIF, TCF4, PITX2, SALL4, and MEIS1;
   (4) four transcription factors selected from TGIF, TCF4, PITX2, SALL4, and MEIS1; and
   (5) five transcription factors selected from TGIF, TCF4, PITX2, SALL4, and MEIS1.
9. A hepatoblast and/or liver cell differentiation inducer, which is capable of differentiating a pluripotent stem cell of mammalian origin into a hepatoblast and/or a liver cell, the hepatoblast and/or liver cell differentiation inducer including a transcription factor including any one of the following (1) to (5):
   (1) one transcription factor selected from TGIF, TCF4, PITX2, SALL4, and MEIS1;
   (2) two transcription factors selected from TGIF, TCF4, PITX2, SALL4, and MEIS1;
   (3) three transcription factors selected from TGIF, TCF4, PITX2, SALL4, and MEIS1;
   (4) four transcription factors selected from TGIF, TCF4, PITX2, SALL4, and MEIS1; and
   (5) five transcription factors selected from TGIF, TCF4, PITX2, SALL4, and MEIS1.
10. A method of differentiating a pluripotent stem cell into a hematopoietic stem cell and/or a blood cell, including a step of introducing a transcription factor including anyone of the following (1) to (7) into a pluripotent stem cell of mammalian origin:
(1) one transcription factor selected from CDYL2, ETS2, SPI1, OVOL2, CDX2, CEBPB, and SALL4;
(2) two transcription factors selected from CDYL2, ETS2, SPI1, OVOL2, CDX2, CEBPB, and SALL4;
(3) three transcription factors selected from CDYL2, ETS2, SPI1, OVOL2, CDX2, CEBPB, and SALL4;
(4) four transcription factors selected from CDYL2, ETS2, SPI1, OVOL2, CDX2, CEBPB, and SALL4;
(5) five transcription factors selected from CDYL2, ETS2, SPI1, OVOL2, CDX2, CEBPB, and SALL4;
(6) six transcription factors selected from CDYL2, ETS2, SPI1, OVOL2, CDX2, CEBPB, and SALL4; and
(7) seven transcription factors selected from CDYL2, ETS2, SPI1, OVOL2, CDX2, CEBPB, and SALL4.

11. A hematopoietic stem cell and/or blood cell differentiation inducer, which is capable of differentiating a pluripotent stem cell of mammalian origin into a hematopoietic stem cell and/or a blood cell, the hematopoietic stem cell and/or blood cell differentiation inducer including a transcription factor including any one of the following (1) to (7):
(1) one transcription factor selected from CDYL2, ETS2, SPI1, OVOL2, CDX2, CEBPB, and SALL4;
(2) two transcription factors selected from CDYL2, ETS2, SPI1, OVOL2, CDX2, CEBPB, and SALL4;
(3) three transcription factors selected from CDYL2, ETS2, SPI1, OVOL2, CDX2, CEBPB, and SALL4;
(4) four transcription factors selected from CDYL2, ETS2, SPI1, OVOL2, CDX2, CEBPB, and SALL4;
(5) five transcription factors selected from CDYL2, ETS2, SPI1, OVOL2, CDX2, CEBPB, and SALL4;
(6) six transcription factors selected from CDYL2, ETS2, SPI1, OVOL2, CDX2, CEBPB, and SALL4; and
(7) seven transcription factors selected from CDYL2, ETS2, SPI1, OVOL2, CDX2, CEBPB, and SALL4.

12. A method of differentiating a pluripotent stem cell into a chondrocyte, including a step of introducing a transcription factor SOX9 into a pluripotent stem cell of mammalian origin.

13. A chondrocyte differentiation inducer, which is capable of differentiating a pluripotent stem cell of mammalian origin into a chondrocyte, the chondrocyte differentiation inducer including a transcription factor SOX9.

14. A method of differentiating a pluripotent stem cell into a neural cell, including a step of introducing a transcription factor including any one of the following (1) to (11) into a pluripotent stem cell of mammalian origin:
(1) one transcription factor selected from NEUROG2, NEUROG3, NEUROG1, NEUROD1, NRF1, HOXA2, ASCL1, PITX2, NEUROD2, PRDM1, and NFIB;
(2) NEUROG2 and one or more transcription factors selected from NEUROG3, NEUROG1, NEUROD1, NRF1, HOXA2, ASCL1, PITX2, NEUROD2, PRDM1, and NFIB;
(3) NEUROG2, NEUROG3, and one or more transcription factors selected from NEUROG1, NEUROD1, NRF1, HOXA2, ASCL1, PITX2, NEUROD2, PRDM1, and NFIB;
(4) NEUROG2, NEUROG3, NEUROG1, and one or more transcription factors selected from NEUROD1, NRF1, HOXA2, ASCL1, PITX2, NEUROD2, PRDM1, and NFIB;
(5) NEUROG2, NEUROG3, NEUROG1, NEUROD1, and one or more transcription factors selected from NRF1, HOXA2, ASCL1, PITX2, NEUROD2, PRDM1, and NFIB;
(6) NEUROG2, NEUROG3, NEUROG1, NEUROD1, NRF1, and one or more transcription factors selected from HOXA2, ASCL1, PITX2, NEUROD2, PRDM1, and NFIB;
(7) NEUROG2, NEUROG3, NEUROG1, NEUROD1, NRF1, HOXA2, and one or more transcription factors selected from ASCL1, PITX2, NEUROD2, PRDM1, and NFIB;
(8) NEUROG2, NEUROG3, NEUROG1, NEUROD1, NRF1, HOXA2, ASCL1, and one or more transcription factors selected from PITX2, NEUROD2, PRDM1, and NFIB;
(9) NEUROG2, NEUROG3, NEUROG1, NEUROD1, NRF1, HOXA2, ASCL1, PITX2, and one or more transcription factors selected from NEUROD2, PRDM1, and NFIB;
(10) NEUROG2, NEUROG3, NEUROG1, NEUROD1, NRF1, HOXA2, ASCL1, PITX2, NEUROD2, and one or more transcription factors selected from PRDM1 and NFIB;
(11) transcription factors of NEUROG2, NEUROG3, NEUROG1, NEUROD1, NRF1, HOXA2, ASCL1, PITX2, NEUROD2, PRDM1, and NFIB.

15. A method of differentiating a pluripotent stem cell into a neural cell according to the above-mentioned item 14, further including introducing one or more transcription factors selected from TCF4, PDX1, SMAD7, SOX11, RNF2, MXI1, and YY1 into a human pluripotent stem cell.

16. A method of differentiating a pluripotent stem cell into a neural cell according to the above-mentioned item 14 or 15, in which the neural cell is a cell present in a neural cell.

17. A neural cell differentiation inducer, which is capable of differentiating a pluripotent stem cell of mammalian origin into a neural cell, the neural cell differentiation inducer including a transcription factor including any one of the following (1) to (11):
(1) one transcription factor selected from NEUROG2, NEUROG3, NEUROG1, NEUROD1, NRF1, HOXA2, ASCL1, PITX2, NEUROD2, PRDM1, and NFIB;
(2) NEUROG2 and one or more transcription factors selected from NEUROG3, NEUROG1, NEUROD1, NRF1, HOXA2, ASCL1, PITX2, NEUROD2, PRDM1, and NFIB;
(3) NEUROG2, NEUROG3, and one or more transcription factors selected from NEUROG1, NEUROD1, NRF1, HOXA2, ASCL1, PITX2, NEUROD2, PRDM1, and NFIB;
(4) NEUROG2, NEUROG3, NEUROG1, and one or more transcription factors selected from NEUROD1, NRF1, HOXA2, ASCL1, PITX2, NEUROD2, PRDM1, and NFIB;
(5) NEUROG2, NEUROG3, NEUROG1, NEUROD1, and one or more transcription factors selected from NRF1, HOXA2, ASCL1, PITX2, NEUROD2, PRDM1, and NFIB;
(6) NEUROG2, NEUROG3, NEUROG1, NEUROD1, NRF1, and one or more transcription factors selected from HOXA2, ASCL1, PITX2, NEUROD2, PRDM1, and NFIB;

(7) NEUROG2, NEUROG3, NEUROG1, NEUROD1, NRF1, HOXA2, and one or more transcription factors selected from ASCL1, PITX2, NEUROD2, PRDM1, and NFIB;
(8) NEUROG2, NEUROG3, NEUROG1, NEUROD1, NRF1, HOXA2, ASCL1, and one or more transcription factors selected from PITX2, NEUROD2, PRDM1, and NFIB;
(9) NEUROG2, NEUROG3, NEUROG1, NEUROD1, NRF1, HOXA2, ASCL1, PITX2, and one or more transcription factors selected from NEUROD2, PRDM1, and NFIB;
(10) NEUROG2, NEUROG3, NEUROG1, NEUROD1, NRF1, HOXA2, ASCL1, PITX2, NEUROD2, and one or more transcription factors selected from PRDM1 and NFIB; and
(11) transcription factors of NEUROG2, NEUROG3, NEUROG1, NEUROD1, NRF1, HOXA2, ASCL1, PITX2, NEUROD2, PRDM1, and NFIB.
18. A neural cell differentiation inducer according to the above-mentioned item 17, further including one or more transcription factors selected from TCF4, PDX1, SMAD7, SOX11, RNF2, MXI1, and YY1.
19. A neural cell differentiation inducer according to the above-mentioned item 17 or 18, in which the neural cell is a cell present in a neural cell.

Advantageous Effects of Invention

The method of differentiating a pluripotent stem cell into a desired cell type of the present invention can differentiate pluripotent stem cells into desired cell types.

BRIEF DESCRIPTION OF DRAWINGS

FIG. 4A is the human gene expression correlation matrix created in Example 1 (expressed in Z-values).
FIG. 4B is the human gene expression correlation matrix created in Example 1 (expressed in Z-values).
FIG. 4C is the human gene expression correlation matrix created in Example 1 (expressed in Z-values).
FIG. 4D is the human gene expression correlation matrix created in Example 1 (expressed in Z-values).
FIG. 4E is the human gene expression correlation matrix created in Example 1 (expressed in Z-values).
FIG. 4F is the human gene expression correlation matrix created in Example 1 (expressed in Z-values).
FIG. 4G is the human gene expression correlation matrix created in Example 1 (expressed in Z-values).
FIG. 4H is the human gene expression correlation matrix created in Example 1 (expressed in Z-values).
FIG. 4I is the human gene expression correlation matrix created in Example 1 (expressed in Z-values).
FIG. 4J is the human gene expression correlation matrix created in Example 1 (expressed in Z-values).
FIG. 4K is the human gene expression correlation matrix created in Example 1 (expressed in Z-values).
FIG. 4L is the human gene expression correlation matrix created in Example 1 (expressed in Z-values).
FIG. 4M is the human gene expression correlation matrix created in Example 1 (expressed in Z-values).
FIG. 4N is the human gene expression correlation matrix created in Example 1 (expressed in Z-values).
FIG. 4O is the human gene expression correlation matrix created in Example 1 (expressed in Z-values).
FIG. 4P is the human gene expression correlation matrix created in Example 1 (expressed in Z-values).
FIG. 4Q is the human gene expression correlation matrix created in Example 1 (expressed in Z-values).
FIG. 4R is the human gene expression correlation matrix created in Example 1 (expressed in Z-values).
FIG. 4S is the human gene expression correlation matrix created in Example 1 (expressed in Z-values).
FIG. 4T is the human gene expression correlation matrix created in Example 1 (expressed in Z-values).

Figure 1:
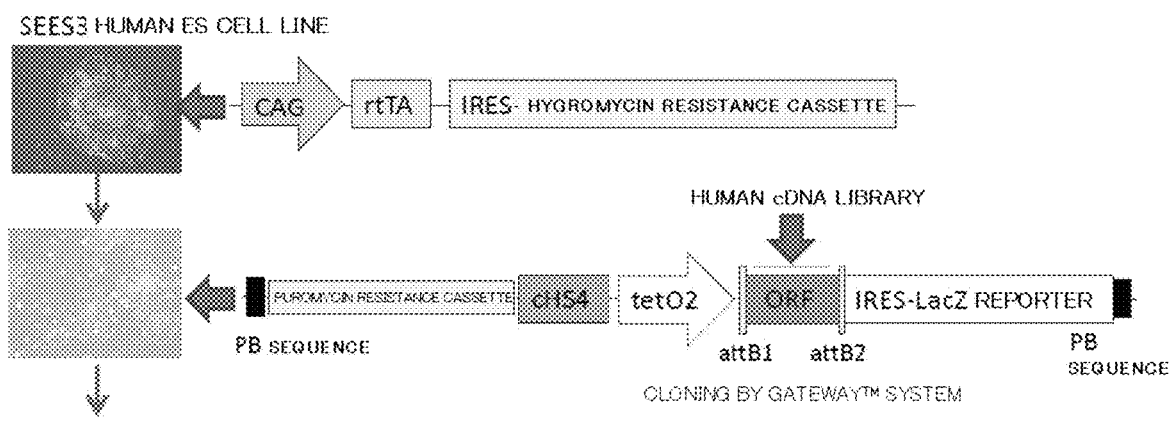
FIG. 1 is an illustration of a human ES cell line expressing a specific transcription factor gene.

DESCRIPTION OF EMBODIMENTS (Method of differentiating Pluripotent Stem Cell into Desired Cell Type of the Present Invention)

A method of differentiating a pluripotent stem cell into a desired cell type of the present invention (hereinafter sometimes referred to as "method of the present invention") includes introducing, into a pluripotent stem cell, a transcription factor or a transcription factor cocktail required for differentiation into a desired cell type, to differentiate the pluripotent stem cell into any one or more cell types among tissues, organs, and cells (horizontal axis) shown in a human gene expression correlation matrix created in Example 1 of the present invention. The method of the present invention is described below.

The term "gene" as used herein encompasses not only double-stranded nucleic acids, but also their respective constituent single strands, such as plus strands (or sense strands) or complementary strands (or antisense strands), linear nucleic acids, and cyclic nucleic acids, and encompasses DNA, RNA, mRNA, cDNA, and the like, unless otherwise stated.

The method of the present invention includes the steps of: selecting at least one kind of positive transcription factor having a z-value of 3 or more for a specific cell type from a matrix shown in FIGS. 3A-3D; and introducing a nucleic acid or mRNA encoding the at least one kind of positive transcription factor, or a protein thereof, or all of the foregoing into a pluripotent stem cell to form a transformed cell or the specific cell type.

A step required for differentiating the transformed cell into the specific cell type may include specific treatment {e.g., culture under a specific environment (culture conditions)} as well as further introduction of another transcription factor.

Further, the method of the present invention may additionally or alternatively include the steps of: selecting at least one kind of negative transcription factor (cold color) from the matrix shown in FIGS. 3A-3D; and introducing a nucleic acid or mRNA encoding the at least one kind of negative transcription factor, or a protein thereof, or both of the foregoing into the pluripotent stem cell to form the transformed cell or the specific cell type. Further, in the method of the present invention, the expression of a transcription factor may be reduced, and a transcription factor gene may be knocked out as well. In order to reduce the expression of, or knock out, the transcription factor, any desirable method may be utilized, and examples thereof include RNA interference, targeted ribozyme, homologous recombination, site-directed mutagenesis, methylation, and any combination thereof.

(z-Value)

z-Values shown in FIGS. 4A-4T of the present invention may be determined by, for example, the following equation (1) disclosed in the literature "Sci Rep 1, 167 (2011)."

$$z = (x_{set} - x_{all}) \times \sqrt{n_{set}} / SD_{all} \quad (1)$$

In the equation, xset represents the average expression change in a specific subset of genes, xall represents the average expression change in all genes, nset represents the size of the gene set, and SDall represents standard deviation of expression change among all genes. xall may be the number of the most upregulated genes, the number of the most downregulated genes, or the total sum of the numbers of the most upregulated genes and the most downregulated genes. The total sum may be a total number equal to, or more than or less than about 100, about 500, about 1,000, about 2,500, about 4,000, about 5,000, about 6,000, about 7,500, about 10,000. nset may be 10, 25, 40, 50, 60, 75, 100, 250, 500, or 1,000 or more genes.

A desirable number of positive and/or negative transcription factors may be selected from the matrix, and for example, 1, 2, 3, 4, 5, 6, 7, 8, 9, 10, 11, 12, 13, 14, 15, 16, 17, 18, 19, 20, 25, or more transcription factors may be selected and used. At least one kind out of the positive transcription factors preferably has a z-value of 3 or more for the specific cell type. Any other positive transcription factor may have a z-value of 3 or more or less than 3. The z-value of each positive transcription factor, or the average z-value of the group of the positive transcription factors may be set to 0 or more, or 1, 2, 3, 4, 5, 6, 7, 8, 9, 10, 11, 12, 13, 14, 15, 16, 17, 18, 19, 20, 25, 30, 40, or 50 or more.

At least one kind out of the negative transcription factors preferably has a z-value of an integer less than or equal to −3 for the specific cell type. Any other negative transcription factor may have a z-value of −3 or less or more. The z-value of each negative transcription factor, or the average z-value of the group of the negative transcription factors may be set to less than 0, or −1, −2, −3, −4, −5, −6, −7, −8, −9, −10, −11, −12, −13, −14, −15, −20, −25, −30, −40, or −50 or less.

(Transcription Factor)

The form of each of the transcription factors to be used in the method of the present invention is not particularly limited, and examples thereof may include, but not particularly limited to, nucleic acids, synthetic mRNAs, and proteins.

Further, a vector for introducing each of the transcription factors into the pluripotent stem cell is not particularly limited, and may be, for example, a viral vector, such as a Sendai virus vector. And, nanoparticle capsules, liposomes, exosomes, or the like containing synthetic mRNAs or proteins may also be used to introduce the transcription factors into the pluripotent stem cell.

In addition, the transcription factors to be used herein may be exemplified by the following:

DLX3 (distal-less homeobox 3), NEUROG3 (neurogenin 3), NEUROG2 (neurogenin 2), NEUROG1 (neurogenin 1), ASCL1 (achaete-scute family bHLH transcription factor 1), NEUROD1 (neurogenic differentiation 1), YY1 (YY1 transcription factor), SOX11 (SRY (sex determining region Y)-box 11), GLIS2 (GLIS family zinc finger 2), PDX1 (pancreatic and duodenal homeobox 1), E2F6 (E2F transcription factor 6), SOX2 (SRY (sex determining region Y)-box 2), CDX2 (caudal type homeobox 2), DLX4 (distal-less homeobox 4), NANOG (Nanog homeobox), MXI1 (MAX interactor 1, dimerization protein), RNF2 (ring finger protein 2), NEUROD2 (neurogenic differentiation 2), ASCL2 (achaete-scute family bHLH transcription factor 2), SREBF2 (sterol regulatory element binding transcription factor 2), SOX15 (SRY (sex determining region Y)-box 15), FOXA2 (forkhead box A2), FOXA1 (forkhead box A1), TBX3 (T-box 3), ARNT2 (aryl-hydrocarbon receptor nuclear translocator 2), PITX2 (paired-like homeodomain 2), PRDM1 (PR domain containing 1, with ZNF domain), TCF4 (transcription factor 4), NFIB (nuclear factor I/B), ZNF281 (zinc finger protein 281), TBX2 (T-box 2), NR2F2 (nuclear receptor subfamily 2, group F, member 2), NFIC {nuclear factor I/C (CCAAT-binding transcription factor)}, NRF1 (nuclear respiratory factor 1), HOXA2 (homeobox A2), TBX5 (T-box 5), ZIC1 (Zic family member 1), HEY1 (hes-related family bHLH transcription factor with YRPW motif 1), CTCF {CCCTC-binding factor (zinc finger protein)}, HES1 (hes family bHLH transcription factor 1), TFAP2C {transcription factor AP-2 gamma (activating enhancer binding protein 2 gamma)}, MYOD1 (myogenic differentiation 1), SALL4 (spalt-like transcription factor 4), TP73 (tumor protein p73), TFE3 (transcription factor binding to IGHM enhancer 3), FOXP1 (forkhead box P1), FOS (FBJ murine osteosarcoma viral oncogene homolog), IRF4 (interferon regulatory factor 4), GATA3 (GATA binding protein 3), JUNB (jun B proto-oncogene), ESX1 (ESX homeobox 1), TGIF1 (TGFB-induced factor homeobox 1), MAB21L3 (mab-21-like 3), DLX6 (distal-less homeobox 6), IRF5 (interferon regulatory factor 5), HSF1 (heat shock transcription factor 1), JUN (jun proto-oncogene), FOSL1 (FOS-like antigen 1), CTCFL {CCCTC-binding factor (zinc finger protein)-like}, FOSL2 (FOS-like antigen 2), FOXG1 (forkhead box G1), THAP11 (THAP domain containing 11), CUX1 (cut-like homeobox 1), ESRRB (estrogen-related receptor beta), HNF4A (hepatocyte nuclear factor 4, alpha), HNF1A (HNF1 homeobox A), NKX2-5 (NK2 homeobox 5), KLF9 (Kruppel-like factor 9), TFAP4 {transcription factor AP-4 (activating enhancer binding protein 4)}, ERG (v-ets avian erythroblastosis virus E26 oncogene homolog), KLF3 (Kruppel-like factor 3), MKRN1 (makorin ring finger protein 1), OLIG2 (oligodendrocyte lineage transcription factor 2), ELF5 {E74-like factor 5

(ets domain transcription factor)}, HOXA9 (homeobox A9), NKX2-1 (NK2 homeobox 1), GRHL2 {grainyhead-like (*Drosophila*)}, USF2 (upstream transcription factor 2, c-fos interacting), KLF4 {Kruppel-like factor 4 (gut)}, ELF1 {E74-like factor 1 (ets domain transcription factor)}, CEBPB {CCAAT/enhancer binding protein (C/EBP), beta}, ETS1 (v-ets avian erythroblastosis virus E26 oncogene homolog 1), ETS2 (v-ets avian erythroblastosis virus E26 oncogene homolog 2), SPIT (Spi-1 proto-oncogene), IRF1 (interferon regulatory factor 1), IRF2 (interferon regulatory factor 2), DMRT1 (doublesex and mab-3 related transcription factor 1), GLI1 (GLI family zinc finger 1), SPIC {Spi-C transcription factor (Spi-1/PU.1 related)}, RUNX3 (runt-related transcription factor 3), GATA2 (GATA binding protein 2), MEF2C (myocyte enhancer factor 2C), FOXL2 (forkhead box L2), FBXO15 (F-box protein 15), HHEX (hematopoietically expressed homeobox), SMAD7 (SMAD family member 7), MEIS2 (Meis homeobox 2), ARID3A {AT rich interactive domain 3A (BRIGHT-like)}, WRNIP1 (Werner helicase interacting protein 1), PPARG (peroxisome proliferator-activated receptor gamma), PTF1A (pancreas specific transcription factor, la), RFX2 {regulatory factor X, 2 (influences HLA class II expression)}, EOMES (eomesodermin), TFCP2L1 (transcription factor CP2-like 1), ZNF274 (zinc finger protein 274), EGR1 (early growth response 1), LHX2 (LIM homeobox 2), TFAP2A {transcription factor AP-2 alpha (activating enhancer binding protein 2 alpha)}, OTX1 (orthodenticle homeobox 1), OVOL2 (ovo-like zinc finger 2), E2F4 (E2F transcription factor 4, p107/p130-binding), RUVBL2 (RuvB-like AAA ATPase 2), SMARCA4 (SWI/SNF related, matrix associated, actin dependent regulator of chromatin, subfamily a, member 4), GTF2F1 (general transcription factor IIF, polypeptide 1, 74 kDa), GBX2 (gastrulation brain homeobox 2), ID1 (inhibitor of DNA binding 1, dominant negative helix-loop-helix protein), PLXNB3 (plexin B3), MYC (v-myc avian myelocytomatosis viral oncogene homolog), ATF2 (activating transcription factor 2), CDYL2 (chromodomain protein, Y-like 2), ZBTB45 (zinc finger and BTB domain containing 45), RSPO1 (R-spondin 1), STAT5A (signal transducer and activator of transcription 5A), LMO1 {LIM domain only 1 (rhombotin 1)}, SMARCB1 (SWI/SNF related, matrix associated, actin dependent regulator of chromatin, subfamily b, member 1), GADD45A (growth arrest and DNA-damage-inducible, alpha), SETDB1 (SET domain, bifurcated 1), SRSF6 (serine/arginine-rich splicing factor 6), ZFAND3 (zinc finger, AN1-type domain 3), IRF3 (interferon regulatory factor 3), KAT8 {K (lysine) acetyltransferase 8}, ZSCAN4 (zinc finger and SCAN domain containing 4), CRY1 {cryptochrome 1 (photolyase-like)}, SIN3A (SIN3 transcription regulator family member A), LMO2 {LIM domain only 2 (rhombotin-like 1)}, NFYB (nuclear transcription factor Y, beta), L3MBTL2 {1(3) mbt-like 2 (*Drosophila*)}, TP53 (tumorproteinp53), RHOXF2 (Rhox homeobox family, member 2), RFX5 {regulatory factor X, 5 (influences HLA class II), EGFLAM (EGF-like, fibronectin type III and laminin G domains), NELFE (negative elongation factor complex member E), XRCC4 (X-ray repair complementing defective repair in Chinese hamster cells 4), ZFP57 (ZFP57 zinc finger protein), SAP30 (Sin3A-associated protein, 30 kDa), Emerald (A virant form of green fluorescence protein [GFP]), BCL6 (B-cell CLL/lymphoma 6), RXRA (retinoid X receptor, alpha), STAT3 {signal transducer and activator of transcription 3 (acute-phase response factor)}, ELL2 (elongation factor, RNA polymerase II, 2), TRPV2 (transient receptor potential cation channel, subfamily V, member 2), HOXC9 (homeobox C9), RARA (retinoic acid receptor, alpha), ZNF263 (zinc finger protein 263), SMAD5 (SMAD family member 5), SUB1 {SUB1 homolog (*S. cerevisiae*)}, SUZ12 (SUZ12 polycomb repressive complex 2 subunit), JAG1 (jagged 1), ATF3 (activating transcription factor 3), ATF1 (activating transcription factor 1), FLI1 (Fli-1 proto-oncogene, ETS transcription factor), ETVS (ets variant 5), KDMSA {lysine (K)-specific demethylase 5A}, NELFA (negative elongation factor complex member A), TCF23 (transcription factor 23), ZNF646 (zinc finger protein 646), SIX5 (SIX homeobox 5), MYBL2 (v-myb avian myeloblastosis viral oncogene homolog-like 2), PAX6 (paired box 6), SMAD2 (SMAD family member 2), SOX9 {SRY (sex determining region Y)-box 9}, STRA13 (stimulated by retinoic acid 13), TBX6 (T-box 6), SMAD1 (SMAD family member 1), FOXH1 (forkhead box H1), OTX2 (orthodenticle homeobox 2), TGIF (TGFB induced factor homeobox 1), and MEIS1 (Meis homeobox 1).

(Pluripotent Stem Cell)

The pluripotent stem cell to be used in the method of the present invention is of mammalian origin, particularly preferably of human origin. The pluripotent stem cell is, for example, a human ES cell, a human iPS cell, or any combination thereof, but is not particularly limited, and encompasses tissue stem cells derived from tissues and organs, dermal fibroblasts, and all kinds of cells derived from tissues and organs.

(ES Cell Line into which Transcription Factor Gene is Introduced)

In the steps of the method of the present invention, a method known per se may be used as a method of introducing each transcription factor gene into the pluripotent stem cell without any particular limitation. However, there may be preferably used an expression cassette inserted between PiggyBac transposase recognition sequences (PB sequences) developed by Woltjen et al. (reference: Nature 458: 766-770, 2009.), which is a mechanism by which a gene to be introduced is actively incorporated into a human ES cell genome. The expression cassette is a system capable of efficiently establishing a genetically modified human ES cell line by introducing a drug selection cassette (see FIG. 1).

(Method for Induction into Desired Cell Type)

Figure 2:
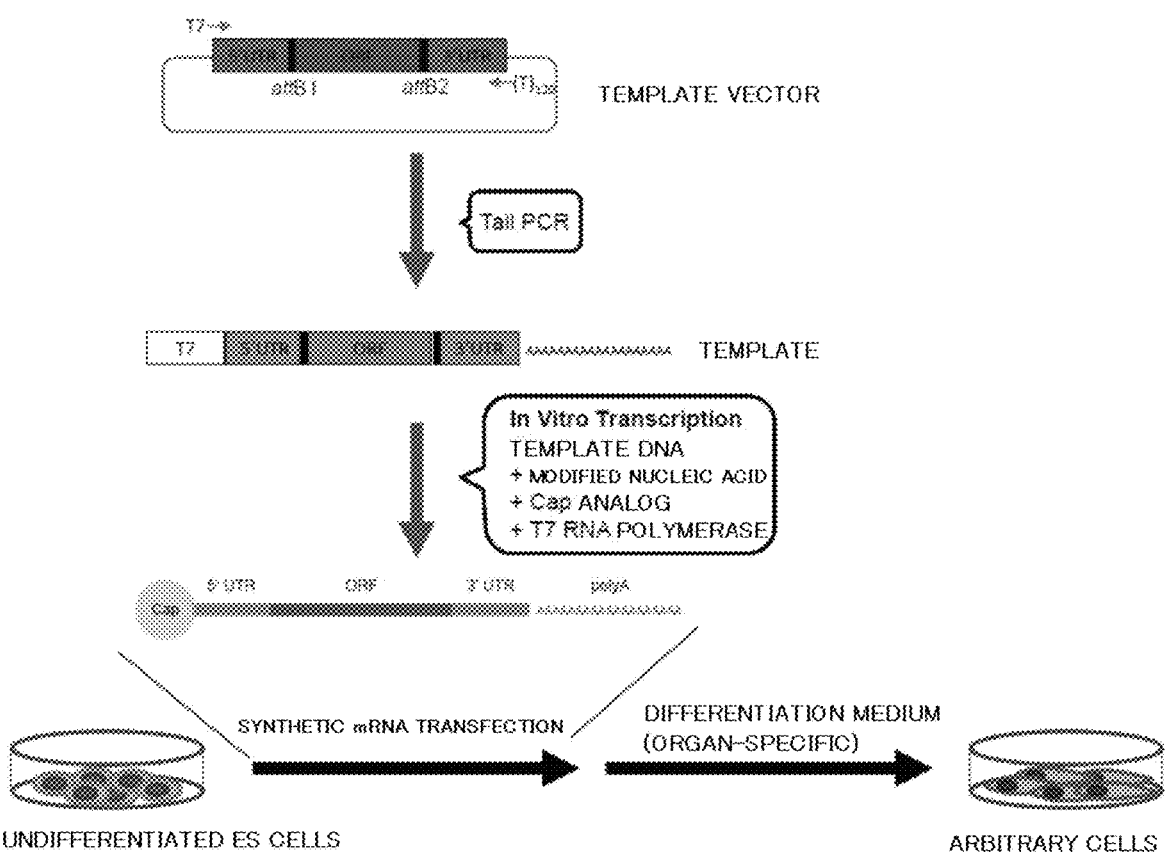
FIG. 2 is an illustration of a method of inducing differentiation into a desired cell type.
Figure 3A:
FIG. 3A is a human gene expression correlation matrix created in Example 1.
Figure 3B:
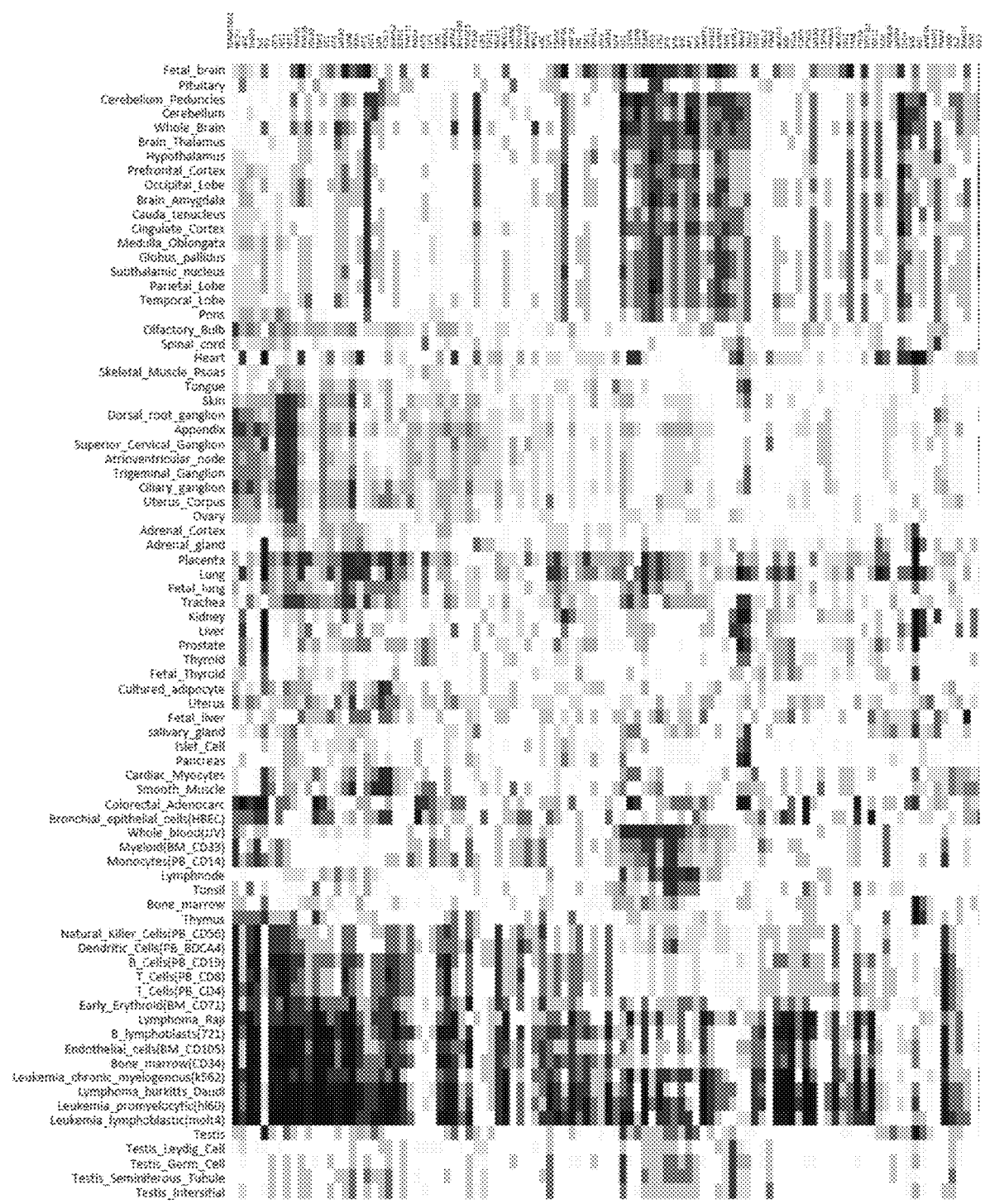
FIG. 3B is the human gene expression correlation matrix created in Example 1.
Figure 3C:
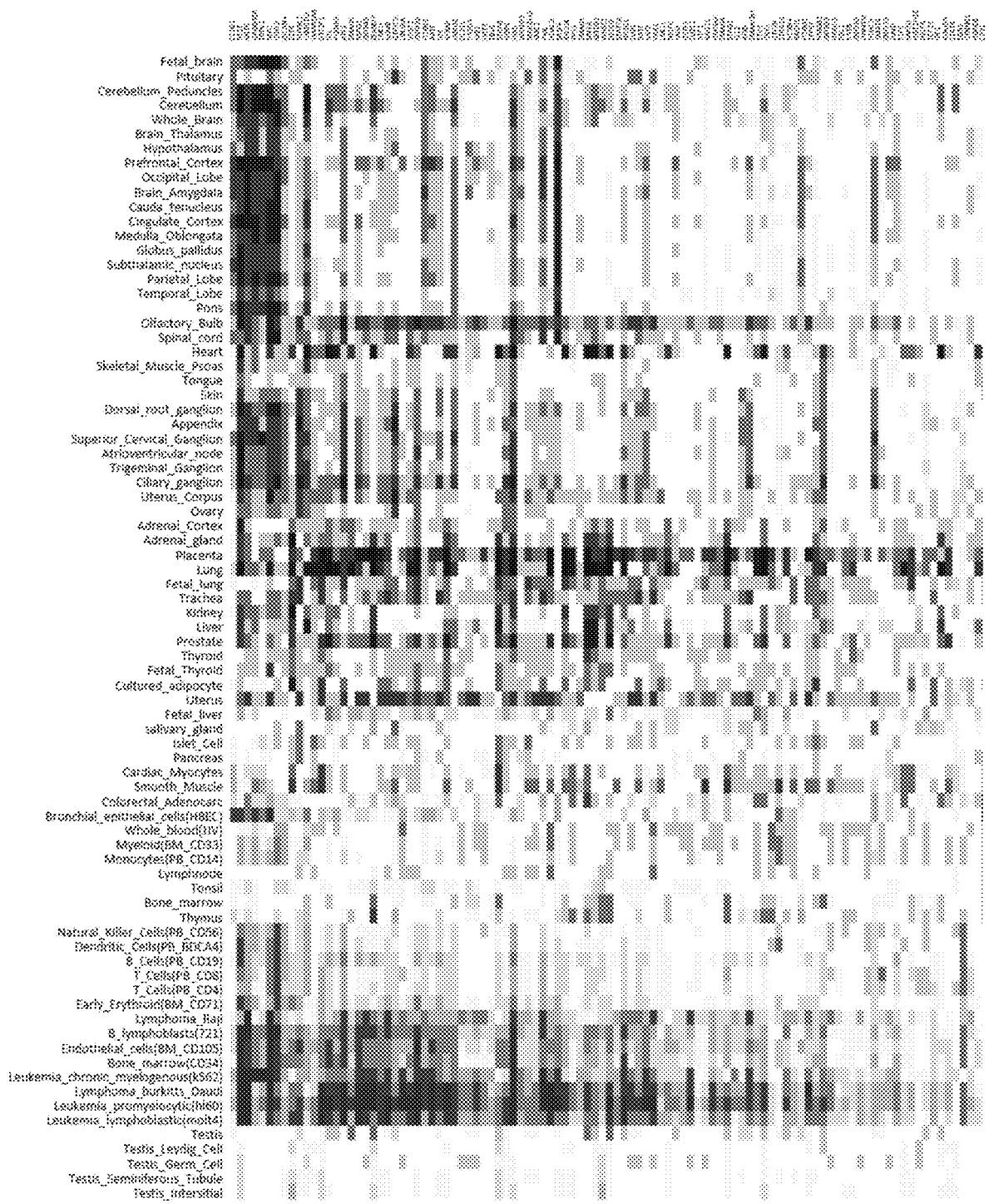
FIG. 3C is the human gene expression correlation matrix created in Example 1.
Figure 3D:
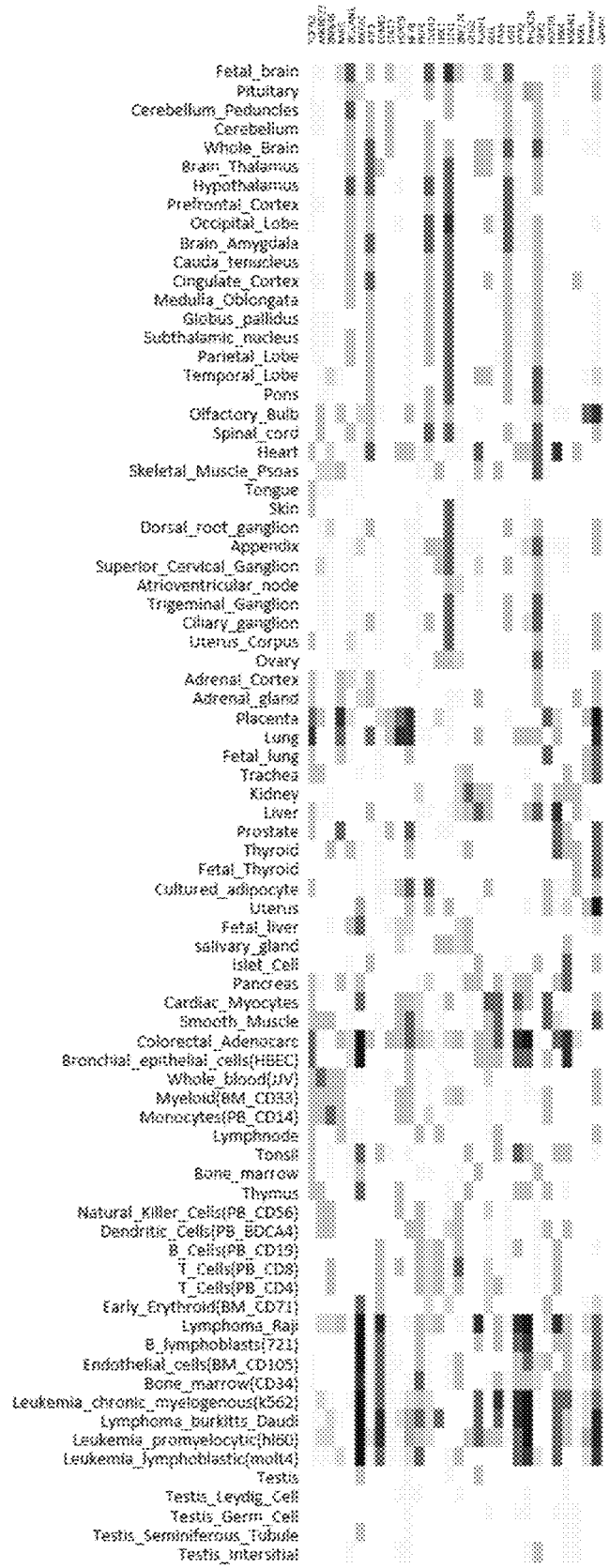
FIG. 3D is the human gene expression correlation matrix created in Example 1.

In the steps of the method of the present invention, a method known per se may be used as a method for induction into the desired cell type without any particular limitation. However, there is preferably used a method of inducing differentiation by efficiently introducing transcription factor gene synthetic mRNA into human pluripotent stem cells through use of a gene expression method involving using synthetic mRNA developed by Warren, Rossi, et al. (reference: Cell Stem Cell 7: 618-630, 2010.), which is a footprint-free forced gene expression method causing no gene incorporation into a host genome (see FIG. 2).

(Method of Utilizing Human Gene Expression Correlation Matrix)

The inventor of the present invention has already created a mouse gene expression correlation matrix and confirmed that the direction of cell differentiation to be caused by induction of expression of a transcription factor can be predicted with considerable accuracy. However, it is known that humans and mice, though both are mammals, are significantly different in some respects of cell differentiation. Further, the inventor of the present invention has newly created a human gene expression correlation matrix through use of human pluripotent stem cells and combinations of human transcription factors. Comparing the human gene expression correlation matrix disclosed for the first time in the present invention and the previously reported mouse gene expression correlation matrix, it has been confirmed that: in mice and humans, transcription factors and combinations of transcription factors required for differentiation into desired cell types are more significantly different than expected; and human cells have higher differentiation speeds than mouse cells.

Besides, the human gene expression correlation matrix of the present invention (see FIGS. 3A-3D and FIGS. 4A-4T) also includes desired organs, tissues, and cells that are not described in the mouse gene expression correlation matrix.

In the gene expression correlation matrix developed and created by the inventor of the present invention, when a transcription factor having a Z-value equal to or higher than a certain value (cut-off value, for example, 7 or more) and/or transcription factors having the top three or more Z-values are selected and introduced into mammalian pluripotent stem cells, the mammalian pluripotent stem cells can be induced into a desired cell type. Examples include the following.

For differentiation into skeletal muscles serving as the desired cell type, Myod1, Mef2c, and Esx1 were selected from transcription factors each having a Z-value of 11 or more in the gene expression correlation matrix and were each introduced alone into mouse ES cells, and as a result, it was confirmed that the mouse ES cells differentiated into skeletal muscles.

For differentiation into liver cells serving as the desired cell type, Hnf4a, Foxa1, Gata2, and Gata3 were selected from transcription factors each having a Z-value of 10 or more in the gene expression correlation matrix and were each introduced alone into mouse ES cells, and as a result, it was confirmed that the mouse ES cells were able to be differentiated into liver cells.

For differentiation into blood cells serving as the desired cell type, Sfpi1, Elf1, Elf5, Myc, Irf2, and Ets1 were selected from transcription factors each having a Z-value of 15 or more in the gene expression correlation matrix and were each introduced alone into mouse ES cells, and as a result, it was confirmed that the mouse ES cells were able to be differentiated into blood cells.

For differentiation into nerve cells serving as the desired cell type, Ascl1, Smad7, Nr2f1, Sox11, Dmrt1, Sox9, Foxg1, and Sox2 were selected from transcription factors each having a Z-value of 12 or more in the gene expression correlation matrix and were each introduced alone into mouse ES cells, and as a result, it was confirmed that the mouse ES cells were able to be differentiated into nerve cells.

In Examples of the present invention, NEUROD1, NEUROD2, NEUROG2, and NEUROG3, which are transcription factors each having a Z-value of 8 or more in the gene expression correlation matrix, were introduced into human embryonic stem cells, and as a result, it was confirmed that the human embryonic stem cells were able to be differentiated into nerve cells.

In Examples of the present invention, NEUROD1 (having a base sequence set forth in SEQ ID NO: 1, and an amino acid sequence set forth in SEQ ID NO: 2), NEUROD2 (having a base sequence set forth in SEQ ID NO: 3, and an amino acid sequence set forth in SEQ ID NO: 4), NEUROG1 (having abase sequence set forth in SEQ ID NO: 5, and an amino acid sequence set forth in SEQ ID NO: 6), NEUROG2 (having a base sequence set forth in SEQ ID NO: 7, and an amino acid sequence set forth in SEQ ID NO: 8), and NEUROG3 (having a base sequence set forth in SEQ ID NO: 9, and an amino acid sequence set forth in SEQ ID NO: 10) were introduced into human embryonic stem cells, and as a result, it was confirmed that the human embryonic stem cells were able to be differentiated into motor cells.

In Examples of the present invention, any one or more of TGIF (which may be any of homeobox protein TGIF1 isoforms a to e, and has, for example, a base sequence set forth in SEQ ID NO: 11, and an amino acid sequence set forth in SEQ ID NO: 12), TCF4 (which may be any of transcription factor 4 isoforms a to n, and has, for example, a base sequence set forth in SEQ ID NO: 13, and an amino acid sequence set forth in SEQ ID NO: 14), PITX2 (which may be any of pituitary homeobox 2 isoforms a to c, and has, for example, a base sequence set forth in SEQ ID NO: 15, and an amino acid sequence set forth in SEQ ID NO: 16), SALL4 (which may be any of sal-like protein 4 isoforms 1 and 2, and has, for example, a base sequence set forth in SEQ ID NO: 17, and an amino acid sequence set forth in SEQ ID NO: 18), and MEIS1 (which has, for example, a base sequence set forth in SEQ ID NO: 19, and an amino acid sequence set forth in SEQ ID NO: 20) were introduced into human embryonic stem cells, and as a result, it was confirmed that the human embryonic stem cells were able to be differentiated into liver cells (hepatoblasts). These transcription factors are completely different from transcription factors (Hnf4a and Foxa1) used in differentiation of mouse ES cells into liver cells.

In Examples of the present invention, any one or more of CDYL2 (which has, for example, a base sequence set forth in SEQ ID NO: 21, and an amino acid sequence set forth in SEQ ID NO: 22), ETS2 (which may be any of transcriptional regulator ERG isoforms 1 to 7, and has, for example, a base sequence set forth in SEQ ID NO: 23, and an amino acid sequence set forth in SEQ ID NO: 24), SPI1 (which may be any of transcription factor PU.1 isoforms 1 and 2, and has, for example, a base sequence set forth in SEQ ID NO: 25, and an amino acid sequence set forth in SEQ ID NO: 26), OVOL2 (which may be any of transcription factor Ovo-like 2 isoforms 1 and 2, and has, abase sequence set forth in SEQ ID NO: 27, and an amino acid sequence set forth in SEQ ID NO: 28), CDX2 (which has, for example, a base sequence set forth in SEQ ID NO: 29, and an amino acid sequence set forth in SEQ ID NO: 30), and CEBPB (which may be any of CCAAT/enhancer-binding protein beta isoforms a to c, and has, for example, a base sequence set forth in SEQ ID NO: 31, and an amino acid sequence set forth in SEQ ID NO: 32) were introduced into human embryonic stem cells, and as a result, it was confirmed that the human embryonic stem cells were able to be differentiated into blood cells (or hematopoietic stem cells).

In Examples of the present invention, SOX9 (which has, for example, a base sequence set forth in SEQ ID NO: 33, and an amino acid sequence set forth in SEQ ID NO: 34) was introduced into human embryonic stem cells, and as a result, it was confirmed that the human embryonic stem cells were able to be differentiated into chondrocytes.

As can be seen from the above, when transcription factors each having a Z-value of 6 or more (or 7 or more, 8 or more, 9 or more, 10 or more, 11 or more, or 12 or more) and/or the top three (or four, five, six, seven, eight, nine, or ten) transcription factors having the highest Z-values in the human gene expression correlation matrix of the present invention are selected and introduced alone or in combination thereof into a human pluripotent stem cell, the human pluripotent stem cell can be induced into a desired cell type. Now, specific examples of the method of the present invention are described.

(Method for Differentiation into Nerve Cell)

A method for differentiation into a nerve cell (in particular, a cell present in the fetal brain, the cerebellum peduncles, the cerebellum, the whole brain, the brain thalamus, the hypothalamus, the prefrontal cortex, the occipital lobe, the brain amygdala, the caudate nucleus, the cingulate cortex, the medulla oblongata, the globus pallidus, the subthalamic nucleus, the parietal lobe, the temporal lobe, or the pons) of the present invention is as described below.

Fetal brain: A single transcription factor, or two or more transcription factors selected from transcription factors shown in FIG. 4A (Fetal_brain) are introduced into a human pluripotent stem cell. Further, as necessary, one or more transcription factors, which are shown in the gene expression correlation matrix other than the foregoing, are simultaneously introduced into the human pluripotent stem cell.

Cerebellum peduncles: A single transcription factor, or two or more transcription factors selected from transcription factors shown in FIG. 4A (Cerebellum_Peduncles) are introduced into a human pluripotent stem cell. Further, as necessary, one or more transcription factors, which are shown in the gene expression correlation matrix other than the foregoing, are simultaneously introduced into the human pluripotent stem cell.

Cerebellum: A single transcription factor, or two or more transcription factors selected from transcription factors shown in FIG. 4A (Cerebellum) are introduced into a human pluripotent stem cell. Further, as necessary, one or more transcription factors, which are shown in the gene expression correlation matrix other than the foregoing, are simultaneously introduced into the human pluripotent stem cell.

Whole brain: A single transcription factor, or two or more transcription factors selected from transcription factors shown in FIG. 4B (Whole_Brain) are introduced into a human pluripotent stem cell. Further, as necessary, one or more transcription factors, which are shown in the gene expression correlation matrix other than the foregoing, are simultaneously introduced into the human pluripotent stem cell.

Brain thalamus: A single transcription factor, or two or more transcription factors selected from transcription factors shown in FIG. 4B (Brain_Thalamus) are introduced into a human pluripotent stem cell. Further, as necessary, one or more transcription factors, which are shown in the gene expression correlation matrix other than the foregoing, are simultaneously introduced into the human pluripotent stem cell.

Hypothalamus: A single transcription factor, or two or more transcription factors selected from transcription factors shown in FIG. 4B (Hypothalamus) are introduced into a human pluripotent stem cell. Further, as necessary, one or more transcription factors, which are shown in the gene expression correlation matrix other than the foregoing, are simultaneously introduced into the human pluripotent stem cell.

Prefrontal cortex: A single transcription factor, or two or more transcription factors selected from transcription factors shown in FIG. 4B (Prefrontal_Cortex) are introduced into a human pluripotent stem cell. Further, as necessary, one or more transcription factors, which are shown in the gene expression correlation matrix other than the foregoing, are simultaneously introduced into the human pluripotent stem cell.

Occipital lobe: A single transcription factor, or two or more transcription factors selected from transcription factors shown in FIG. 4C (Occipital_Lobe) are introduced into a human pluripotent stem cell. Further, as necessary, one or more transcription factors, which are shown in the gene expression correlation matrix other than the foregoing, are simultaneously introduced into the human pluripotent stem cell.

Brain amygdala: A single transcription factor, or two or more transcription factors selected from transcription factors shown in FIG. 4C (Brain_Amygdala) are introduced into a human pluripotent stem cell. Further, as necessary, one or more transcription factors, which are shown in the gene expression correlation matrix other than the foregoing, are simultaneously introduced into the human pluripotent stem cell.

Caudate nucleus: A single transcription factor, or two or more transcription factors selected from transcription factors shown in FIG. 4C (Caudate_nucleus) are introduced into a human pluripotent stem cell. Further, as necessary, one or more transcription factors, which are shown in the gene expression correlation matrix other than the foregoing, are simultaneously introduced into the human pluripotent stem cell.

Cingulate cortex: A single transcription factor, or two or more transcription factors selected from transcription factors shown in FIG. 4C (Cingulate_Cortex) are introduced into a human pluripotent stem cell. Further, as necessary, one or more transcription factors, which are shown in the gene expression correlation matrix other than the foregoing, are simultaneously introduced into the human pluripotent stem cell.

Medulla oblongata: A single transcription factor, or two or more transcription factors selected from transcription factors shown in FIG. 4D (Medulla_Oblongata) are introduced into a human pluripotent stem cell. Further, as necessary, one or more transcription factors, which are shown in the gene expression correlation matrix other than the foregoing, are simultaneously introduced into the human pluripotent stem cell.

Globus pallidus: A single transcription factor, or two or more transcription factors selected from transcription factors shown in FIG. 4D (Globus_pallidus) are introduced into a human pluripotent stem cell. Further, as necessary, one or more transcription factors, which are shown in the gene expression correlation matrix other than the foregoing, are simultaneously introduced into the human pluripotent stem cell.

Subthalamic nucleus: A single transcription factor, or two or more transcription factors selected from transcription factors shown in FIG. 4D (Subthalamic_nucleus) are introduced into a human pluripotent stem cell. Further, as necessary, one or more transcription factors, which are shown in the gene expression correlation matrix other than the foregoing, are simultaneously introduced into the human pluripotent stem cell.

Parietal lobe: A single transcription factor, or two or more transcription factors selected from transcription factors shown in FIG. 4D (Parietal_Lobe) are introduced into a human pluripotent stem cell. Further, as necessary, one or more transcription factors, which are shown in the gene expression correlation matrix other than the foregoing, are simultaneously introduced into the human pluripotent stem cell.

Temporal lobe: A single transcription factor, or two or more transcription factors selected from transcription factors shown in FIG. 4E (Temporal_Lobe) are introduced into a human pluripotent stem cell. Further, as necessary, one or more transcription factors, which are shown in the gene expression correlation matrix other than the foregoing, are simultaneously introduced into the human pluripotent stem cell.

Pons: A single transcription factor, or two or more transcription factors selected from transcription factors shown in FIG. 4E (Pons) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Pituitary (in Particular, Cell Present in Pituitary)}

A method for differentiation into the pituitary of the present invention is as described below.

A single transcription factor, or two or more transcription factors selected from transcription factors shown in FIG. 4A (Pituitary) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Olfactory Nerve (in Particular, Cell Present in Olfactory Nerve)}

A method for differentiation into the olfactory nerve (in particular, the olfactory bulb) of the present invention is as described below.

Olfactory bulb: A single transcription factor, or two or more transcription factors selected from transcription factors shown in FIG. 4E (Olfactory_Bulb) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Spinal Nerve (in Particular, Cell Present in Spinal Nerve)}

A method for differentiation into the spinal nerve (in particular, the spinal cord) of the present invention is as described below.

Spinal cord: A single transcription factor, or two or more transcription factors selected from transcription factors shown in FIG. 4E (Spinal_cord) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Skeletal Muscle (in Particular, Cell Present in Skeletal Muscle)}

A method for differentiation into a skeletal muscle (in particular, the psoas or the tongue) of the present invention is as described below.

Psoas: A single transcription factor, or two or more transcription factors selected from transcription factors shown in FIG. 4F (Skeletal_Muscle_Psoas) are introduced into a human pluripotent stem cell. Further, as necessary, one or more transcription factors, which are shown in the gene expression correlation matrix other than the foregoing, are simultaneously introduced into the human pluripotent stem cell.

Tongue: A single transcription factor, or two or more transcription factors selected from transcription factors shown in FIG. 4F (Tongue) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Skin (in Particular, Cell Present in Skin)}

A method for differentiation into the skin of the present invention is as described below.

A single transcription factor, or two or more transcription factors selected from transcription factors shown in FIG. 4F (Skin) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Ganglion (in Particular, Cell Present in Ganglion)}

A method for differentiation into a ganglion (in particular, the dorsal root ganglion, the superior cervical ganglion, the atrioventricular node, the trigeminal ganglion, or the ciliary ganglion) of the present invention is as described below.

Dorsal root ganglion: A single transcription factor, or two or more transcription factors selected from transcription factors shown in FIG. 4G (Dorsal_root_ganglion) are introduced into a human pluripotent stem cell. Further, as necessary, one or more transcription factors, which are shown in the gene expression correlation matrix other than the foregoing, are simultaneously introduced into the human pluripotent stem cell.

Superior cervical ganglion: A single transcription factor, or two or more transcription factors selected from transcription factors shown in FIG. 4G (Superior_Cervical_Ganglion) are introduced into a human pluripotent stem cell. Further, as necessary, one or more transcription factors, which are shown in the gene expression correlation matrix other than the foregoing, are simultaneously introduced into the human pluripotent stem cell.

Atrioventricular node: A single transcription factor, or two or more transcription factors selected from transcription factors shown in FIG. 4G (Atrioventricular_node) are introduced into a human pluripotent stem cell. Further, as necessary, one or more transcription factors, which are shown in the gene expression correlation matrix other than the foregoing, are simultaneously introduced into the human pluripotent stem cell.

Trigeminal ganglion: A single transcription factor, or two or more transcription factors selected from transcription factors shown in FIG. 4H (Trigeminal_Ganglion) are introduced into a human pluripotent stem cell. Further, as necessary, one or more transcription factors, which are shown in the gene expression correlation matrix other than the foregoing, are simultaneously introduced into the human pluripotent stem cell.

Ciliary ganglion: A single transcription factor, or two or more transcription factors selected from transcription factors shown in FIG. 4H (Ciliary_ganglion) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Ovary (in Particular, Cell Present in Ovary)}

A method for differentiation into the ovary of the present invention is as described below.

A single transcription factor, or two or more transcription factors selected from transcription factors shown in FIG. 4H (Ovary) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Adrenal Gland (in Particular, Cell Present in Adrenal Gland)}

A method for differentiation into the adrenal gland (in particular, the adrenal cortex or the adrenal gland) of the present invention is as described below.

Adrenal cortex: A single transcription factor, or two or more transcription factors selected from transcription factors shown in FIG. 4I (Adrenal_Cortex) are introduced into a human pluripotent stem cell. Further, as necessary, one or more transcription factors, which are shown in the gene expression correlation matrix other than the foregoing, are simultaneously introduced into the human pluripotent stem cell.

Adrenal gland: A single transcription factor, or two or more transcription factors selected from transcription factors shown in FIG. 4I (Adrenal_gland) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Appendix (in Particular, Cell Present in Appendix)}

A method for differentiation into the appendix of the present invention is as described below.

A single transcription factor, or two or more transcription factors selected from transcription factors shown in FIG. 4G (Appendix) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Kidney (in Particular, Cell Present in Kidney)}

A method for differentiation into the kidney of the present invention is as described below.

A single transcription factor, or two or more transcription factors selected from transcription factors shown in FIG. 4J (Kidney) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Liver (in Particular, Cell Present in Liver)}

A method for differentiation into the liver (in particular, the liver or the fetal liver) of the present invention is as described below.

Liver: A single transcription factor, or two or more transcription factors selected from transcription factors shown in FIG. 4J (Liver) are introduced into a human pluripotent stem cell. Further, as necessary, one or more transcription factors, which are shown in the gene expression correlation matrix other than the foregoing, are simultaneously introduced into the human pluripotent stem cell.

Fetal liver: A single transcription factor, or two or more transcription factors selected from transcription factors shown in FIG. 4L (Fetal_liver) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Salivary Gland (in Particular, Cell Present in Salivary Gland)}

A method for differentiation into the salivary gland of the present invention is as described below.

Figures 4K, 4L:
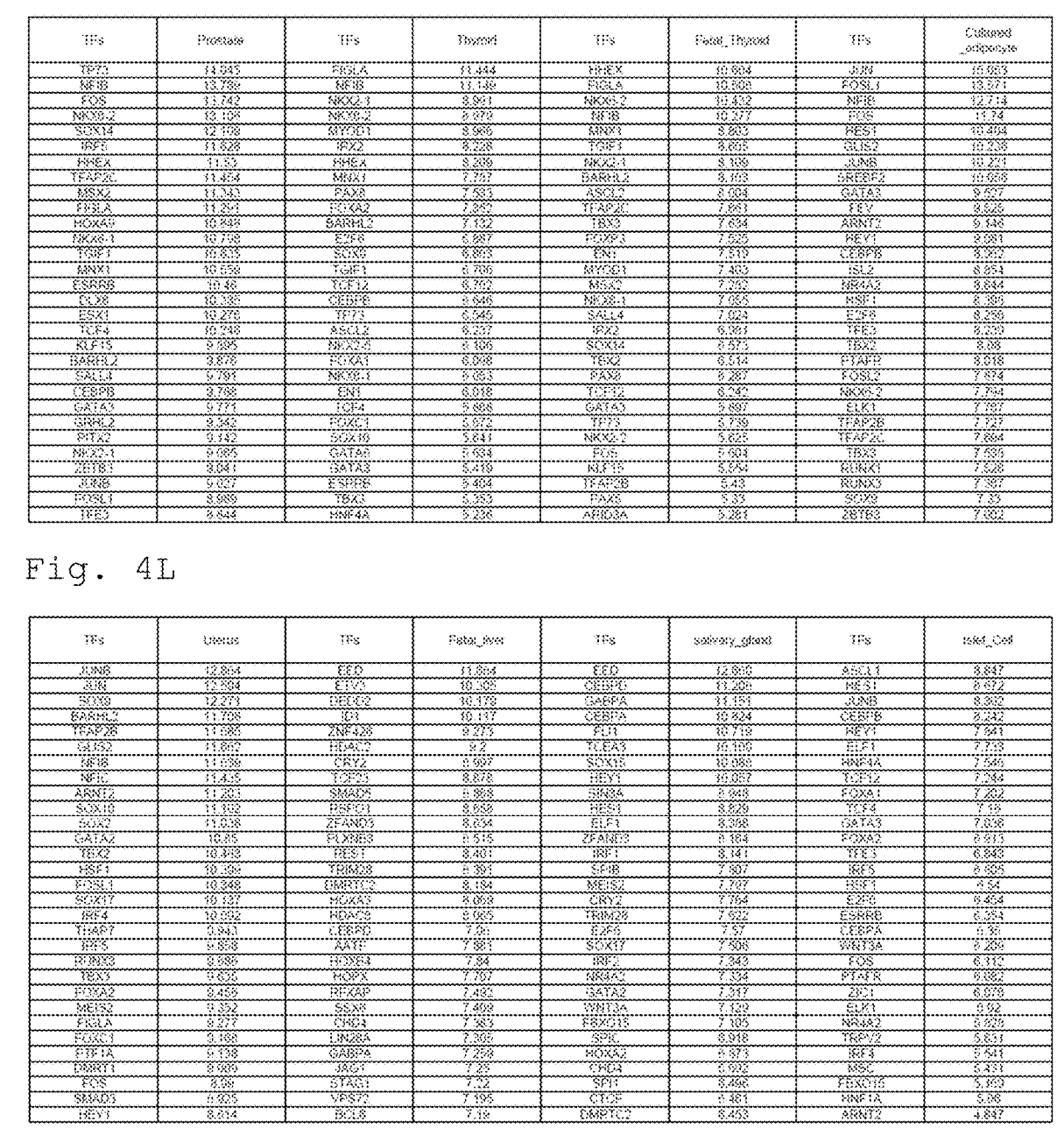

A single transcription factor, or two or more transcription factors selected from transcription factors shown in FIG. 4L (salivary_gland) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Islet (in Particular, Cell Present in Islet)}

A method for differentiation into the islet (in particular, an islet cell) of the present invention is as described below.

A single transcription factor, or two or more transcription factors selected from transcription factors shown in FIG. 4L (Islet_Cell) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Pancreas (in Particular, Cell Present in Pancreas)}

A method for differentiation into the pancreas of the present invention is as described below.

A single transcription factor, or two or more transcription factors selected from transcription factors shown in FIG. 4M (Pancreas) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Prostate (in Particular, Cell Present in Prostate)}

A method for differentiation into the prostate of the present invention is as described below.

A single transcription factor, or two or more transcription factors selected from transcription factors shown in FIG. 4K (Prostate) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Thyroid (in Particular, Cell Present in Thyroid)}

A method for differentiation into the thyroid (in particular, the thyroid or the fetal thyroid) of the present invention is as described below.

Thyroid: A single transcription factor, or two or more transcription factors selected from transcription factors shown in FIG. 4K (Thyroid) are introduced into a human pluripotent stem cell. Further, as necessary, one or more transcription factors, which are shown in the gene expression correlation matrix other than the foregoing, are simultaneously introduced into the human pluripotent stem cell.

Fetal thyroid: A single transcription factor, or two or more transcription factors selected from transcription factors shown in FIG. 4K (Fetal_Thyroid) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Adipocyte)

A method for differentiation into an adipocyte (in particular, a cultured adipocyte) of the present invention is as described below.

Cultured adipocyte: A single transcription factor, or two or more transcription factors selected from transcription factors shown in FIG. 4K (Cultured_adipocyte) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Uterus (in Particular, Cell Present in Uterus)}

A method for differentiation into the uterus (in particular, the uterus or the uterus corpus) of the present invention is as described below.

Uterus: A single transcription factor, or two or more transcription factors selected from transcription factors shown in FIG. 4L (Uterus) are introduced into a human pluripotent stem cell. Further, as necessary, one or more transcription factors, which are shown in the gene expression correlation matrix other than the foregoing, are simultaneously introduced into the human pluripotent stem cell.

Uterus corpus: A single transcription factor, or two or more transcription factors selected from transcription factors shown in FIG. 4H (Uterus_Corpus) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Blood Cell)

A method for differentiation into a blood cell (in particular, whole blood, the bone marrow, a monocyte, a lymphnode, the tonsil, the thymus, a natural killer cell, a dendritic cell, a B cell, a B lymphoblast, a T cell (PB_CD8 or PB_CD4), or an early erythroid) of the present invention is as described below.

Whole blood: A single transcription factor, or two or more transcription factors selected from transcription factors shown in FIG. 4N (Whole_blood (JJV)) are introduced into a human pluripotent stem cell. Further, as necessary, one or more transcription factors, which are shown in the gene expression correlation matrix other than the foregoing, are simultaneously introduced into the human pluripotent stem cell.

Bone marrow: A single transcription factor, or two or more transcription factors selected from transcription factors shown in FIG. 4N (Myeloid (BM_CD33)) are introduced into a human pluripotent stem cell. Further, as necessary, one or more transcription factors, which are shown in the gene expression correlation matrix other than the foregoing, are simultaneously introduced into the human pluripotent stem cell.

Monocyte: A single transcription factor, or two or more transcription factors selected from transcription factors shown in FIG. 4N (Monocytes (PB_CD14)) are introduced into a human pluripotent stem cell. Further, as necessary, one or more transcription factors, which are shown in the gene expression correlation matrix other than the foregoing, are simultaneously introduced into the human pluripotent stem cell.

Lymphnode: A single transcription factor, or two or more transcription factors selected from transcription factors shown in FIG. 4O (Lymphnode) are introduced into a human pluripotent stem cell. Further, as necessary, one or more transcription factors, which are shown in the gene expression correlation matrix other than the foregoing, are simultaneously introduced into the human pluripotent stem cell.

Tonsil: A single transcription factor, or two or more transcription factors selected from transcription factors shown in FIG. 4O (Tonsil) are introduced into a human pluripotent stem cell. Further, as necessary, one or more transcription factors, which are shown in the gene expression correlation matrix other than the foregoing, are simultaneously introduced into the human pluripotent stem cell.

Thymus: A single transcription factor, or two or more transcription factors selected from transcription factors shown in FIG. 4O (Thymus) are introduced into a human pluripotent stem cell. Further, as necessary, one or more transcription factors, which are shown in the gene expression correlation matrix other than the foregoing, are simultaneously introduced into the human pluripotent stem cell.

Natural killer cell: A single transcription factor, or two or more transcription factors selected from transcription factors shown in FIG. 4P (Natural_Killer_Cells (PB_CD56)) are introduced into a human pluripotent stem cell. Further, as necessary, one or more transcription factors, which are shown in the gene expression correlation matrix other than the foregoing, are simultaneously introduced into the human pluripotent stem cell.

Dendritic cell: A single transcription factor, or two or more transcription factors selected from transcription factors shown in FIG. 4P (Dendritic_Cells (PB_BDCA4)) are introduced into a human pluripotent stem cell. Further, as necessary, one or more transcription factors, which are shown in the gene expression correlation matrix other than the foregoing, are simultaneously introduced into the human pluripotent stem cell.

B cell: A single transcription factor, or two or more transcription factors selected from transcription factors shown in FIG. 4P (B_Cells (PB_CD19)) are introduced into a human pluripotent stem cell. Further, as necessary, one or more transcription factors, which are shown in the gene expression correlation matrix other than the foregoing, are simultaneously introduced into the human pluripotent stem cell.

B lymphoblast: A single transcription factor, or two or more transcription factors selected from transcription factors shown in FIG. 4Q (B_lymphoblasts (721)) are introduced into a human pluripotent stem cell. Further, as necessary, one or more transcription factors, which are shown in the gene expression correlation matrix other than the foregoing, are simultaneously introduced into the human pluripotent stem cell.

T cell (PB_CD8): A single transcription factor, or two or more transcription factors selected from transcription factors shown in FIG. 4P (T_Cells (PB_CD8)) are introduced into a human pluripotent stem cell. Further, as necessary, one or more transcription factors, which are shown in the gene expression correlation matrix other than the foregoing, are simultaneously introduced into the human pluripotent stem cell.

T cell (PB_CD4): A single transcription factor, or two or more transcription factors selected from transcription factors shown in FIG. 4Q (T_Cells (PB_CD4)) are introduced into a human pluripotent stem cell. Further, as necessary, one or more transcription factors, which are shown in the gene expression correlation matrix other than the foregoing, are simultaneously introduced into the human pluripotent stem cell.

Early erythroid: A single transcription factor, or two or more transcription factors selected from transcription factors shown in FIG. 4Q (Early Erythroid (BM_CD71)) are introduced into a human pluripotent stem cell. Further, as necessary, one or more transcription factors, which are shown in the gene expression correlation matrix other than the foregoing, are simultaneously introduced into the human pluripotent stem cell.

Lymphoma-derived Raji cell: A single transcription factor, or two or more transcription factors selected from transcription factors shown in FIG. 4Q (Lymphoma_Raji) are introduced into a human pluripotent stem cell. Further, as necessary, one or more transcription factors, which are shown in the gene expression correlation matrix other than the foregoing, are simultaneously introduced into the human pluripotent stem cell.

Chronic myelogenous leukemia cell: A single transcription factor, or two or more transcription factors selected from transcription factors shown in FIG. 4R (Leukemia_chronic_myelogenous (k562)) are introduced into a human pluripotent stem cell. Further, as necessary, one or more transcription factors, which are shown in the gene expression correlation matrix other than the foregoing, are simultaneously introduced into the human pluripotent stem cell.

Burkitt's lymphoma Daudi cell line: A single transcription factor, or two or more transcription factors selected from transcription factors shown in FIG. 4R (Lymphoma_burkitts_Daudi) are introduced into a human pluripotent stem cell. Further, as necessary, one or more transcription factors, which are shown in the gene expression correlation matrix other than the foregoing, are simultaneously introduced into the human pluripotent stem cell.

Promyelocytic leukemia cell: A single transcription factor, or two or more transcription factors selected from transcription factors shown in FIG. 4S (Leukemia_promyelocytic (h160)) are introduced into a human pluripotent stem cell. Further, as necessary, one or more transcription factors, which are shown in the gene expression correlation matrix other than the foregoing, are simultaneously introduced into the human pluripotent stem cell.

Lymphoblastic leukemia cell: A single transcription factor, or two or more transcription factors selected from transcription factors shown in FIG. 4S (Leukemia_lymphoblastic (molt4)) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Bone Marrow (Cell Present in Bone Marrow)}

A method for differentiation into the bone marrow of the present invention is as described below.

Figures 4O, 4P:
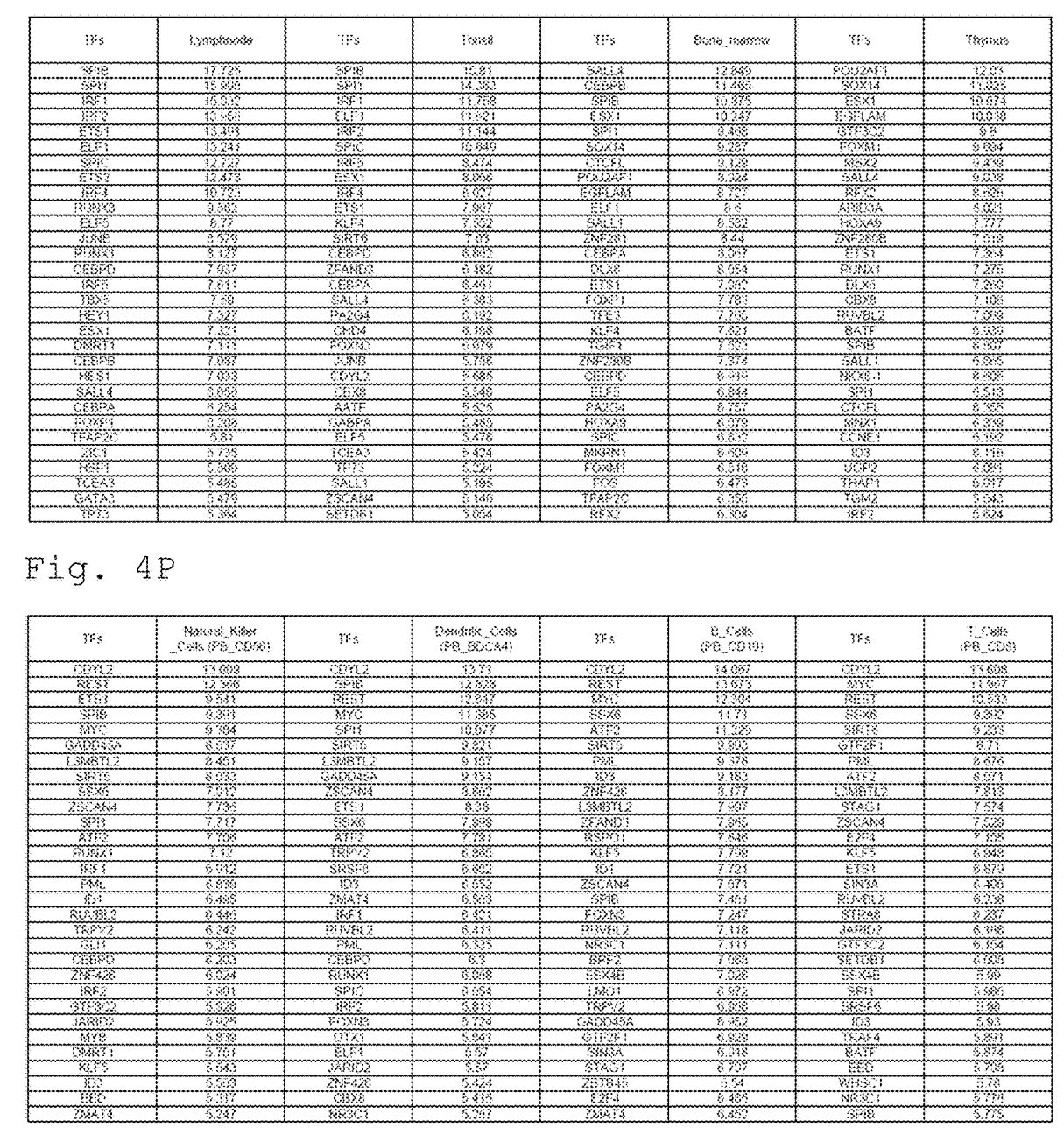

A single transcription factor, or two or more transcription factors selected from transcription factors shown in FIG. 4O (Bone_marrow) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Hematopoietic Stem Cell)

A method for differentiation into a hematopoietic stem cell of the present invention is as described below.

Figures 4Q, 4R:
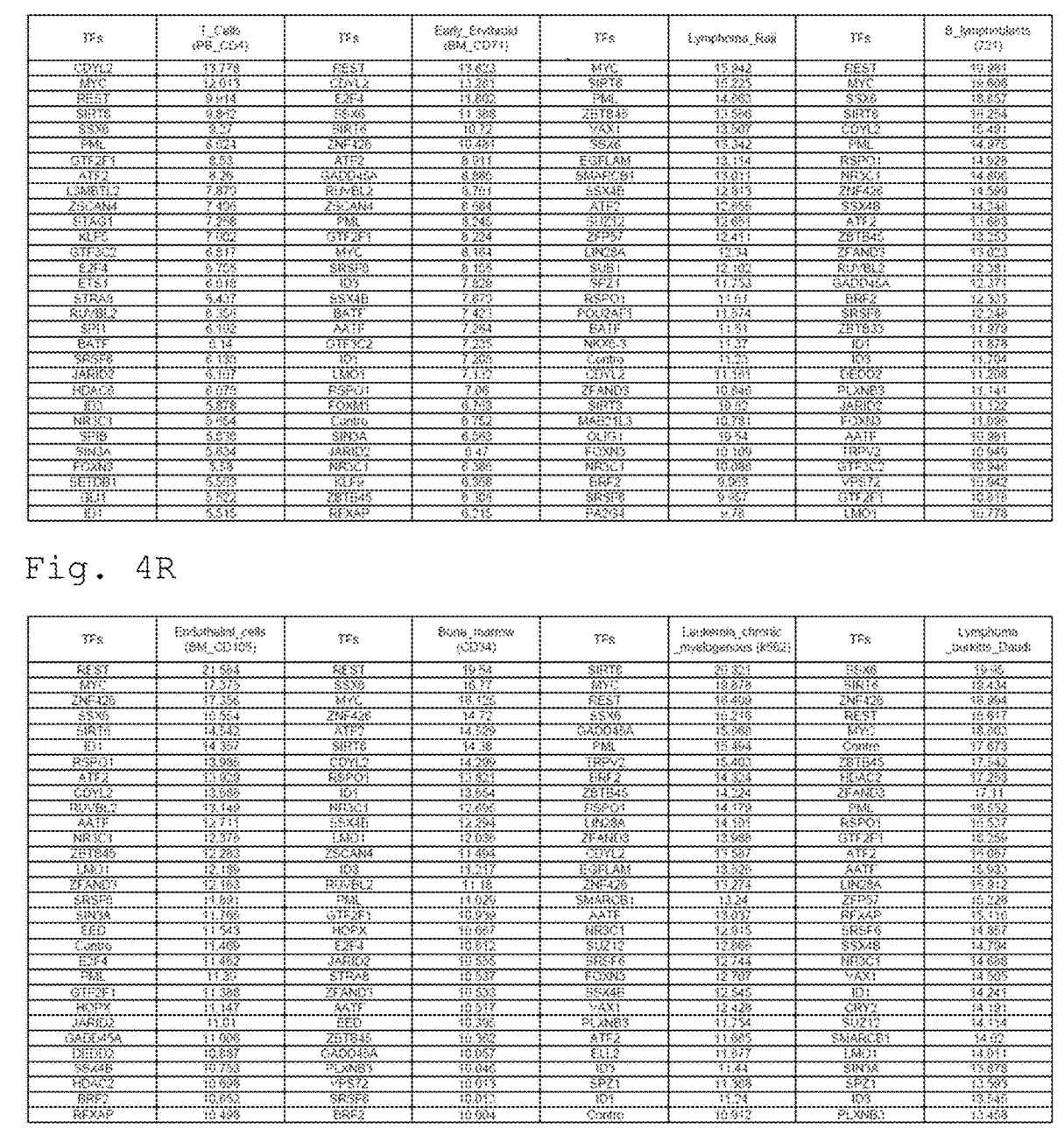
Figures 4S, 4T:
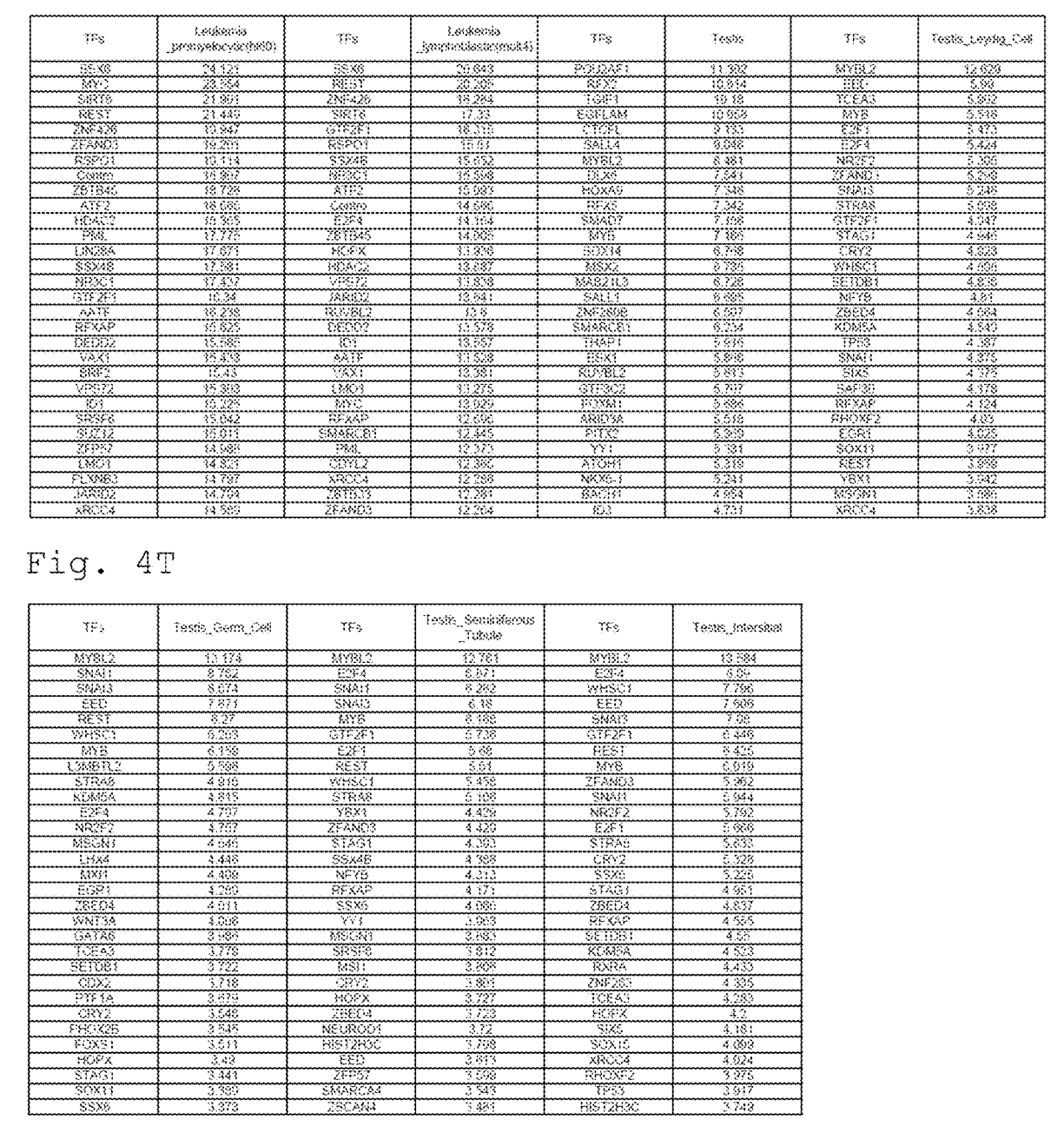

A single transcription factor, or two or more transcription factors selected from transcription factors shown in FIG. 4R (Bone_marrow (CD34)) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Vascular Endothelial Cell)

A method for differentiation into a vascular endothelial cell of the present invention is as described below.

A single transcription factor, or two or more transcription factors selected from transcription factors shown in FIG. 4R (Endothelial_cells (BM_CD105)) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Testis (in Particular, Cell Present in Testis)}

A method for differentiation into the testis (in particular, the testis, a testis Leydig cell, a testis germ cell, the testis seminiferous tubule, or a testis interstitial cell) of the present invention is as described below.

Testis: A single transcription factor, or two or more transcription factors selected from transcription factors shown in FIG. 4S (Testis) are introduced into a human pluripotent stem cell. Further, as necessary, one or more transcription factors, which are shown in the gene expression correlation matrix other than the foregoing, are simultaneously introduced into the human pluripotent stem cell.

Testis Leydig cell: A single transcription factor, or two or more transcription factors selected from transcription factors shown in FIG. 4S (Testis_Leydig_Cell) are introduced into a human pluripotent stem cell. Further, as necessary, one or more transcription factors, which are shown in the gene expression correlation matrix other than the foregoing, are simultaneously introduced into the human pluripotent stem cell.

Testis germ cell: A single transcription factor, or two or more transcription factors selected from transcription factors shown in FIG. 4T (Testis_Germ_Cell) are introduced into a human pluripotent stem cell. Further, as necessary, one or more transcription factors, which are shown in the gene expression correlation matrix other than the foregoing, are simultaneously introduced into the human pluripotent stem cell.

Testis seminiferous tubule: A single transcription factor, or two or more transcription factors selected from transcription factors shown in FIG. 4T (Testis_Seminiferous_Tubule) are introduced into a human pluripotent stem cell. Further, as necessary, one or more transcription factors, which are shown in the gene expression correlation matrix other than the foregoing, are simultaneously introduced into the human pluripotent stem cell.

Testis interstitial cell: A single transcription factor, or two or more transcription factors selected from transcription factors shown in FIG. 4T (Testis_Interstitial) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Heart (in Particular, Cell Present in Heart)}

A method for differentiation into the heart (in particular, the heart or a cardiac myocyte) of the present invention is as described below.

Heart: A single transcription factor, or two or more transcription factors selected from transcription factors shown in FIG. 4F (Heart) are introduced into a human pluripotent stem cell. Further, as necessary, one or more transcription factors, which are shown in the gene expression correlation matrix other than the foregoing, are simultaneously introduced into the human pluripotent stem cell.

Cardiac myocyte: A single transcription factor, or two or more transcription factors selected from transcription factors shown in FIG. 4M (Cardiac_Myocytes) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Placenta (in Particular, Cell Present in Placenta)}

A method for differentiation into the placenta of the present invention is as described below.

A single transcription factor, or two or more transcription factors selected from transcription factors shown in FIG. 4I (Placenta) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Smooth Muscle (in Particular, Cell Present in Smooth Muscle)}

A method for differentiation into a smooth muscle of the present invention is as described below.

A single transcription factor, or two or more transcription factors selected from transcription factors shown in FIG. 4M (Smooth_Muscle) are introduced into a human pluripotent stem cell. Further, as necessary, one or more transcription factors, which are shown in the gene expression correlation matrix other than the foregoing, are simultaneously introduced into the human pluripotent stem cell.

{Method for Differentiation into Lung (in Particular, Cell Present in Lung)}

A method for differentiation into the lung (in particular, the lung, a bronchial epithelial cell, the fetal lung, or the trachea) of the present invention is as described below.

Lung: A single transcription factor, or two or more transcription factors selected from transcription factors shown in FIG. 4I (Lung) are introduced into a human pluripotent stem cell. Further, as necessary, one or more transcription factors, which are shown in the gene expression correlation matrix other than the foregoing, are simultaneously introduced into the human pluripotent stem cell.

Bronchial epithelial cell: A single transcription factor, or two or more transcription factors selected from transcription factors shown in FIG. 4N (Bronchial_epithelial_cells (HBEC)) are introduced into a human pluripotent stem cell. Further, as necessary, one or more transcription factors, which are shown in the gene expression correlation matrix other than the foregoing, are simultaneously introduced into the human pluripotent stem cell.

Fetal lung: A single transcription factor, or two or more transcription factors selected from transcription factors shown in FIG. 4J (Fetal_lung) are introduced into a human pluripotent stem cell. Further, as necessary, one or more transcription factors, which are shown in the gene expression correlation matrix other than the foregoing, are simultaneously introduced into the human pluripotent stem cell.

Trachea: A single transcription factor, or two or more transcription factors selected from transcription factors shown in FIG. 4J (Trachea) are introduced into a human pluripotent stem cell. Further, as necessary, one or more transcription factors, which are shown in the gene expression correlation matrix other than the foregoing, are simultaneously introduced into the human pluripotent stem cell.

(Method for Differentiation into Colorectal Adenocarcinoma Cell)

A method for differentiation into a colorectal adenocarcinoma cell of the present invention is as described below.

Colorectal adenocarcinoma cell: A single transcription factor, or two or more transcription factors selected from transcription factors shown in FIG. 4M (Colorectal Adenocarcinoma) are introduced into a human pluripotent stem cell. Further, as necessary, one or more transcription factors, which are shown in the gene expression correlation matrix other than the foregoing, are simultaneously introduced into the human pluripotent stem cell.

(Differentiation Inducer to be Used for Method of Differentiating Pluripotent Stem Cell into Desired Cell Type)

A differentiation inducer to be used for the method of differentiating a pluripotent stem cell into a desired cell type of the present invention (hereinafter sometimes referred to as "differentiation inducer of the present invention") is a composition including at least a transcription factor required for the method of the present invention.

Specifically, the differentiation inducer of the present invention includes a transcription factor in any of, for example, the following forms: nucleic acids, synthetic mRNAs, proteins, and viral vectors carrying the foregoing, nanoparticle capsules carrying the foregoing, liposomes carrying the foregoing, or Exosome carrying the foregoing.

The transcription factor in the form of a protein included in the differentiation inducer of the present invention may be exemplified by the following:

(1) a transcription factor, or a protected derivative, sugar chain-modified product, acylated derivative, or acetylated derivative of the transcription factor;

(2) a transcription factor that has 90% (or 92%, 94%, 96%, 98%, or 99%) or more homology to the above-mentioned transcription factor and has a peculiar transcription factor action substantially equivalent to that of the transcription factor; and (3) a transcription factor that has 100 to 10, 50 to 30, 40 to 20, 10 to 5, or 5 to 1 amino acid substituted, deleted, inserted, and/or added in the transcription factor as described in any one of the above-mentioned items and has a peculiar transcription factor action substantially equivalent to that of the transcription factor.

The transcription factor in the form of mRNA, synthetic mRNA, or a nucleic acid included in the differentiation inducer of the present invention may be exemplified by the following:

(4) a gene encoding a polypeptide formed of the transcription factor of any one or more of the above-mentioned items;

(5) a gene encoding a polypeptide that has 1 to 20 (or 1 to 15, 1 to 10, 1 to 7, 1 to 5, or 1 to 3) amino acids substituted, deleted, inserted, and/or added in the amino acid sequence of the transcription factor of any one or more of the above-mentioned items and has a peculiar transcription factor action substantially equivalent to that of the transcription factor;

(6) a gene encoding a polypeptide that has 90% (or 92%, 94%, 96%, 98%, or 99%) or more homology to the amino acid sequence of the transcription factor of any one or more of the above-mentioned items and has a peculiar transcription factor action substantially equivalent to that of the transcription factor; and (7) a gene encoding a polypeptide that has 90% (or 92%, 94%, 96%, 98%, or 99%) or more homology to the base sequence of the transcription factor of any one or more of the above-mentioned items and has a peculiar transcription factor action substantially equivalent to that of the transcription factor.

A transcription factor having a mutation may be a naturally occurring one, or may be one obtained by introducing a mutation on the basis of a gene of natural origin. Means for introducing a mutation is known per se, and for example, a site-directed mutagenesis method, a homologous gene recombination method, a primer extension method, a polymerase chain reaction (hereinafter abbreviated as PCR), and the like may be used alone or in combination thereof as appropriate.

The method may be performed in conformity with any of methods disclosed in the literatures ("Molecular Cloning: A Laboratory Manual, second edition" edited by Sambrook et al., 1989, Cold Spring Harbor Laboratory; and "Lab Manual: Genetic Engineering" edited by Masami Muramatsu, 1988, Maruzen), or by modifying these methods, and Ulmer's technology (Ulmer, K. M., "Science", 1983, volume 219, p. 666-671) may also be utilized. In the case of a peptide, from the viewpoint of preventing alteration of basic properties of the peptide (e.g., physical properties, function, physiological activity, or immunological activity) in the introduction of a mutation, for example, mutual substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable.

Examples of the differentiation inducer of the present invention are listed below.

Nerve cell differentiation inducer (in particular, a fetal brain differentiation inducer, a cerebellum peduncle differentiation inducer, a cerebellum differentiation inducer, a whole brain differentiation inducer, a brain thalamus differentiation inducer, a hypothalamus differentiation inducer, a prefrontal cortex differentiation inducer, an occipital lobe differentiation inducer, a brain amygdala differentiation inducer, a caudate nucleus differentiation inducer, a cingulate cortex differentiation inducer, a medulla oblongata differentiation inducer, a globus pallidus differentiation inducer, a subthalamic nucleus differentiation inducer, a parietal lobe differentiation inducer, a temporal lobe differentiation inducer, or a pons differentiation inducer)

Motor nerve Differentiation Inducer

The motor nerve means a motor neuron or a motoneuron. There are two kinds of motor neurons: central and peripheral motor neurons. The central motor neuron is a nerve from the brain to the spinal cord, and the peripheral motor neuron is a nerve from the spinal cord to a muscle. In particular, a peripheral motor nerve is preferred.

Pituitary differentiation inducer

Olfactory nerve differentiation inducer (in particular, an olfactory bulb differentiation inducer)

Spinal nerve differentiation inducer (in particular, a spinal cord differentiation inducer)

Skeletal muscle differentiation inducer (in particular, a psoas differentiation inducer or a tongue differentiation inducer)

Skin differentiation inducer

Ganglion differentiation inducer (in particular, a dorsal root ganglion differentiation inducer, a superior cervical ganglion differentiation inducer, an atrioventricular node differentiation inducer, a trigeminal ganglion differentiation inducer, or a ciliary ganglion differentiation inducer)

Ovary differentiation inducer

Adrenal gland differentiation inducer (in particular, an adrenal cortex differentiation inducer or an adrenal gland differentiation inducer)

Appendix differentiation inducer

Kidney differentiation inducer

Liver differentiation inducer (in particular, a liver differentiation inducer or a fetal liver differentiation inducer)

Salivary gland differentiation inducer

Islet differentiation inducer (in particular, an islet cell differentiation inducer)

Pancreas differentiation inducer

Prostate differentiation inducer

Thymus differentiation inducer (in particular, a thyroid differentiation inducer or a fetal thyroid differentiation inducer)

Adipocyte differentiation inducer (in particular, a cultured adipocyte differentiation inducer)

Uterus differentiation inducer (in particular, a uterus differentiation inducer or a uterus corpus differentiation inducer)

Blood cell differentiation inducer (in particular, a whole blood differentiation inducer, a bone marrow differentiation inducer, a monocyte differentiation inducer, a lymphnode differentiation inducer, a tonsil differentiation inducer, a thymus differentiation inducer, a natural killer cell differentiation inducer, a dendritic cell differentiation inducer, a B cell differentiation inducer, a B lymphoblast differentiation inducer, a T cell (PB_CD8 or PB_CD4) differentiation inducer, or an early erythroid differentiation inducer)

Bone marrow differentiation inducer

Blood cell (or hematopoietic stem cell) differentiation inducer

Vascular endothelial cell differentiation inducer

Testis differentiation inducer (in particular, a testis differentiation inducer, a testis Leydig cell differentiation inducer, a testis germ cell differentiation inducer, a testis seminiferous tubule differentiation inducer, or a testis interstitial cell differentiation inducer)

Heart differentiation inducer (in particular, a heart differentiation inducer or a cardiac myocyte differentiation inducer)

Placenta differentiation inducer

Smooth muscle differentiation inducer

Lung differentiation inducer (in particular, a lung differentiation inducer, a bronchial epithelial cell differentiation inducer, a fetal lung differentiation inducer, or a trachea differentiation inducer)

Cartilage differentiation inducer

The present invention is specifically described below by way of Examples. However, the present invention is not limited thereto. All Examples of the present invention have been approved by the Ethics Committee of Keio University School of Medicine.

Example 1

(Creation of Human Gene Expression Correlation Matrix)

In this Example, a human gene expression correlation matrix (see FIGS. 3A-3D and FIGS. 4A-4T) was created. The details are as described below.

With reference to the disclosures of the literatures "Cell Stem Cell 5, 420-433 (2009)" and "Sci Rep 1, 167 (2011),"

gene expression profiles of human ES cells under 48-hour forced expression (DOX+) or not under forced expression (DOX−) were obtained by an RNA sequencing method (RNA-seq) for 175 transcription factors one by one. Further, 50-bp-long sequenced RNA fragments were aligned with human genome sequences by computer analysis. Next, the RNA fragments were identified for matching to mRNA/ncRNA from Ensembl and RefSeq (gene coordinates of transcripts were downloaded from the UCSC database, genome version hg19, hgdownload.soe.ucsc.edu/goldenPath/hg19 on Aug. 5, 2014).

Ensembl data was mainly used, and transcripts that were unable to be covered by the Ensembl data were complemented with RefSeq. With regard to the number of matches to the genome, a case in which the number of mismatches was 2 or less and the number of hits in the genome was 10 or less was adopted. The fragments were weighted by 1/n, where n represented the number of hits in a genome. The fragments were identified as transcription factors when: directions matched; the boundaries of genes and the boundaries of introns matched within a 5-bp distance; and the total matching length was 90% or less of the read length.

With regard to a gene expression change induced by forced expression of each transcription factor, a DOX+ sample log-transformed expression value (each clone was replicated once) was normalized by subtracting the log-transformed expression value of the corresponding DOX− sample and adding the median of the log-transformed expression values of all DOX− samples.

An association between the gene expression change induced by overexpression of a transcription factor and tissue-specific gene expression was evaluated on the basis of a correlation between the GNF database (see Non Patent Literature 22) and the results of RNA-seq.

The correlation was analyzed between the response of gene expression to transcription factor introduction in various tissues in the human GNF database ver. 2 and the median-subtraction log-transformed gene expression value. The correlation analysis was performed using 9,980 genes that had shown significant values in both data sets. Criteria for significance of the GNF database were set to a false discovery rate (FDR) of 0.05 or less and a change of 2-fold or more. A correlation matrix was calculated by sorting with ExAtlas, lgsun.grc.nia.nih.gov/exatlas using hierarchical clustering.

The results of the creation of the human gene expression correlation matrix are shown in FIGS. 3A-3D and FIGS. 4A-4T. In FIGS. 3A-3D, a correlation matrix between "change in gene expression induced by forced expression of a specific transcription factor (horizontal axis)" and "tissue-specific gene expression from the GNF database (vertical axis)" is shown. Each cell of the matrix represents the significance of a correlation between "change in gene expression induced by forced expression of a specific transcription factor (measured in log-ratio, horizontal axis)" and "tissue-specific gene expression from the GNF database (vertical axis)" (z-value: Z-value). In FIGS. 4A-4T, the top 30 of the Z-values expressed in actual numbers are shown for each of the cells, the tissues, and the organs shown in FIGS. 3A-3D.

Example 2

(Method for Differentiation into Desired Cell Type)

Through use of the human gene expression correlation matrix obtained in Example 1 of the present invention (FIGS. 3A-3D and FIGS. 4A-4T), pluripotent stem cells can be differentiated into the cells, the tissues, and the organs shown in FIGS. 3A-3D. A molecular biological technique known per se may be utilized as a differentiation method. For example, a method involving using synthetic mRNAs, nanoparticle-encapsulated synthetic mRNAs, or Sendai virus vectors may be utilized. Those methods can each introduce the mRNA or protein of a transcription factor into a pluripotent stem cell in a footprint-free manner. The details are as described below.

(Synthesis of mRNA Encoding Gene of Transcription Factor)

With reference to a method disclosed in the literature "Warren et al., Cell Stem Cell, 2010 Nov. 5; 7(5): 618-30," modified mRNA was synthesized. More specifically, mRNAs were synthesized by in vitro transcription using a mixture of dNTPs {(dNTPs: 3-0-Me-m7G (5') ppp (5') G ARCA cap analog, 5-methylcytidine triphosphate, and pseudouridine triphosphate)} obtained by modifying template DNAs encoding genes of transcription factors shown in FIGS. 3A-3D.

In order to express mammalian (in particular, human) transcription factors, Sendai vectors capable of expressing human transcription factors shown in FIGS. 3A-3D were used. In particular, mutants of Sendai virus vectors, such as F protein-deficient mutants, had no infectivity, and hence were easy to handle (see Inoue et al., J Virol. 77: 23238-3246, 2003).

(Method of Differentiating Pluripotent Stem Cell into Desired Cell Type)

With reference to the Z-values shown in FIGS. 4A-4T, a single transcription factor or a cocktail of two or more transcription factors was prepared. The form of the transcription factors is not particularly limited, and may be any of synthetic mRNAs, a Sendai virus vector having incorporated therein a transcription factor (or a plurality of transcription factors), and nanoparticle capsules containing synthetic mRNAs. The synthetic mRNA may carry, on the same gene, the gene sequences of a plurality of transcription factors.

A method of introducing the single transcription factor or cocktail of two or more transcription factors described above into cells is not particularly limited, and transfection with Lipofectamine, viral infection, or the like may be utilized.

Further, the type of cells (in particular, mammal cells, more preferably human cells) into which the single transcription factor or the cocktail of two or more transcription factors are introduced is not particularly limited, and encompasses pluripotent stem cells, such as embryonic stem cells (ESCs) and induced pluripotent stem cells (iPSCs), tissue stem cells derived from tissues and organs, dermal fibroblasts, and all kinds of cells derived from tissues and organs.

Figure 5:
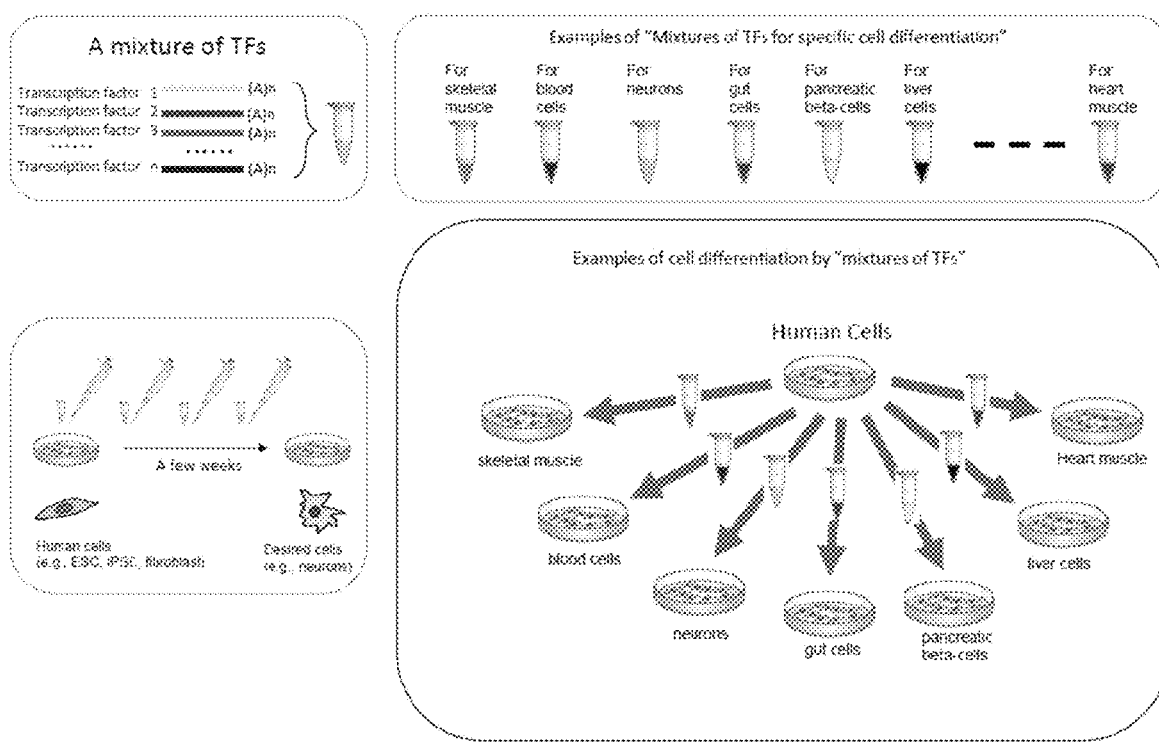
FIG. 5 is an illustration of a method of inducing differentiation into a desired cell type used in Examples of the present invention.

The outline of the steps of the method for differentiation into a desired cell type of this Example is illustrated in FIG. 5. Cells can be differentiated into the following desired cell types by introducing, into the cells, a transcription factor (or a transcription factor cocktail) selected from the human gene expression correlation matrix of Example 1 of the present invention by the method described in Example 2 of the present invention:

nerve cells (in particular, the fetal brain, the cerebellum peduncle, the cerebellum, the whole brain, the brain thalamus, the hypothalamus, the prefrontal cortex, the occipital lobe, the brain amygdala, the caudate nucleus, the cingulate cortex, the medulla oblongata, the globus pallidus, the subthalamic nucleus, the parietal lobe, the temporal lobe, or the pons), the pituitary, the olfactory nerve (in particular, the olfactory bulb), the spinal nerve (in particular, the spinal cord), skeletal muscles (in particular, the psoas or the tongue), the skin, ganglions (in particular, the dorsal root ganglion, the superior cervical ganglion, the atrioventricular node, the trigeminal ganglion, or the ciliary ganglion), the ovary, the adrenal gland (in particular, the adrenal cortex or the adrenal gland), the appendix, the kidney, the liver (in particular, the liver or the fetal liver), the salivary gland, the islet (in particular, islet cells), the pancreas, the prostate, the thymus (in particular, the thyroid or the fetal thyroid), adipocytes (in particular, cultured adipocytes), the uterus (in particular, the uterus or the uterus corpus), blood cells (in particular, whole blood, the bone marrow, monocytes, lymphnodes, the tonsil, the thymus, natural killer cells, dendritic cells, B cells, B_lymphoblasts, T cells (PB_CD8 or PB_CD4), or early erythroids), the bone marrow, hematopoietic stem cells, vascular endothelial cells, the testis (in particular, the testis, testis Leydig cells, testis germ cells, the testis seminiferous tubule, testis interstitial cells), the heart (in particular, the heart or cardiac myocytes), the placenta, smooth muscles, the lung (in particular, the lung, bronchial epithelial cells, the fetal lung, or the trachea), motor nerves, hepatoblasts/liver cells, and chondrocytes.

Example 3

(Differentiation into Nerve Cell)

In this Example, it was confirmed that human embryonic stem cells were able to be differentiated into nerve cells by introducing, into the human embryonic stem cells, a transcription factor cocktail selected from the human gene expression correlation matrix of Example 1 of the present invention by the method described in Example 2 of the present invention. The details are as described below.

(Method for Differentiation into Nerve Cell)

Figure 6A:
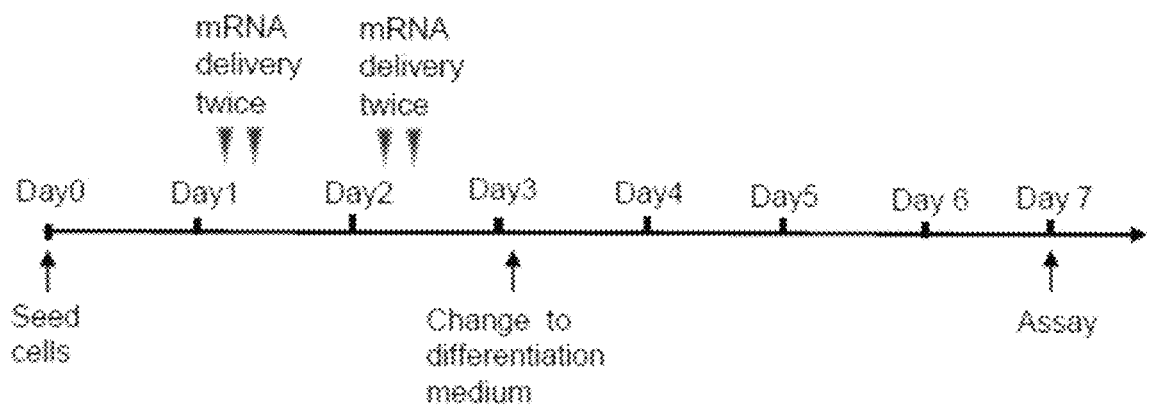
FIG. 6A is an illustration of a step of differentiating pluripotent stem cells into nerve cells.

With reference to the transcription factors and their Z-values shown in FIGS. 3A-3D and FIGS. 4A-4T, synthetic mRNAs of a cocktail of four transcription factors each having a Z-value of 12 or more (NEUROD1, NEUROD2, NEUROG2, and NEUROG3) were introduced (transfected) into human embryonic stem cells using RNAiMAX transfection reagent. The transfection was performed twice on day 1 and twice on day 2 (see FIG. 6A). On day 3, the medium was changed to a standard nerve cell differentiation medium, and cells on day 7 of the culture were harvested.

(Confirmation of Differentiation into Nerve Cell)

Figure 6B:
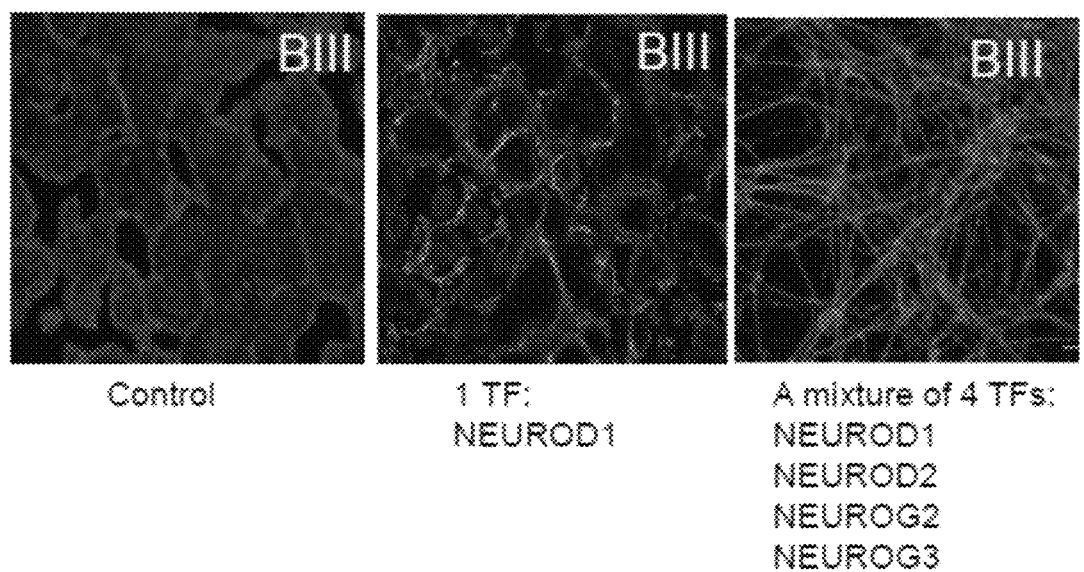
FIG. 6B is photographs of results for showing that pluripotent stem cells have been able to be differentiated into nerve cells.

The differentiation state of the cells was confirmed using a marker of mature nerve cells (beta-3-tubulin, BIII) (see FIG. 6B). Alone, NEUROD1 increased cells stained with BIII, but a nerve cell form was not clearly observed.

Meanwhile, the cocktail of four transcription factors increased not only the number of cells stained with BIII, but also the number of cells in the form of mature nerve cells.

Thus, it was confirmed that pluripotent stem cells were able to be differentiated into nerve cells by introducing, into the pluripotent stem cells, the transcription factor cocktail associated with differentiation into nerve cells, which had been selected from the human gene expression correlation matrix of Example 1 of the present invention.

Example 4

(Differentiation into Motor Nerve)

In this Example, it was confirmed that human embryonic stem cells were able to be differentiated into motor nerves by adding (introducing), into the human embryonic stem cells or the human induced pluripotent stem cells, a transcription factor cocktail selected from the human gene expression correlation matrix of Example 1 of the present invention by the method described in Example 2 of the present invention. The details are as described below.

With reference to the transcription factors and their Z-values shown in FIGS. 3A-3D and FIGS. 4A-4T, synthetic mRNAs of a cocktail of five transcription factors (NEUROD1, NEUROD2, NEUROG1, NEUROG2, and NEUROG3) were introduced (transfected) into human embryonic stem cells using RNAiMAX transfection reagent. The transfection was performed twice on day 1, followed by culture for 6 days in a standard nerve cell differentiation medium, and cells on day 7 of the culture were harvested.

Figure 7:
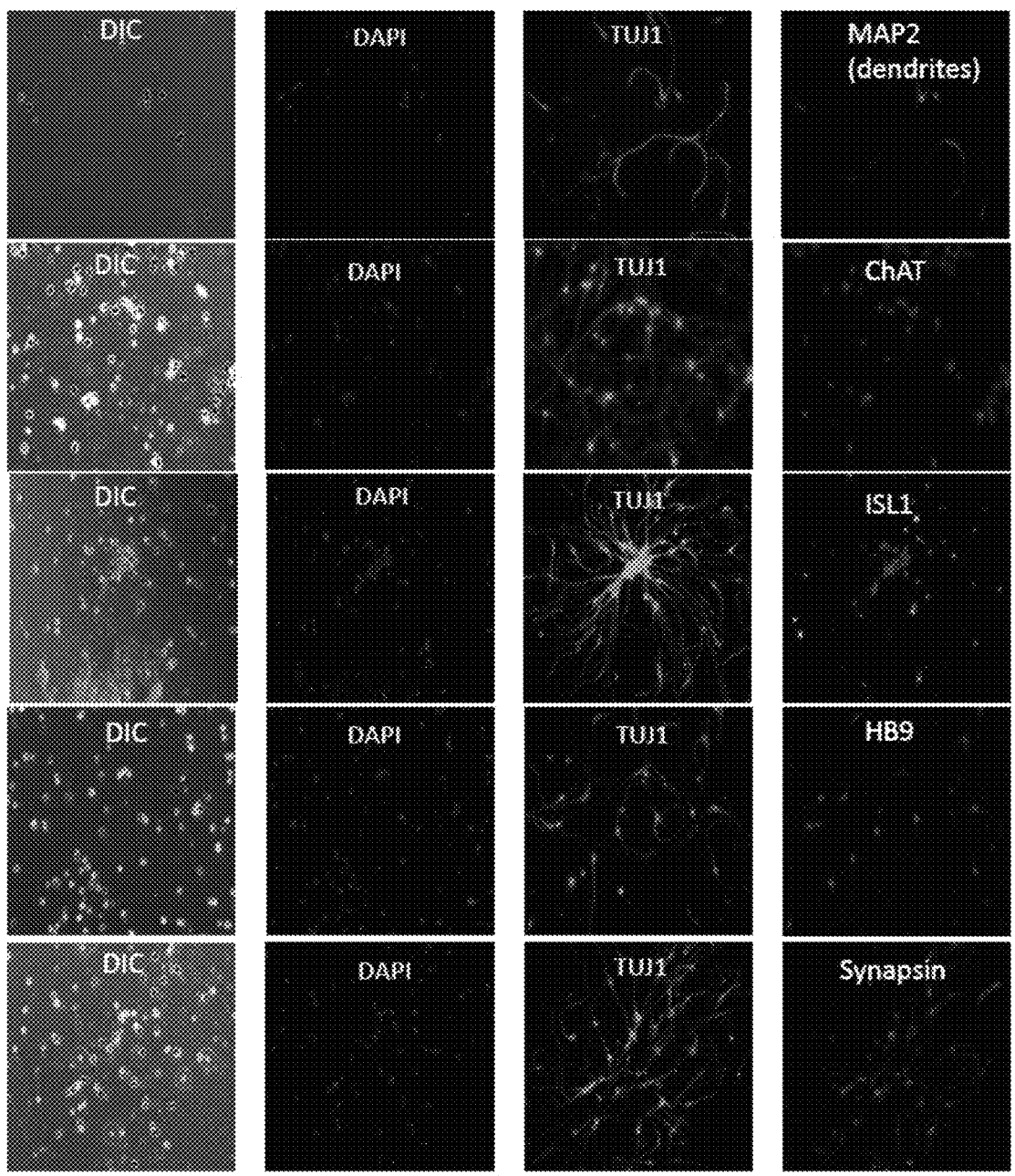
FIG. 7 is photographs of results for showing that human embryonic stem cells have been able to be differentiated into motor nerves.

The harvested cells were immunostained with a marker of nerve cells to confirm that the cells had differentiated into nerve cells (see FIG. 7). Further, electrophysiological analysis confirmed that those nerves were motor nerves on the basis of the expression of markers of choline-acetyl transferase (ChAT), ISL1, and HB9, and the like (see FIG. 7).

Culture conditions for differentiating human embryonic stem cells into nerve cells are already known. However, a related-art method generally takes from a few weeks to a month or more until a marker of nerve cells is expressed. Nonetheless, in this Example, it was confirmed that human embryonic stem cells were differentiated rapidly and highly efficiently by adding five kinds of synthetic mRNAs to the human embryonic stem cells.

Further, it was confirmed that the transfection was possible also by a method involving the first transfection with three kinds of transcription factors and the second transfection with two kinds of transcription factors.

Figure 8:
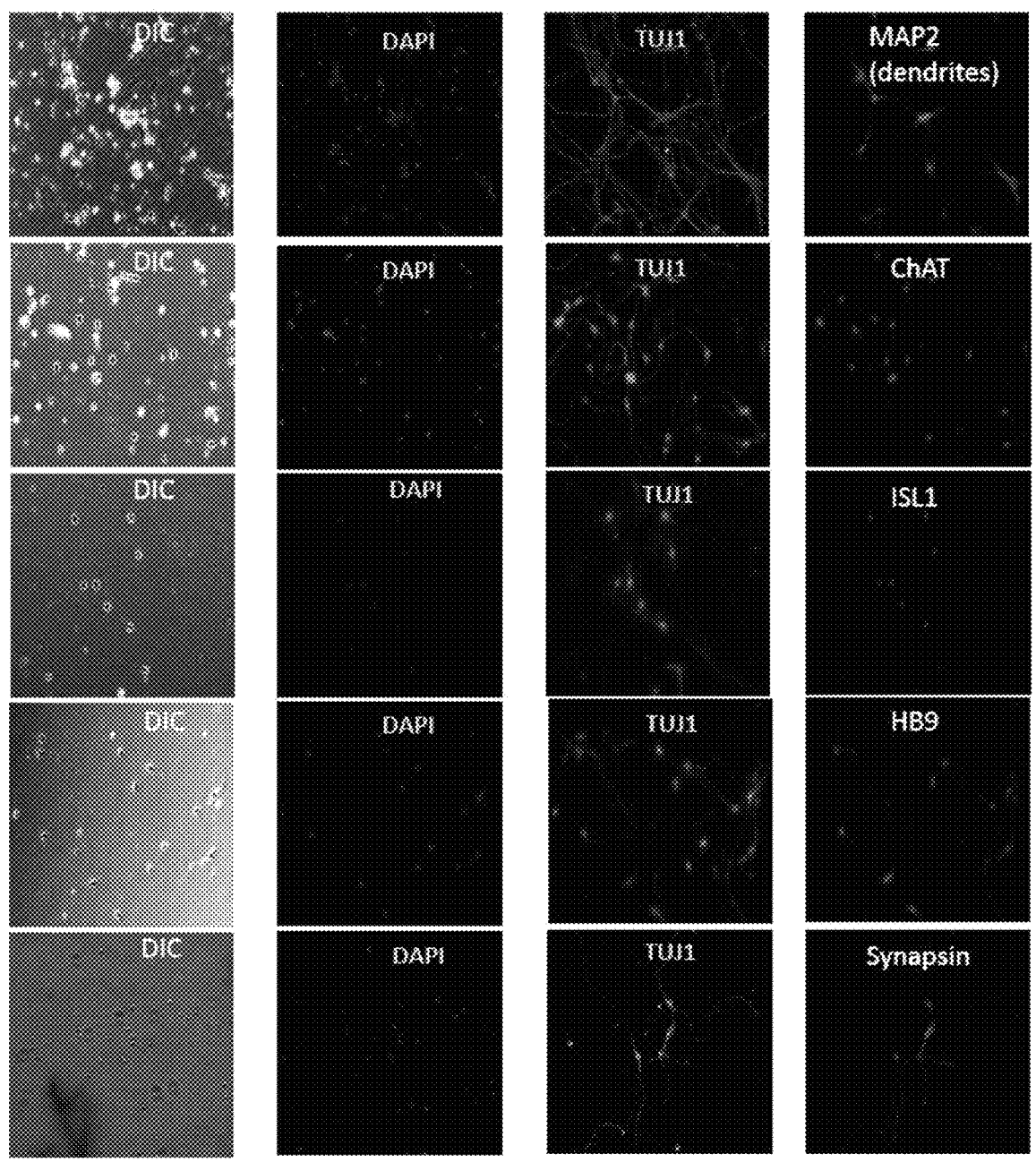
FIG. 8 is photographs of results for showing that human induced pluripotent stem cells have been able to be differentiated into motor nerves.

Human induced pluripotent stem cells were subjected to the same conditions as those for the human embryonic stem cells. The results for the human induced pluripotent stem cells confirmed rapid and highly efficient differentiation thereof as in the results for the human embryonic stem cells (see FIG. 8).

In this Example, it was confirmed for the first time that pluripotent stem cells were able to be differentiated into motor nerves (motor nerve cells, in particular, peripheral motor nerve cells).

Example 5

(Differentiation into Liver Cell)

In this Example, it was confirmed that human embryonic stem cells were able to be differentiated into liver cells/hepatoblasts by forcibly expressing, in the human embryonic stem cells, a transcription factor selected from the human gene expression correlation matrix of Example 1 of the present invention by the method described in Example 1 of the present invention. The details are as described below.

With reference to the transcription factors and their Z-values shown in FIGS. 3A-3D and FIGS. 4A-4T, each transcription factor (TGIF, TCF4, PITX2, SALL4, or MEIS1) was selected. Through addition of doxycycline to human embryonic stem cells having introduced therein those transcription factors as Transgene to be induced by doxycycline, those transcription factors were forcibly expressed in human embryonic stem cells. The forced expression was performed for 24 hours on day 1, followed by culture for 8 days in a known liver cell differentiation medium, and cells on day 9 of the culture were harvested.

Figure 9:
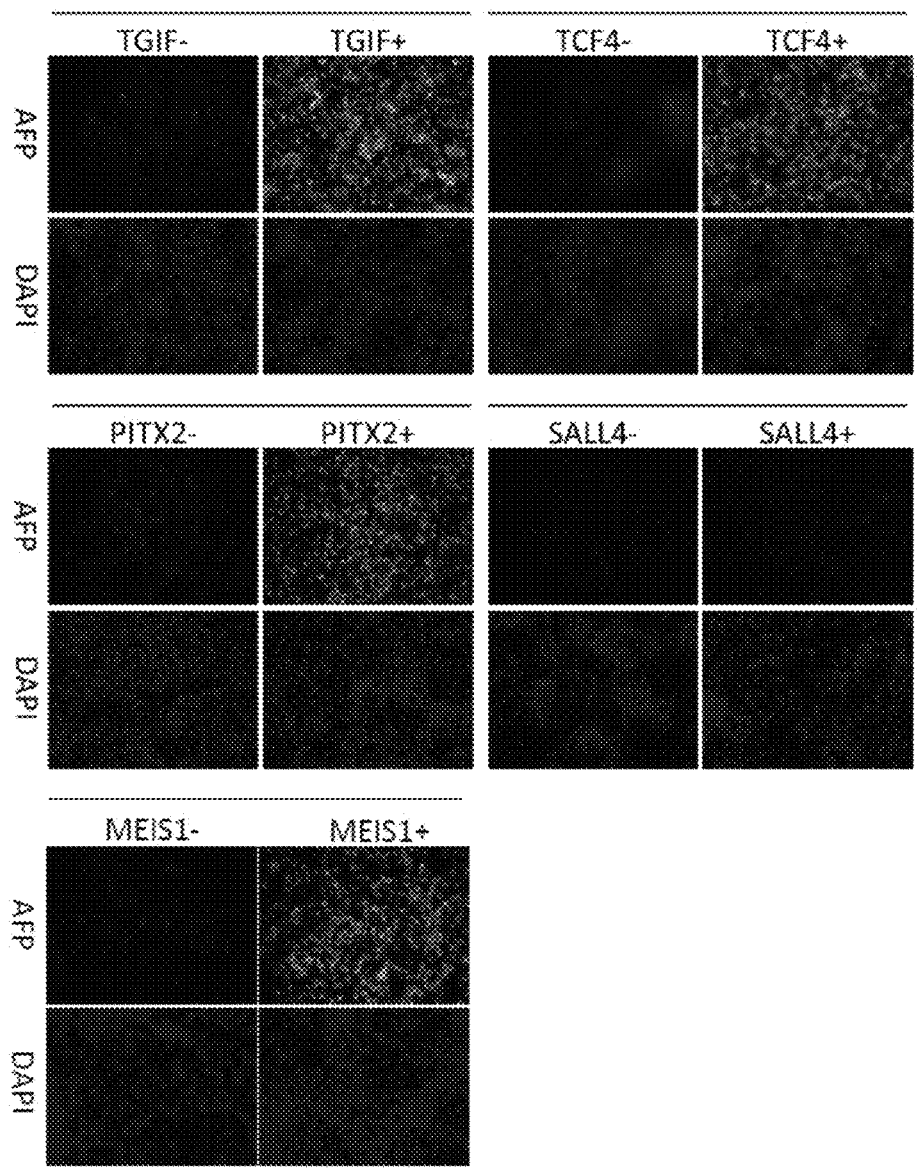
FIG. 9 is photographs of results for showing that pluripotent stem cells have been able to be differentiated into hepatoblasts/liver cells.

On the basis of the expression of albumin serving as a marker of liver cells, differentiation into liver cells/hepatoblasts was confirmed (see FIG. 9). In FIG. 9, "TGIF−, TCF4−, PITX2−, SALL4−, and MEIS1−" mean control groups having introduced therein no transcription factor.

Culture conditions for differentiating human embryonic stem cells into liver cells are already known. Such culture conditions are disclosed in, for example, Hay D C, et al. (2008), Stem Cells 26: 894-902. In addition, in the report by Kajiwara et al. (2012) {Proc Natl Acad Sci USA. 109: 12538-43}, it is reported that, when various cell growth and differentiation factors are progressively added into medium, the expression of albumin serving as a marker of hepatic cells starts on day 17. However, in this Example, under the same culture conditions, the expression of albumin was able to be confirmed on day 9 of the culture. In other words, the culture time was able to be shortened by about a half. In addition, the method disclosed in the literature requires the addition of a liver cell-specific differentiation factor HGF and the like on day 10 and thereafter. However, the addition was not required in this Example.

In consideration of the foregoing, the differentiation into liver cells of the present invention has the remarkable effect of rapid differentiation and the qualitatively different effect of not requiring the addition of the liver cell-specific differentiation factor HGF as compared to the related-art method.

Further, in this Example, the differentiation was able to be caused by introducing each one of the five transcription factors, but a method involving transfecting five, four, three, or two of the transcription factors simultaneously or separately is also possible.

Example 6

(Differentiation into Hematopoietic Stem Cell/Blood Cell)

In this Example, it was confirmed that human embryonic stem cells were able to be differentiated into hematopoietic stem cells/blood cells by forcibly expressing, in the human embryonic stem cells, a transcription factor selected from the human gene expression correlation matrix of Example 1 of the present invention by the method described in Example 1 of the present invention. The details are as described below.

With reference to the transcription factors and their Z-values shown in FIGS. 3A-3D and FIGS. 4A-4T, each transcription factor (CDYL2, ETS2, SPI1, OVOL2, CDX2, CEBPB, or SALL4) was selected. Through addition of doxycycline to human embryonic stem cells having introduced therein those transcription factors as Transgene to be induced by doxycycline, those transcription factors were forcibly expressed in human embryonic stem cells. The forced expression was performed for 48 hours on from day 3 to day 5 of the culture, followed by culture in a known hematopoietic progenitor cell medium, and cells on day 5 of the culture were harvested.

Culture conditions for differentiating human ES cells into hematopoietic progenitor cells are already known. Such culture conditions are disclosed in, for example, the literature Wang et al. (2012) Cell Res. 22:194-207. In the literature, it is reported that, when various cell growth and differentiation factors are progressively added into a medium, the expression of CD43 serving as a marker of hematopoietic progenitor cells starts on day 17.

Figure 10:
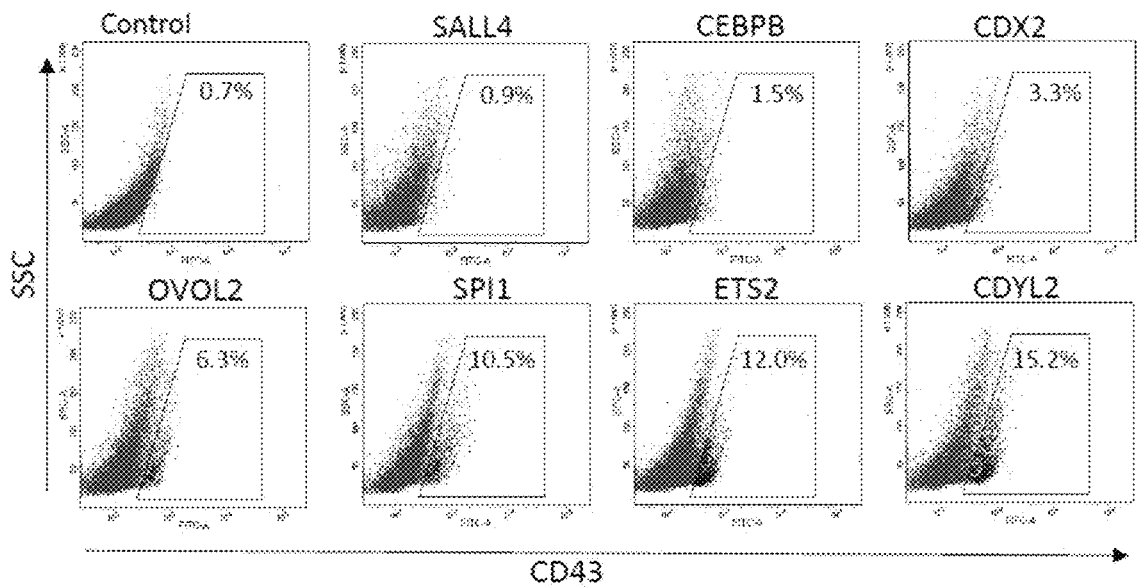
FIG. 10 is graphs of results for showing that pluripotent stem cells have been able to be differentiated into hematopoietic stem cells/blood cells.

However, in this Example, it was found that forced expression (induced with DOX) of a transcription factor under known hematopoietic progenitor cell conditions remarkably increased the speed and efficiency of the differentiation into hematopoietic progenitor cells. Irrespective of whether the transcription factors were used alone or in combination thereof, the transcription factors were able to cause the differentiation. More specifically, in this Example, the expression of CD43 serving as a marker of hematopoietic progenitor cells was confirmed on day 5 of the culture (see FIG. 10). On day 5, in the control group (related art) having introduced therein no transcription factor, the expression of CD43 was hardly recognized. Thus, the method of the present invention has an about 4-fold differentiation-inducing ability (differentiation speed) as compared to the related-art method.

Example 7

(Differentiation into Chondrocyte)

In this Example, it was confirmed that human embryonic stem cells were able to be differentiated into chondrocytes by forcibly expressing, in the human embryonic stem cells, a transcription factor selected from the human gene expression correlation matrix of Example 1 of the present invention by the method described in Example 1 of the present invention. The details are as described below.

With reference to the transcription factors and their Z-values shown in FIGS. 3A-3D and FIGS. 4A-4T, SOX9 was selected. Through addition of doxycycline to human embryonic stem cells having introduced therein SOX9 as Transgene to be induced by doxycycline, SOX9 was forcibly expressed in human embryonic stem cells. The forced expression was performed for 24 hours on day 1, followed by culture for 2 days in a known human embryonic stem cell culture medium, and cells on day 3 of the culture were harvested.

Culture conditions for differentiating human embryonic stem cells into chondrocytes are already known. Such culture conditions are disclosed in, for example, the literature Oldershaw et al. (2010). Nat Biotechnol. 28:1187-94. In the literature, type II collagen-positive chondrocytes are produced on 14th day after differentiation induction in such a complicated manner that various cell growth and differentiation factors are progressively added in stages into a medium.

Figure 11:
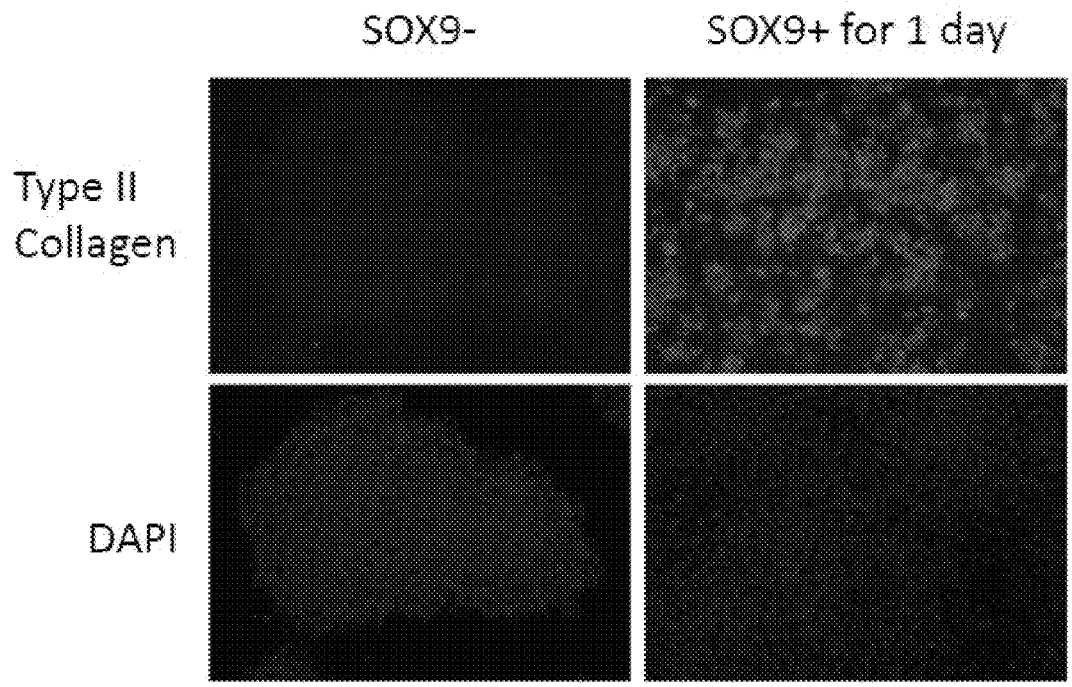
FIG. 11 is photographs of results for showing that pluripotent stem cells have been able to be differentiated into chondrocytes.

However, in this Example, it was confirmed that, as a result of forced expression of SOX9, type II collagen-positive chondrocytes were able to be produced 2 days after the forced expression (i.e., on the 3rd day after differentiation induction) (see "SOX9+ for 1 day" of FIG. 11). In this Example, the differentiation-promoting medium used in the literature was not used, and a general embryonic stem cell culture medium was used. In the control to which SOX9 had not been added (see "SOX9−" of FIG. 11), the expression of type II collagen was not able to be confirmed.

As can be seen from the above, the differentiation method of the present invention does not use any special medium, and the method of the present invention has an about 4-fold differentiation-inducing ability (differentiation speed) as compared to the related-art method.

Example 8

(Differentiation into Nerve Cell)

In this Example, a human embryonic stem cell can be differentiated into a nerve cell by introducing, into the human embryonic stem cell, a transcription factor cocktail selected from the human gene expression correlation matrix of Example 1 of the present invention by the method described in Example 2 of the present invention.

A method for differentiation into the nerve cell (in particular, a cell present in the fetal brain, the cerebellum peduncle, the cerebellum, the whole brain, the brain thalamus, the hypothalamus, the prefrontal cortex, the occipital lobe, the brain amygdala, the caudate nucleus, the cingulate cortex, the medulla oblongata, the globus pallidus, the subthalamic nucleus, the parietal lobe, the temporal lobe, or the pons) of the present invention is as described below.

Fetal brain: NEUROG2, NEUROG1, NEUROG3, SOX11, MXI1, PDX1, NEUROD2, HOXA2, and NEUROD1 are introduced into a human pluripotent stem cell.

Cerebellum peduncle: NEUROG2, NEUROG3, NEUROG1, NEUROD1, NRF1, ASCL1, HOXA2, PITX2, and NEUROD2 are introduced into a human pluripotent stem cell.

Cerebellum: NEUROG2, NEUROG3, NEUROG1, NEUROD1, NRF1, HOXA2, ASCL1, PITX2, NEUROD2, PRDM1, and NFIB are introduced into a human pluripotent stem cell.

Whole brain: NEUROG2, NEUROG3, NEUROG1, NEUROD1, NRF1, and HOXA2 are introduced into a human pluripotent stem cell.

Brain thalamus: NEUROG2, NEUROG3, HOXA2, NEUROG1, and ASCL1 are introduced into a human pluripotent stem cell.

Hypothalamus: NEUROG2, SOX2, NEUROG1, NEUROG3, HOXA2, and SOX11 are introduced into a human pluripotent stem cell.

Prefrontal cortex: NEUROG2, NEUROG3, NEUROG1, SOX11, MXI1, SOX2, HOXA2, PDX1, ASCL1, NEUROD1, and NEUROD2 are introduced into a human pluripotent stem cell.

Occipital lobe: NEUROG2, NEUROG1, NEUROG3, HOXA2, SOX2, SOX11, PDX1, NEUROD1, ASCL1, and MXI1 are introduced into a human pluripotent stem cell.

Brain amygdala: NEUROG2, NEUROG1, NEUROG3, HOXA2, SOX2, PDX1, SOX11, MXI1, NEUROD1, and ASCL1 are introduced into a human pluripotent stem cell.

Caudate nucleus: NEUROG2, HOXA2, NEUROG1, NEUROG3, SOX2, NRF1, ASCL1, and PDX1 are introduced into a human pluripotent stem cell.

Cingulate cortex: NEUROG2, NEUROG3, NEUROG1, HOXA2, ASCL1, SOX11, PDX1, NRF1, NEUROD1, and PRDM1 are introduced into a human pluripotent stem cell.

Medulla oblongata: NEUROG2, HOXA2, NEUROG1, NEUROG3, PDX1, SOX11, SOX2, NRF1, ASCL1, NR2F2, and GLIS2 are introduced into a human pluripotent stem cell.

Globus pallidus: NEUROG2, HOXA2, NEUROG1, NEUROG3, NRF1, ASCL1, SOX11, and PDX1 are introduced into a human pluripotent stem cell.

Subthalamic nucleus: NEUROG2, HOXA2, NEUROG1, NEUROG3, NRF1, ASCL1, SOX11, and PDX1 are introduced into a human pluripotent stem cell.

Parietal lobe: NEUROG2, HOXA2, NEUROG3, NEUROG1, NRF1, SOX11, ASCL1, PDX1, and SOX2 are introduced into a human pluripotent stem cell.

Temporal lobe: NEUROG2, HOXA2, NRF1, NEUROG1, and NEUROG3 are introduced into a human pluripotent stem cell.

Pons: HOXA2, NRF1, NEUROG2, NEUROG1, NEUROG3, CTCF, NR2F2, HES1, NFIC, PDX1, SOX11, and ERG are introduced into a human pluripotent stem cell.

Example 9

(Differentiation into Pituitary)

In this Example, a human embryonic stem cell can be differentiated into the pituitary, in particular, a cell present in the pituitary by introducing, into the human embryonic stem cell, a transcription factor cocktail selected from the human gene expression correlation matrix of Example 1 of the present invention by the method described in Example 2 of the present invention.

A method for differentiation into the pituitary of the present invention is as described below.

SOX2, NANOG, ASCL1, DLX4, DLX3, and CDX2 are introduced into a human pluripotent stem cell.

Example 10

(Differentiation into Olfactory Nerve)

In this Example, a human embryonic stem cell can be differentiated into the olfactory nerve, in particular, a cell present in the olfactory nerve by introducing, into the human embryonic stem cell, a transcription factor cocktail selected from the human gene expression correlation matrix of Example 1 of the present invention by the method described in Example 2 of the present invention.

A method for differentiation into the olfactory nerve (in particular, the olfactory bulb) of the present invention is as described below.

Olfactory bulb: NFIB, TBX2, TBX3, SOX2, NFIC, HES1, JUNB, FOS, and FOXA2 are introduced into a human pluripotent stem cell.

Example 11

(Differentiation into Spinal Nerve)

In this Example, a human embryonic stem cell can be differentiated into the spinal nerve, in particular, a cell present in the spinal nerve by introducing, into the human embryonic stem cell, a transcription factor cocktail selected from the human gene expression correlation matrix of Example 1 of the present invention by the method described in Example 2 of the present invention.

A method for differentiation into the spinal nerve (in particular, the spinal cord) of the present invention is as described below.

Spinal cord: NFIB, SOX2, HOXA2, TBX3, and E2F6 are introduced into a human pluripotent stem cell.

Example 12

(Differentiation into Skeletal Muscle)

In this Example, a human embryonic stem cell can be differentiated into a skeletal muscle, in particular, a cell present in the skeletal muscle by introducing, into the human embryonic stem cell, a transcription factor cocktail selected from the human gene expression correlation matrix of Example 1 of the present invention by the method described in Example 2 of the present invention.

A method for differentiation into the skeletal muscle (in particular, the psoas or the tongue) of the present invention is as described below.

Psoas: MYOD1, NRF1, SALL4, ZIC1, KLF9, ZNF281, CTCF, HES1, HOXA2, TBX5, TP73, ERG, MAB21L3, PRDM1, NFIC, CTCFL, FOXP1, HEY1, and PITX2 are introduced into a human pluripotent stem cell.

Tongue: MYOD1, TP73, HES1, JUNB, KLF4, SALL4, ZIC1, ESX1, ZNF281, TBX5, NRF1, HEY1, TFAP2C, FOS, FOXP1, TFE3, CTCF, FOSL1, GRHL2, TBX2, NFIB, PITX2, KLF9, and IRF4 are introduced into a human pluripotent stem cell.

Example 13

(Differentiation into Skin)

In this Example, a human embryonic stem cell can be differentiated into the skin, in particular, a cell present in the skin by introducing, into the human embryonic stem cell, a transcription factor cocktail selected from the human gene expression correlation matrix of Example 1 of the present invention by the method described in Example 2 of the present invention.

A method for differentiation into the skin of the present invention is as described below.

HES1, CTCF, TP73, JUNB, HEY1, ZIC1, TBX5, NFIC, TFAP2C, ESX1, NRF1, HOXA2, ELF1, NR2F2, KLF9, GRHL2, IRF4, ERG, FOS, TBX2, SALL4, and KLF4 are introduced into a human pluripotent stem cell.

Example 14

(Differentiation into Ganglion)

In this Example, a human embryonic stem cell can be differentiated into a ganglion, in particular, a cell present in the ganglion by introducing, into the human embryonic stem cell, a transcription factor cocktail selected from the human gene expression correlation matrix of Example 1 of the present invention by the method described in Example 2 of the present invention.

A method for differentiation into the ganglion (in particular, the dorsal root ganglion, the superior cervical ganglion, the atrioventricular node, the trigeminal ganglion, or the ciliary ganglion) of the present invention is as described below.

Dorsal root ganglion: HES1, HOXA2, CTCF, TBX2, NR2F2, NRF1, HEY1, NFIC, TBX3, JUNB, TBX5, E2F6, GLIS2, ZIC1, ERG, and KLF9 are introduced into a human pluripotent stem cell.

Superior cervical ganglion: HES1, CTCF, NRF1, HOXA2, HEY1, NFIC, NR2F2, TBX5, KLF9, ZIC1, ERG, FLI1, TBX2, JUNB, ELF1, GLIS2, TBX3, TFAP4, IRF4, and PDX1 are introduced into a human pluripotent stem cell.

Atrioventricular node: HES1, CTCF, NRF1, HEY1, HOXA2, NFIC, NR2F2, ZIC1, TBX5, KLF9, TBX2, ERG, JUNB, TFAP2C, ELF1, TP73, TFAP4, ESX1, E2F6, IRF4, FLI1, SALL4, TBX3, and ARNT2 are introduced into a human pluripotent stem cell.

Trigeminal ganglion: HES1, CTCF, HOXA2, HEY1, NRF1, NR2F2, NFIC, TBX5, JUNB, ZIC1, TBX2, KLF9, ERG, ELF1, TBX3, E2F6, ESX1, ARNT2, GLIS2, TP73, and IRF4 are introduced into a human pluripotent stem cell.

Ciliary ganglion: HES1, CTCF, HEY1, NFIC, JUNB, HOXA2, NRF1, NR2F2, TBX2, ZIC1, TBX5, NFIB, ARNT2, ESX1, IRF4, ERG, TBX3, TFAP2C, ELF1, FOS, TP73, HSF1, KLF9, GLIS2, E2F6, PITX2, ZNF281, FOSL1, IRF1, FOXP1, and GATA3 are introduced into a human pluripotent stem cell.

Example 15

(Differentiation into Ovary)

In this Example, a human embryonic stem cell can be differentiated into the ovary, in particular, a cell present in the ovary by introducing, into the human embryonic stem cell, a transcription factor cocktail selected from the human gene expression correlation matrix of Example 1 of the present invention by the method described in Example 2 of the present invention.

A method for differentiation into the ovary of the present invention is as described below.

HES1, HEY1, CTCF, NR2F2, NFIC, TBX2, TBX3, NRF1, ZIC1, HOXA2, TBX5, JUNB, and ERG are introduced into a human pluripotent stem cell.

Example 16

(Differentiation into Adrenal Gland)

In this Example, a human embryonic stem cell can be differentiated into the adrenal gland, in particular, a cell present in the adrenal gland by introducing, into the human embryonic stem cell, a transcription factor cocktail selected from the human gene expression correlation matrix of Example 1 of the present invention by the method described in Example 2 of the present invention.

A method for differentiation into the adrenal gland (in particular, the adrenal cortex or the adrenal gland) of the present invention is as described below.

Adrenal cortex: SALL4, HES1, HEY1, ZIC1, FOXP1, ESX1, PITX2, NRF1, TP73, JUNB, DLX6, and TGIF1 are introduced into a human pluripotent stem cell.

Adrenal gland: TGIF1, SALL4, TFE3, NFIB, ZIC1, and DLX6 are introduced into a human pluripotent stem cell.

Example 17

(Differentiation into Appendix)

In this Example, a human embryonic stem cell can be differentiated into the appendix, in particular, a cell present in the appendix by introducing, into the human embryonic stem cell, a transcription factor cocktail selected from the human gene expression correlation matrix of Example 1 of the present invention by the method described in Example 2 of the present invention.

A method for differentiation into the appendix of the present invention is as described below.

HES1, CTCF, NR2F2, HEY1, HOXA2, NFIC, TBX2, NRF1, JUNB, TBX5, ZIC1, ERG, GLIS2, KLF9, ELF1, TBX3, IRF4, ARNT2, E2F6, IRF1, HSF1, SOX2, TFAP2C, TFAP4, FLI1, PDX1, RUNX3, MYOD1, HNF1A, NFIB, ESX1, and TP73 are introduced into a human pluripotent stem cell.

Example 18

(Differentiation into Kidney)

In this Example, a human embryonic stem cell can be differentiated into the kidney, in particular, a cell present in the kidney by introducing, into the human embryonic stem cell, a transcription factor cocktail selected from the human gene expression correlation matrix of Example 1 of the present invention by the method described in Example 2 of the present invention.

A method for differentiation into the kidney of the present invention is as described below.

HNF4A, SALL4, TGIF1, HNF1A, ZIC1, NFIB, TFE3, TP73, TFAP2C, NRF1, SMAD7, and MAB21L3 are introduced into a human pluripotent stem cell.

Example 19

(Differentiation into Liver)

In this Example, a human embryonic stem cell can be differentiated into the liver, in particular, a cell present in the liver by introducing, into the human embryonic stem cell, a transcription factor cocktail selected from the human gene expression correlation matrix of Example 1 of the present invention by the method described in Example 2 of the present invention.

A method for differentiation into the liver (in particular, the liver or the fetal liver) of the present invention is as described below.

Liver: SALL4, TGIF1, MAB21L3, ZIC1, EGFLAM, PITX2, HNF4A, NRF1, ZNF281, CTCFL, TP73, TFE3, DLX6, and TCF4 are introduced into a human pluripotent stem cell.

Fetal liver: SIX5, HNF4A, SIN3A, ID1, and HNF1A are introduced into a human pluripotent stem cell.

Example 20

(Differentiation into Salivary Gland)

In this Example, a human embryonic stem cell can be differentiated into the salivary gland, in particular, a cell present in the salivary gland by introducing, into the human embryonic stem cell, a transcription factor cocktail selected from the human gene expression correlation matrix of Example 1 of the present invention by the method described in Example 2 of the present invention.

A method for differentiation into the salivary gland of the present invention is as described below.

HES1, HEY1, ELF1, CTCF, and FLI1 are introduced into a human pluripotent stem cell.

Example 21

(Differentiation into Islet)

In this Example, a human embryonic stem cell can be differentiated into the islet, in particular, a cell present in the islet by introducing, into the human embryonic stem cell, a transcription factor cocktail selected from the human gene expression correlation matrix of Example 1 of the present invention by the method described in Example 2 of the present invention.

A method for differentiation into the islet (in particular, an islet cell) of the present invention is as described below.

ASCL1, CEBPB, HES1, JUNB, and TFE3 are introduced into a human pluripotent stem cell.

Example 22

(Differentiation into Pancreas)

In this Example, a human embryonic stem cell can be differentiated into the pancreas, in particular, a cell present in the pancreas by introducing, into the human embryonic stem cell, a transcription factor cocktail selected from the human gene expression correlation matrix of Example 1 of the present invention by the method described in Example 2 of the present invention.

A method for differentiation into the pancreas of the present invention is as described below.

HNF4A, ELF1, ZIC1, SALL4, and JUNB are introduced into a human pluripotent stem cell.

Example 23

(Differentiation into Prostate)

In this Example, a human embryonic stem cell can be differentiated into the prostate, in particular, a cell present in the prostate by introducing, into the human embryonic stem cell, a transcription factor cocktail selected from the human gene expression correlation matrix of Example 1 of the present invention by the method described in Example 2 of the present invention.

A method for differentiation into the prostate of the present invention is as described below.

NFIB, TP73, FOS, IRF5, ESRRB, TFAP2C, GRHL2, HHEX, HOXA9, DLX6, ESX1, TGIF1, SALL4, CEBPB, and JUNB are introduced into a human pluripotent stem cell.

Example 24

(Differentiation into Thyroid)

In this Example, a human embryonic stem cell can be differentiated into the thymus, in particular, a cell present in the thymus by introducing, into the human embryonic stem cell, a transcription factor cocktail selected from the human gene expression correlation matrix of Example 1 of the present invention by the method described in Example 2 of the present invention.

A method for differentiation into the thyroid thymus (in particular, the thyroid or the fetal thyroid) of the present invention is as described below.

Thyroid: MYOD1, NFIB, HHEX, ASCL2, and PPARG are introduced into a human pluripotent stem cell.

Fetal thyroid: NFIB, MYOD1, HHEX, TGIF1, and TFAP2C are introduced into a human pluripotent stem cell.

Example 25

(Differentiation into Adipocyte)

In this Example, a human embryonic stem cell can be differentiated into an adipocyte by introducing, into the human embryonic stem cell, a transcription factor cocktail selected from the human gene expression correlation matrix of Example 1 of the present invention by the method described in Example 2 of the present invention.

A method for differentiation into the adipocyte (in particular, a cultured adipocyte) of the present invention is as described below.

Cultured adipocyte: JUN, NFIB, FOSL1, FOS, JUNB, and SREBF2 are introduced into a human pluripotent stem cell.

Example 26

(Differentiation into Uterus)

In this Example, a human embryonic stem cell can be differentiated into the uterus, in particular, a cell present in the uterus by introducing, into the human embryonic stem cell, a transcription factor cocktail selected from the human gene expression correlation matrix of Example 1 of the present invention by the method described in Example 2 of the present invention.

A method for differentiation into the uterus (in particular, the uterus or the uterus corpus) of the present invention is as described below.

Uterus: NFIB, JUN, FOSL1, SOX2, RUNX3, NFIC, JUNB, IRF5, PTF1A, HSF1, TBX2, TBX3, FOS, MEF2C, ARNT2, and GATA2 are introduced into a human pluripotent stem cell.

Uterus corpus: HES1, JUNB, CTCF, HEY1, FOS, ZIC1, HOXA2, NFIC, FOSL1, NRF1, TBX5, ARNT2, NFIB, TFAP2C, ESX1, TBX2, TBX3, NR2F2, TP73, IRF4, THAP11, ELF1, JUN, ERG, HSF1, and KLF9 are introduced into a human pluripotent stem cell.

Example 27

(Differentiation into Blood Cell)

In this Example, a human embryonic stem cell can be differentiated into a blood cell, into the human embryonic stem cell, a transcription factor cocktail selected from the human gene expression correlation matrix of Example 1 of the present invention by the method described in Example 2 of the present invention.

A method for differentiation into the blood cell (in particular, whole blood, the bone marrow, a monocyte, a lymphnode, the tonsil, the thymus, a natural killer cell, a dendritic cell, a B cell, a B lymphoblast, a T cell (PB_CD8 or PB_CD4), or an early erythroid) of the present invention is as described below.

Whole blood: CEBPB, SPI1, ETS1, ELF1, IRF1, ETS2, IRF2, DMRT1, and KLF4 are introduced into a human pluripotent stem cell.

Bone marrow: SALL4, CEBPB, ESX1, ELF1, ZIC1, ZNF281, ETS1, KLF4, FOXP1, NRF1, and SPI1 are introduced into a human pluripotent stem cell.

Bone marrow: CEBPB, SPI1, ETS1, ELF1, CDYL2, IRF1, and GADD45A are introduced into a human pluripotent stem cell.

Monocyte: SPI1, CEBPB, ETS1, ELF1, IRF1, CDYL2, and GADD45A are introduced into a human pluripotent stem cell.

Lymphnode: IRF1, IRF2, ELF1, ETS1, SPI1, ETS2, IRF4, and RUNX3 are introduced into a human pluripotent stem cell.

Tonsil: ELF1, SPI1, IRF1, IRF2, ESX1, IRF4, KLF4, SALL4, and ETS1 are introduced into a human pluripotent stem cell.

Thymus: SALL4, ESX1, ETS1, SPI1, and ETS2 are introduced into a human pluripotent stem cell.

Natural killer cell: ETS1, CDYL2, GADD45A, IRF1, and IRF2 are introduced into a human pluripotent stem cell.

Dendritic cell: CDYL2, SPI1, GADD45A, ETS1, and MYC are introduced into a human pluripotent stem cell.

B cell: CDYL2, MYC, ATF2, IRF2, and GBX2 are introduced into a human pluripotent stem cell.

B lymphoblast: MYC, CDYL2, GADD45A, GBX2, ATF2, RUVBL2, PLXNB3, L3MBTL2, E2F4, SMARCA4, ID1, and ZSCAN4 are introduced into a human pluripotent stem cell.

T cell (PB_CD8): CDYL2, MYC, GBX2, ETS1, and IRF2 are introduced into a human pluripotent stem cell.

T cell (PB_CD4): CDYL2, MYC, GBX2, ETS1, and ATF2 are introduced into a human pluripotent stem cell.

Early erythroid: CDYL2, E2F4, GADD45A, and ZSCAN4 are introduced into a human pluripotent stem cell.

Example 28

(Differentiation into Bone Marrow)

In this Example, a human embryonic stem cell can be differentiated into the bone marrow, in particular, a cell present in the bone marrow by introducing, into the human embryonic stem cell, a transcription factor cocktail selected from the human gene expression correlation matrix of Example 1 of the present invention by the method described in Example 2 of the present invention.

A method for differentiation into the bone marrow of the present invention is as described below.

SALL4, CEBPB, ESX1, ELF1, ZIC1, ZNF281, ETS1, KLF4, FOXP1, NRF1, and SPI1 are introduced into a human pluripotent stem cell.

Example 29

(Differentiation into Hematopoietic Stem Cell)

In this Example, a human embryonic stem cell can be differentiated into a hematopoietic stem cell by introducing, into the human embryonic stem cell, a transcription factor cocktail selected from the human gene expression correlation matrix of Example 1 of the present invention by the method described in Example 2 of the present invention.

A method for differentiation into the hematopoietic stem cell of the present invention is as described below.

MYC, GBX2, CDYL2, GADD45A, ATF2, ID1, ZSCAN4, SMARCA4, E2F4, and RUVBL2 are introduced into a human pluripotent stem cell.

Example 30

(Differentiation into Vascular Endothelial Cell)

In this Example, a human embryonic stem cell can be differentiated into a vascular endothelial cell by introducing, into the human embryonic stem cell, a transcription factor cocktail selected from the human gene expression correlation matrix of Example 1 of the present invention by the method described in Example 2 of the present invention.

A method for differentiation into the vascular endothelial cell of the present invention is as described below.

MYC, RUVBL2, GBX2, CDYL2, GADD45A, ATF2, ID1, and E2F4 are introduced into a human pluripotent stem cell.

Example 31

(Differentiation into Testis)

In this Example, a human embryonic stem cell can be differentiated into the testis, in particular, a cell present in the testis by introducing, into the human embryonic stem cell, a transcription factor cocktail selected from the human gene expression correlation matrix of Example 1 of the present invention by the method described in Example 2 of the present invention.

A method for differentiation into the testis (in particular, the testis, a testis Leydig cell, a testis germ cell, the testis seminiferous tubule, or a testis interstitial cell) of the present invention is as described below.

Testis: SALL4, MYBL2, RFX2, TGIF1, and CTCFL are introduced into a human pluripotent stem cell.

Testis Leydig cell: MYBL2, NR2F2, KLF9, GLIS2, and SIX5 are introduced into a human pluripotent stem cell.

Testis germ cell: MYBL2, L3MBTL2, E2F4, KDM5A, and DMRT1 are introduced into a human pluripotent stem cell.

Testis seminiferous tubule: MYBL2, E2F4, KLF9, YY1, and NEUROD1 are introduced into a human pluripotent stem cell.

Testis interstitial cell: MYBL2, E2F4, NR2F2, KLF9, and GTF2F1 are introduced into a human pluripotent stem cell.

Example 32

(Differentiation into Heart)

In this Example, a human embryonic stem cell can be differentiated into the heart, in particular, a cell present in the heart by introducing, into the human embryonic stem cell, a transcription factor cocktail selected from the human gene expression correlation matrix of Example 1 of the present invention by the method described in Example 2 of the present invention.

A method for differentiation into the heart (in particular, the heart or a cardiac myocyte) of the present invention is as described below.

Heart: SALL4, TGIF1, PITX2, ZNF281, NRF1, ZIC1, TP73, FOXP1, CTCFL, NFIB, TFE3, EGFLAM, DLX6, TFAP2C, MYOD1, ESX1, PRDM1, MAB21L3, FOS, TCF4, JUNB, SMAD7, KLF4, ARID3A, TBX5, HOXA9, HES1, FOXG1, FOSL2, USF2, ERG, and ARNT2 are introduced into a human pluripotent stem cell.

Cardiac myocyte: FOSL1, JUN, FOS, FOSL2, JUNB, HSF1, CUX1, IRF5, ESX1, and ETS2 are introduced into a human pluripotent stem cell.

Example 33

(Differentiation into Placenta)

In this Example, a human embryonic stem cell can be differentiated into the placenta, in particular, a cell present in the placenta by introducing, into the human embryonic stem cell, a transcription factor cocktail selected from the human gene expression correlation matrix of Example 1 of the present invention by the method described in Example 2 of the present invention.

A method for differentiation into the placenta of the present invention is as described below.

TFAP2C, ESX1, FOS, JUNB, TP73, IRF5, GATA3, TFE3, CEBPB, FOSL1, DLX6, JUN, FOXP1, ESRRB, NFIB, ETS2, HES1, ELF1, ZIC1, SALL4, TFAP2A, HSF1, HEY1, HHEX, TGIF1, THAP11, ETS1, ARNT2, IRF4, CUX1, GRHL2, HOXA9, TBX2, TBX5, and ELF5 are introduced into a human pluripotent stem cell.

Example 34

(Differentiation into Smooth Muscle)

In this Example, a human embryonic stem cell can be differentiated into a smooth muscle, in particular, a cell present in the smooth muscle by introducing, into the human embryonic stem cell, a transcription factor cocktail selected from the human gene expression correlation matrix of Example 1 of the present invention by the method described in Example 2 of the present invention.

A method for differentiation into the smooth muscle of the present invention is as described below.

JUN, FOSL1, FOS, GADD45A, FOSL2, HSF1, JUNB, CUX1, IRF5, GATA3, and ETS2 are introduced into a human pluripotent stem cell.

Example 35

(Differentiation into Lung)

In this Example, a human embryonic stem cell can be differentiated into the lung, in particular, a cell present in the lung by introducing, into the human embryonic stem cell, a transcription factor cocktail selected from the human gene expression correlation matrix of Example 1 of the present invention by the method described in Example 2 of the present invention.

A method for differentiation into the lung (in particular, the lung, a bronchial epithelial cell, the fetal lung, or the trachea) of the present invention is as described below.

Lung: SALL4, TGIF1, FOS, TP73, NFIB, TFAP2C, ESX1, DLX6, PITX2, TFE3, JUNB, FOXP1, ZNF281, CEBPB, ZIC1, IRF5, CTCFL, HOXA9, FOSL1, TCF4, GATA3, ETS2, EGFLAM, ARID3A, KLF4, FOSL2, HHEX, ETS1, ELF1, ESRRB, IRF4, NRF1, HES1, GRHL2, FOXG1, ELF5, PRDM1, RFX2, JUN, HNF4A, TFAP2A, ERG, ARNT2, and HEY1 are introduced into a human pluripotent stem cell.

Bronchial epithelial cell: GADD45A, JUN, FOSL1, MYC, CUX1, IRF5, ESRRB, FOS, L3MBTL2, TRPV2, and FOSL2 are introduced into a human pluripotent stem cell.

Fetal lung: CEBPB, GATA3, ESX1, NFIB, JUNB, IRF5, JUN, ETS2, HSF1, ESRRB, FOSL1, TGIF1, TBX2, TFAP2C, FOS, and HNF4A are introduced into a human pluripotent stem cell.

Trachea: JUNB, HES1, TP73, TFAP2C, ESX1, CEBPB, GATA3, ELF1, FOXA2, FOS, IRF5, HEY1, NFIB, IRF4, ZIC1, FOXA1, NFIC, TBX5, CTCF, ESRRB, E2F6, FOSL1, HSF1, and IRF1 are introduced into a human pluripotent stem cell.

(General Remark)

In Examples of the present invention, human embryonic stem cells can be differentiated into desired cell types by introducing, into the human embryonic stem cells, the transcription factor cocktails selected from the human gene expression correlation matrix of Example 1 of the present invention by the method described in Example 2 of the present invention.

INDUSTRIAL APPLICABILITY

According to the present invention, the novel method of differentiating a pluripotent stem cell into a desired cell type can be provided.

---

The invention claimed is:

1. A method of differentiating a pluripotent stem cell into a hepatoblast and/or a liver cell, including a step of introducing a transcription factor including any one of the following (1) to (5) into a pluripotent stem cell of mammalian origin:
   (1) one transcription factor selected from TGIF, TCF4, PITX2, and MEIS1;
   (2) two transcription factors selected from TGIF, TCF4, PITX2, SALL4, and MEIS1;
   (3) three transcription factors selected from TGIF, TCF4, PITX2, SALL4, and MEIS1;
   (4) four transcription factors selected from TGIF, TCF4, PITX2, SALL4, and MEIS1 and
   (5) five transcription factors selected from TGIF, TCF4, PITX2, SALL4, and MEIS1.

2. The method according to claim 1, wherein the transcription factor is TGIF.

3. The method according to claim 1, wherein the transcription factor is TCF4.

4. The method according to claim 1, wherein the transcription factor is PITX2.

5. The method according to claim 1, wherein the transcription factor is SALL4 and at least one other of said transcription factors.

6. The method according to claim 1, wherein the transcription factor is MEIS1.

7. The method according to claim 1, wherein the transcription factor is an mRNA encoding amino acid sequences of the transcription factor, a synthetic mRNA encoding amino acid sequences of the transcription factor, a nucleic acid encoding amino acid sequences of the transcription factor, or a protein.

* * * * *

SEQUENCE LISTING

```
<160> NUMBER OF SEQ ID NOS: 34

<210> SEQ ID NO 1
<211> LENGTH: 1071
<212> TYPE: DNA
<213> ORGANISM: Homo sapiens

<400> SEQUENCE: 1
atgaccaaat cgtacagcga gagtgggctg atgggcgagc ctcagcccca aggtcctcca       60
agctggacag acgagtgtct cagttctcag gacgaggagc acgaggcaga caagaaggag      120
```

-continued

```
gacgacctcg aaaccatgaa cgcagaggag gactcactga ggaacggggg agaggaggag      180
gacgaagatg aggacctgga agaggaggaa gaagaggaag aggaggatga cgatcaaaag      240
cccaagagac gcggcccaa aaagaagaag atgactaagg ctcgcctgga gcgttttaaa       300
ttgagacgca tgaaggctaa cgcccgggag cggaaccgca tgcacggact gaacgcggcg      360
ctagacaacc tgcgcaaggt ggtgccttgc tattctaaga cgcagaagct gtccaaaatc      420
gagactctgc gcttggccaa gaactacatc tgggctctgt cggagatcct gcgctcaggc      480
aaaagcccag acctggtctc cttcgttcag acgctttgca agggcttatc ccaacccacc      540
accaacctgg ttgcgggctg cctgcaactc aatcctcgga cttttctgcc tgagcagaac      600
caggacatgc cccccacct gccgacggcc agcgcttcct tccctgtaca cccctactcc       660
taccagtcgc ctgggctgcc cagtccgcct acggtacca tggacagctc ccatgtcttc       720
cacgttaagc ctccgccgca cgcctacagc gcagcgctgg agcccttctt tgaaagccct      780
ctgactgatt gcaccagccc ttcctttgat ggacccctca gcccgccgct cagcatcaat      840
ggcaacttct ctttcaaaca cgaaccgtcc gccgagtttg agaaaaatta tgcctttacc      900
atgcactatc ctgcagcgac actggcaggg gcccaaagcc acggatcaat cttctcaggc      960
accgctgccc ctcgctgcga gatccccata gacaatatta tgtccttcga tagccattca     1020
catcatgagc gagtcatgag tgcccagctc aatgccatat ttcatgatta g              1071
```

<210> SEQ ID NO 2
<211> LENGTH: 356
<212> TYPE: PRT
<213> ORGANISM: Homo sapiens

<400> SEQUENCE: 2

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Thr Met Asn Ala
        35                  40                  45

Glu Glu Asp Ser Leu Arg Asn Gly Gly Glu Glu Asp Glu Asp Glu
    50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205
```

```
Thr Ala Ser Ala Ser Phe Pro Val His Pro Tyr Ser Tyr Gln Ser Pro
    210                 215                 220
Gly Leu Pro Ser Pro Pro Tyr Gly Thr Met Asp Ser Ser His Val Phe
225                 230                 235                 240
His Val Lys Pro Pro Pro His Ala Tyr Ser Ala Ala Leu Glu Pro Phe
                245                 250                 255
Phe Glu Ser Pro Leu Thr Asp Cys Thr Ser Pro Ser Phe Asp Gly Pro
            260                 265                 270
Leu Ser Pro Pro Leu Ser Ile Asn Gly Asn Phe Ser Phe Lys His Glu
        275                 280                 285
Pro Ser Ala Glu Phe Glu Lys Asn Tyr Ala Phe Thr Met His Tyr Pro
    290                 295                 300
Ala Ala Thr Leu Ala Gly Ala Gln Ser His Gly Ser Ile Phe Ser Gly
305                 310                 315                 320
Thr Ala Ala Pro Arg Cys Glu Ile Pro Ile Asp Asn Ile Met Ser Phe
                325                 330                 335
Asp Ser His Ser His His Glu Arg Val Met Ser Ala Gln Leu Asn Ala
            340                 345                 350
Ile Phe His Asp
        355

<210> SEQ ID NO 3
<211> LENGTH: 1149
<212> TYPE: DNA
<213> ORGANISM: Homo sapiens

<400> SEQUENCE: 3
atgctgaccc gcctgttcag cgagcccggc cttctctcgg acgtgcccaa gttcgccagc       60
tggggcgacg gcgaagacga cgagccgagg agcgacaagg gcgacgcgcc gccaccgcca      120
ccgcctgcgc ccgggccagg ggctccgggg ccagcccggg cggccaagcc agtccctctc      180
cgtggagaag aggggacgga ggccacgttg gccgaggtca aggaggaagg cgagctgggg      240
ggagaggagg aggaggaaga ggaggaggaa gaaggactgg acgaggcgga gggcgagcgg      300
cccaagaagc gcgggcccaa gaagcgcaag atgaccaagg cgcgcttgga gcgctccaag      360
cttcggcggc agaaggcgaa cgcgcgggag cgcaaccgca tgcacgacct gaacgcagcc      420
ctggacaacc tgcgcaaggt ggtgcccctgc tactccaaga gcagaagct gtccaagatc      480 gagacgctgc gcctagccaa gaactatatc tgggcgctct cggagatcct cgctccggc      540 aagcggccag acctagtgtc ctacgtgcag actctgtgca agggtctgtc gcagcccacc      600
accaatctgg tggccggctg tctgcagctc aactctcgca acttcctcac ggagcaaggc      660
gccgacggtg ccgccgcgtt ccacggctcg ggcggccgt cgccatgca cccctacccg      720 tacccgtgct cgcgcctggc gggcgcacag tgccaggcgg ccggcggcct gggcggcggc      780
gcggcgcacg ccctgcggac ccacggctac tgcgccgcct acgagacgct gtatgcggcg      840
gcaggcggtg gcggcgcgag cccggactac aacagctccg agtacgaggg cccgctcagc      900 ccccgctct gtctcaatgg caacttctca ctcaagcagg actcctcgcc cgaccacgag      960
aaaagctacc actactctat gcactactcg gcgctgcccg ttcgcggcc acgggccac     1020 gggctagtct tcggctcgtc ggctgtgcgc gggggcgtcc actcggagaa tctcttgtct     1080
tacgatatgc accttcacca cgaccggggc cccatgtacg aggagctcaa tgcgtttttt     1140
cataactga                                                              1149
```

<210> SEQ ID NO 4
<211> LENGTH: 382
<212> TYPE: PRT
<213> ORGANISM: Homo sapiens

<400> SEQUENCE: 4

```
Met Leu Thr Arg Leu Phe Ser Glu Pro Gly Leu Leu Ser Asp Val Pro
 1               5                  10                  15

Lys Phe Ala Ser Trp Gly Asp Gly Glu Asp Glu Pro Arg Ser Asp
            20                  25                  30

Lys Gly Asp Ala Pro Pro Pro Pro Ala Pro Gly Pro Gly Ala
            35                  40                  45

Pro Gly Pro Ala Arg Ala Ala Lys Pro Val Pro Leu Arg Gly Glu Glu
50                  55                  60

Gly Thr Glu Ala Thr Leu Ala Glu Val Lys Glu Gly Glu Leu Gly
65                  70                  75                  80

Gly Glu Glu Glu Glu Glu Glu Glu Glu Gly Leu Asp Glu Ala
                85                  90                  95

Glu Gly Glu Arg Pro Lys Lys Arg Gly Pro Lys Lys Arg Lys Met Thr
                100                 105                 110

Lys Ala Arg Leu Glu Arg Ser Lys Leu Arg Arg Gln Lys Ala Asn Ala
            115                 120                 125

Arg Glu Arg Asn Arg Met His Asp Leu Asn Ala Ala Leu Asp Asn Leu
130                 135                 140

Arg Lys Val Val Pro Cys Tyr Ser Lys Thr Gln Lys Leu Ser Lys Ile
145                 150                 155                 160

Glu Thr Leu Arg Leu Ala Lys Asn Tyr Ile Trp Ala Leu Ser Glu Ile
                165                 170                 175

Leu Arg Ser Gly Lys Arg Pro Asp Leu Val Ser Tyr Val Gln Thr Leu
            180                 185                 190

Cys Lys Gly Leu Ser Gln Pro Thr Thr Asn Leu Val Ala Gly Cys Leu
            195                 200                 205

Gln Leu Asn Ser Arg Asn Phe Leu Thr Glu Gln Gly Ala Asp Gly Ala
        210                 215                 220

Gly Arg Phe His Gly Ser Gly Gly Pro Phe Ala Met His Pro Tyr Pro
225                 230                 235                 240

Tyr Pro Cys Ser Arg Leu Ala Gly Ala Gln Cys Gln Ala Ala Gly Gly
                245                 250                 255

Leu Gly Gly Gly Ala Ala His Ala Leu Arg Thr His Gly Tyr Cys Ala
            260                 265                 270

Ala Tyr Glu Thr Leu Tyr Ala Ala Gly Gly Gly Ala Ser Pro
        275                 280                 285

Asp Tyr Asn Ser Ser Glu Tyr Glu Gly Pro Leu Ser Pro Pro Leu Cys
        290                 295                 300

Leu Asn Gly Asn Phe Ser Leu Lys Gln Asp Ser Ser Pro Asp His Glu
305                 310                 315                 320

Lys Ser Tyr His Tyr Ser Met His Tyr Ser Ala Leu Pro Gly Ser Arg
                325                 330                 335

Pro Thr Gly His Gly Leu Val Phe Gly Ser Ser Ala Val Arg Gly Gly
            340                 345                 350

Val His Ser Glu Asn Leu Leu Ser Tyr Asp Met His Leu His His Asp
        355                 360                 365

Arg Gly Pro Met Tyr Glu Glu Leu Asn Ala Phe Phe His Asn
370                 375                 380
```

<210> SEQ ID NO 5
<211> LENGTH: 714
<212> TYPE: DNA
<213> ORGANISM: Homo sapiens

<400> SEQUENCE: 5

```
atgccagccc gccttgagac ctgcatctcc gacctcgact gcgccagcag cagcggcagt      60
gacctatccg gcttcctcac cgacgaggaa gactgtgcca gactccaaca ggcagcctcc     120
gcttcggggc cgcccgcgcc ggcccgcagg ggcgcgccca atatctcccg ggcgtctgag     180
gttccagggg cacaggacga cgagcaggag aggcggcggc gccgcggccg gacgcgggtc     240
cgctccgagg cgctgctgca ctcgctgcgc aggagccggc gcgtcaaggc caacgatcgc     300
gagcgcaacc gcatgcacaa cttgaacgcg gccctggacg cactgcgcag cgtgctgccc     360
tcgttccccg acgacaccaa gctcaccaaa atcgagacgc tgcgcttcgc ctacaactac     420
atctgggctc tggccgagac actgcgcctg gcggatcaag gctgcccgg aggcggtgcc     480
cgggagcgcc tcctgccgcc gcagtgcgtc cctgcctgc ccggtccccc aagccccgcc     540
agcgacgcga gtcctgggg ctcaggtgcc gccgccgcct cccgctctc tgaccccagt      600
agcccagccg cctccgaaga cttcacctac cgccccggcg accctgtttt ctccttccca     660
agcctgccca agacttgct ccacacaacg ccctgtttca ttccttacca ctag             714
```

<210> SEQ ID NO 6
<211> LENGTH: 237
<212> TYPE: PRT
<213> ORGANISM: Homo sapiens

<400> SEQUENCE: 6

Met Pro Ala Arg Leu Glu Thr Cys Ile Ser Asp Leu Asp Cys Ala Ser
1               5                   10                  15

Ser Ser Gly Ser Asp Leu Ser Gly Phe Leu Thr Asp Glu Glu Asp Cys
            20                  25                  30

Ala Arg Leu Gln Gln Ala Ala Ser Ala Ser Gly Pro Pro Ala Pro Ala
        35                  40                  45

Arg Arg Gly Ala Pro Asn Ile Ser Arg Ala Ser Glu Val Pro Gly Ala
    50                  55                  60

Gln Asp Asp Glu Gln Glu Arg Arg Arg Arg Gly Arg Thr Arg Val
65                  70                  75                  80

Arg Ser Glu Ala Leu Leu His Ser Leu Arg Arg Ser Arg Arg Val Lys
                85                  90                  95

Ala Asn Asp Arg Glu Arg Asn Arg Met His Asn Leu Asn Ala Ala Leu
            100                 105                 110

Asp Ala Leu Arg Ser Val Leu Pro Ser Phe Pro Asp Asp Thr Lys Leu
        115                 120                 125

Thr Lys Ile Glu Thr Leu Arg Phe Ala Tyr Asn Tyr Ile Trp Ala Leu
    130                 135                 140

Ala Glu Thr Leu Arg Leu Ala Asp Gln Gly Leu Pro Gly Gly Gly Ala
145                 150                 155                 160

Arg Glu Arg Leu Leu Pro Pro Gln Cys Val Pro Cys Leu Pro Gly Pro
                165                 170                 175

Pro Ser Pro Ala Ser Asp Ala Glu Ser Trp Gly Ser Gly Ala Ala Ala
            180                 185                 190

Ala Ser Pro Leu Ser Asp Pro Ser Ser Pro Ala Ala Ser Glu Asp Phe
        195                 200                 205

Thr Tyr Arg Pro Gly Asp Pro Val Phe Ser Phe Pro Ser Leu Pro Lys
    210                 215                 220

Asp Leu Leu His Thr Thr Pro Cys Phe Ile Pro Tyr His
225                 230                 235

<210> SEQ ID NO 7
<211> LENGTH: 819
<212> TYPE: DNA
<213> ORGANISM: Homo sapiens

<400> SEQUENCE: 7

| | | | | | |
|---|---|---|---|---|---|
| atgttcgtca | aatccgagac | cttggagttg | aaggaggaag | aggacgtgtt | agtgctgctc | 60 |
| ggatcggcct | ccccgcctt | ggcggccctg | accccgctgt | catccagcgc | cgacgaagaa | 120 |
| gaggaggagg | agccgggcgc | gtcaggcggg | gcgcgtcggc | agcgcggggc | tgaggccggg | 180 |
| caggggggcgc | ggggcggcgt | ggctgcgggt | gcggagggct | gccggcccgc | acggctgctg | 240 |
| ggtctggtac | acgattgcaa | acggcgccct | tccgggcgc | gggccgtctc | ccgaggcgcc | 300 |
| aagacggccg | agacggtgca | gcgcatcaag | aagacccgta | gactgaaggc | caacaaccgc | 360 |
| gagcgaaacc | gcatgcacaa | cctcaacgcg | gcactggacg | cgctgcgcga | ggtgctcccc | 420 |
| acgttccccg | aggacgccaa | gctcaccaag | atcgagaccc | tgcgcttcgc | ccacaactac | 480 |
| atctgggcac | tcaccgagac | cctgcgcctg | gcggatcact | gcggggggcgg | cggcgggggc | 540 |
| ctgccggggg | cgctcttctc | cgaggcagtg | ttgctgagcc | cggggaggagc | cagcgccgcc | 600 |
| ctgagcagca | gcggagacag | cccctcgccc | gcctccacgt | ggagttgcac | caacagcccc | 660 |
| gcgccgtcct | cctccgtgtc | ctccaattcc | acctccccct | acagctgcac | tttatcgccc | 720 |
| gccagcccgg | ccgggtcaga | catggactat | tggcagcccc | cacctcccga | caagcaccgc | 780 |
| tatgcacctc | acctccccat | agccagggat | tgtatctag | | | 819 |

<210> SEQ ID NO 8
<211> LENGTH: 272
<212> TYPE: PRT
<213> ORGANISM: Homo sapiens

<400> SEQUENCE: 8

Met Phe Val Lys Ser Glu Thr Leu Glu Leu Lys Glu Glu Glu Asp Val
1               5                   10                  15

Leu Val Leu Leu Gly Ser Ala Ser Pro Ala Leu Ala Ala Leu Thr Pro
                20                  25                  30

Leu Ser Ser Ser Ala Asp Glu Glu Glu Glu Glu Pro Gly Ala Ser
            35                  40                  45

Gly Gly Ala Arg Arg Gln Arg Gly Ala Glu Ala Gly Gln Gly Ala Arg
    50                  55                  60

Gly Gly Val Ala Ala Gly Ala Glu Gly Cys Arg Pro Ala Arg Leu Leu
65                  70                  75                  80

Gly Leu Val His Asp Cys Lys Arg Arg Pro Ser Arg Ala Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr

|  |  |  | 145 |  |  |  | 150 |  |  |  | 155 |  |  |  | 160 |
|---|---|---|---|---|---|---|---|---|---|---|---|---|---|---|---|

Ile Trp Ala Leu Thr Glu Thr Leu Arg Leu Ala Asp His Cys Gly Gly
                165                 170                 175

Gly Gly Gly Gly Leu Pro Gly Ala Leu Phe Ser Glu Ala Val Leu Leu
            180                 185                 190

Ser Pro Gly Gly Ala Ser Ala Ala Leu Ser Ser Ser Gly Asp Ser Pro
        195                 200                 205

Ser Pro Ala Ser Thr Trp Ser Cys Thr Asn Ser Pro Ala Pro Ser Ser
    210                 215                 220

Ser Val Ser Ser Asn Ser Thr Ser Pro Tyr Ser Cys Thr Leu Ser Pro
225                 230                 235                 240

Ala Ser Pro Ala Gly Ser Asp Met Asp Tyr Trp Gln Pro Pro Pro Pro
                245                 250                 255

Asp Lys His Arg Tyr Ala Pro His Leu Pro Ile Ala Arg Asp Cys Ile
                260                 265                 270

<210> SEQ ID NO 9
<211> LENGTH: 645
<212> TYPE: DNA
<213> ORGANISM: Homo sapiens

<400> SEQUENCE: 9

```
atgacgcctc aaccctcggg tgcgcccact gtccaagtga cccgtgagac ggagcggtcc      60
ttccccagag cctcggaaga cgaagtgacc tgccccacgt ccgccccgcc cagccccact     120
cgcacacggg ggaactgcgc agaggcggaa gagggaggct gccgaggggc ccgaggaag      180
ctccgggcac ggcgcggggg acgcagccgg cctaagagcg agttggcact gagcaagcag     240
cgacggagtc ggcgaaagaa ggccaacgac cgcgagcgca atcgaatgca caacctcaac     300
tcggcactgg acgccctgcg cggtgtcctg cccaccttcc agacgacgc gaagctcacc      360
aagatcgaga cgctgcgctt cgcccacaac tacatctggg cgctgactca aacgctgcgc     420
atagcggacc acagcttgta cgcgctggag ccgccggcgc cgcactgcgg ggagctgggc     480
agcccaggcg gttcccccgg ggactggggg tccctctact ccccagtctc ccaggctggc     540
agcctgagtc ccgccgcgtc gctggaggag cgacccgggc tgctggggc cacctttcc       600
gcctgcttga gcccaggcag tctggctttc tcagattttc tgtga                    645
```

<210> SEQ ID NO 10
<211> LENGTH: 214
<212> TYPE: PRT
<213> ORGANISM: Homo sapiens

<400> SEQUENCE: 10

Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

```
His Asn Leu Asn Ser Ala Leu Asp Ala Leu Arg Gly Val Leu Pro Thr
                100                 105                 110

Phe Pro Asp Asp Ala Lys Leu Thr Lys Ile Glu Thr Leu Arg Phe Ala
            115                 120                 125

His Asn Tyr Ile Trp Ala Leu Thr Gln Thr Leu Arg Ile Ala Asp His
        130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Phe Ser Ala Cys Leu Ser Pro Gly Ser Leu
        195                 200                 205

Ala Phe Ser Asp Phe Leu
    210
```

<210> SEQ ID NO 11
<211> LENGTH: 819
<212> TYPE: DNA
<213> ORGANISM: Homo sapiens

<400> SEQUENCE: 11

```
atgaaaggca agaaaggtat tgttgcagca tctggcagtg agactgagga tgaggacagc      60
atggacattc ccttggacct ttcttcatcc gctggctcag gcaagagaag gagaaggggc     120
aacctaccca aggagtctgt gcagattctt cgggattggc tgtatgagca ccgttacaat     180
gcctatcctt cagagcaaga aaaagcgttg ctgtcccagc aaacacacct gtctacgcta     240
caggtctgta actggttcat caacgcccgc cgcaggctcc tccctgacat gctgagaaag     300
gatggcaaag atccaaatca gttcacaatt cccgccgtg gggccaagat ttctgaaacg     360
agctctgtgg agtccgtgat gggcatcaaa aacttcatgc agctctaga ggagacccca     420
tttcattcct gtacagctgg gccaaaccca accctaggga ggccactgtc tcctaagccg     480
tcatccccgg atcagttttt ggctcgtcca tcagtgatct gccataccac tgtgactgca     540
ttgaaagatg tcccttctc tctctgccag tcggtcggtg tgggacaaaa cacagatata     600
cagcagatag cggccaaaaa cttcacagac acctctctca tgtacccaga ggacacttgt     660
aaatctggac caagtacgaa tacacagagt ggtcttttca cactcctcc ccctactcca     720
ccggacctca accaggactt cagtggattt cagcttctag tggatgttgc actcaaacgg     780
gctgcagaga tggagcttca ggcaaaactt acagcttaa                           819
```

<210> SEQ ID NO 12
<211> LENGTH: 272
<212> TYPE: PRT
<213> ORGANISM: Homo sapiens

<400> SEQUENCE: 12

```
Met Lys Gly Lys Lys Gly Ile Val Ala Ala Ser Gly Ser Glu Thr Glu
1               5                   10                  15

Asp Glu Asp Ser Met Asp Ile Pro Leu Asp Leu Ser Ser Ala Gly
                20                  25                  30

Ser Gly Lys Arg Arg Arg Arg Gly Asn Leu Pro Lys Glu Ser Val Gln
            35                  40                  45

Ile Leu Arg Asp Trp Leu Tyr Glu His Arg Tyr Asn Ala Tyr Pro Ser
        50                  55                  60
```

```
Glu Gln Glu Lys Ala Leu Leu Ser Gln Gln Thr His Leu Ser Thr Leu
 65                  70                  75                  80

Gln Val Cys Asn Trp Phe Ile Asn Ala Arg Arg Leu Leu Pro Asp
                 85                  90                  95

Met Leu Arg Lys Asp Gly Lys Asp Pro Asn Gln Phe Thr Ile Ser Arg
            100                 105                 110

Arg Gly Ala Lys Ile Ser Glu Thr Ser Ser Val Glu Ser Val Met Gly
            115                 120                 125

Ile Lys Asn Phe Met Pro Ala Leu Glu Glu Thr Pro Phe His Ser Cys
130                 135                 140

Thr Ala Gly Pro Asn Pro Thr Leu Gly Arg Pro Leu Ser Pro Lys Pro
145                 150                 155                 160

Ser Ser Pro Gly Ser Val Leu Ala Arg Pro Ser Val Ile Cys His Thr
                165                 170                 175

Thr Val Thr Ala Leu Lys Asp Val Pro Phe Ser Leu Cys Gln Ser Val
            180                 185                 190

Gly Val Gly Gln Asn Thr Asp Ile Gln Gln Ile Ala Ala Lys Asn Phe
            195                 200                 205

Thr Asp Thr Ser Leu Met Tyr Pro Glu Asp Thr Cys Lys Ser Gly Pro
210                 215                 220

Ser Thr Asn Thr Gln Ser Gly Leu Phe Asn Thr Pro Pro Thr Pro
225                 230                 235                 240

Pro Asp Leu Asn Gln Asp Phe Ser Gly Phe Gln Leu Leu Val Asp Val
                245                 250                 255

Ala Leu Lys Arg Ala Ala Glu Met Glu Leu Gln Ala Lys Leu Thr Ala
            260                 265                 270

<210> SEQ ID NO 13
<211> LENGTH: 2016
<212> TYPE: DNA
<213> ORGANISM: Homo sapiens

<400> SEQUENCE: 13
atgcatcacc aacagcgaat ggctgcctta gggacggaca aagagctgag tgatttactg      60
gatttcagtg cgatgttttc acctcctgtg agcagtggga aaaatggacc aacttctttg     120
gcaagtggac attttactgg ctcaaatgta aagacagaa gtagctcagg tcctggggg      180 aatggaggac atccaagccc gtccaggaac tatggagatg ggactcccta tgaccacatg     240
accagcaggg accttgggtc acatgacaat ctctctccac cttttgtcaa ttccagaata     300
caaagtaaaa cagaaagggg ctcatactca tcttatggga gagaatcaaa cttacagggt     360
tgccaccagc agagtctcct tggaggtgac atggatatgg caacccagg aacccttcg      420 cccaccaaac ctggttccca gtactatcag tattctagca ataatccccg aaggaggcct     480
cttcacagta gtgccatgga ggtacagaca aagaaagttc gaaaagttcc tccaggtttg     540
ccatcttcag tctatgctcc atcagcaagc actgccgact acaatgggga ctcgccaggc     600
tatccttcct ccaaaccagc aaccagcact ttccctagct ccttcttcat gcaagatggc     660
catcacagca gtgaccttg gagctcctcc agtgggatga atcagcctgg ctatgcagga     720
atgttgggca actcttctca tattccacag tccagcagct actgtagcct gcatccacat     780
gaacgtttga gctatccatc acactcctca gcagacatca attccagtct tcctccgatg     840 tccacttttcc atcgtagtgg tacaaaccat tacagcacct cttcctgtac gcctcctgcc     900
aacgggacag acagtataat ggcaaataga ggaagcgggg cagccggcag ctcccagact     960
```

```
ggagatgctc tggggaaagc acttgcttcg atctattctc cagatcacac taacaacagc    1020
ttttcatcaa acccttcaac tcctgttggc tctcctccat ctctctcagc aggcacagct    1080
gtttggtcta gaaatggagg acaggcctca tcgtctccta attatgaagg acccttacac    1140
tctttgcaaa gccgaattga agatcgttta gaaagactgg atgatgctat tcatgttctc    1200
cggaaccatg cagtgggccc atccacagct atgcctggtg gtcatgggga catgcatgga    1260
atcattggac cttctcataa tggagccatg ggtggtctgg gctcagggta tggaaccggc    1320
cttctttcag ccaacagaca ttcactcatg gtggggaccc atcgtgaaga tggcgtggcc    1380
ctgagaggca gccattctct tctgccaaac caggttccgg ttccacagct tcctgtccag    1440
tctgcgactt ccctgacct gaacccaccc caggacctt acagaggcat gccaccagga    1500
ctacaggggc agagtgtctc ctctggcagc tctgagatca atccgatga cgagggtgat    1560 gagaacctgc aagacacgaa atcttcggag acaagaaat tagatgacga caagaaggat    1620
atcaaatcaa ttactaggtc aagatctagc aataatgacg atgaggacct gacaccagag    1680
cagaaggcag agcgtgagaa ggagcggagg atggccaaca atgcccgaga gcgtctgcgg    1740
gtccgtgaca tcaacgaggc tttcaaagag ctcggccgca tggtgcagct ccacctcaag    1800
agtgacaagc cccagaccaa gctcctgatc ctccaccagg cggtggccgt catcctcagt    1860
ctggagcagc aagtccgaga aaggaatctg aatccgaaag ctgcgtgtct gaaaagaagg    1920
gaggaagaga aggtgtcctc agagcctccc cctctctcct tggccggccc acaccctgga    1980
atgggagacg catcgaatca catgggacag atgtaa                              2016
```

<210> SEQ ID NO 14
<211> LENGTH: 671
<212> TYPE: PRT
<213> ORGANISM: Homo sapiens

<400> SEQUENCE: 14

```
Met His His Gln Gln Arg Met Ala Ala Leu Gly Thr Asp Lys Glu Leu
1               5                   10                  15

Ser Asp Leu Leu Asp Phe Ser Ala Met Phe Ser Pro Pro Val Ser Ser
            20                  25                  30

Gly Lys Asn Gly Pro Thr Ser Leu Ala Ser Gly His Phe Thr Gly Ser
        35                  40                  45

Asn Val Glu Asp Arg Ser Ser Ser Gly Ser Trp Gly Asn Gly Gly His
    50                  55                  60

Pro Ser Pro Ser Arg Asn Tyr Gly Asp Gly Thr Pro Tyr Asp His Met
65                  70                  75                  80

Thr Ser Arg Asp Leu Gly Ser His Asp Asn Leu Ser Pro Pro Phe Val
                85                  90                  95

Asn Ser Arg Ile Gln Ser Lys Thr Glu Arg Gly Ser Tyr Ser Ser Tyr
            100                 105                 110

Gly Arg Glu Ser Asn Leu Gln Gly Cys His Gln Ser Leu Leu Gly
        115                 120                 125

Gly Asp Met Asp Met Gly Asn Pro Gly Thr Leu Ser Pro Thr Lys Pro
    130                 135                 140

Gly Ser Gln Tyr Tyr Gln Tyr Ser Ser Asn Asn Pro Arg Arg Arg Pro
145                 150                 155                 160

Leu His Ser Ser Ala Met Glu Val Gln Thr Lys Lys Val Arg Lys Val
                165                 170                 175

Pro Pro Gly Leu Pro Ser Ser Val Tyr Ala Pro Ser Ala Ser Thr Ala
```

-continued

```
                180                 185                 190
Asp Tyr Asn Arg Asp Ser Pro Gly Tyr Pro Ser Ser Lys Pro Ala Thr
                195                 200                 205

Ser Thr Phe Pro Ser Ser Phe Phe Met Gln Asp Gly His His Ser Ser
        210                 215                 220

Asp Pro Trp Ser Ser Ser Ser Gly Met Asn Gln Pro Gly Tyr Ala Gly
225                 230                 235                 240

Met Leu Gly Asn Ser Ser His Ile Pro Gln Ser Ser Ser Tyr Cys Ser
                245                 250                 255

Leu His Pro His Glu Arg Leu Ser Tyr Pro Ser His Ser Ser Ala Asp
        260                 265                 270

Ile Asn Ser Ser Leu Pro Pro Met Ser Thr Phe His Arg Ser Gly Thr
        275                 280                 285

Asn His Tyr Ser Thr Ser Ser Cys Thr Pro Pro Ala Asn Gly Thr Asp
        290                 295                 300

Ser Ile Met Ala Asn Arg Gly Ser Gly Ala Ala Gly Ser Ser Gln Thr
305                 310                 315                 320

Gly Asp Ala Leu Gly Lys Ala Leu Ala Ser Ile Tyr Ser Pro Asp His
                325                 330                 335

Thr Asn Asn Ser Phe Ser Ser Asn Pro Ser Thr Pro Val Gly Ser Pro
                340                 345                 350

Pro Ser Leu Ser Ala Gly Thr Ala Val Trp Ser Arg Asn Gly Gly Gln
        355                 360                 365

Ala Ser Ser Ser Pro Asn Tyr Glu Gly Pro Leu His Ser Leu Gln Ser
        370                 375                 380

Arg Ile Glu Asp Arg Leu Glu Arg Leu Asp Asp Ala Ile His Val Leu
385                 390                 395                 400

Arg Asn His Ala Val Gly Pro Ser Thr Ala Met Pro Gly Gly His Gly
                405                 410                 415

Asp Met His Gly Ile Ile Gly Pro Ser His Asn Gly Ala Met Gly Gly
                420                 425                 430

Leu Gly Ser Gly Tyr Gly Thr Gly Leu Leu Ser Ala Asn Arg His Ser
        435                 440                 445

Leu Met Val Gly Thr His Arg Glu Asp Gly Val Ala Leu Arg Gly Ser
        450                 455                 460

His Ser Leu Leu Pro Asn Gln Val Pro Val Pro Gln Leu Pro Val Gln
465                 470                 475                 480

Ser Ala Thr Ser Pro Asp Leu Asn Pro Pro Gln Asp Pro Tyr Arg Gly
                485                 490                 495

Met Pro Pro Gly Leu Gln Gly Gln Ser Val Ser Ser Gly Ser Ser Glu
                500                 505                 510

Ile Lys Ser Asp Asp Glu Gly Asp Glu Asn Leu Gln Asp Thr Lys Ser
        515                 520                 525

Ser Glu Asp Lys Lys Leu Asp Asp Asp Lys Asp Ile Lys Ser Ile
        530                 535                 540

Thr Arg Ser Arg Ser Ser Asn Asn Asp Asp Glu Asp Leu Thr Pro Glu
545                 550                 555                 560

Gln Lys Ala Glu Arg Glu Lys Glu Arg Arg Met Ala Asn Asn Ala Arg
                565                 570                 575

Glu Arg Leu Arg Val Arg Asp Ile Asn Glu Ala Phe Lys Glu Leu Gly
                580                 585                 590

Arg Met Val Gln Leu His Leu Lys Ser Asp Lys Pro Gln Thr Lys Leu
                595                 600                 605
```

Leu Ile Leu His Gln Ala Val Ala Val Ile Leu Ser Leu Glu Gln Gln
        610                 615                 620

Val Arg Glu Arg Asn Leu Asn Pro Lys Ala Ala Cys Leu Lys Arg Arg
625                 630                 635                 640

Glu Glu Glu Lys Val Ser Ser Glu Pro Pro Leu Ser Leu Ala Gly
                645                 650                 655

Pro His Pro Gly Met Gly Asp Ala Ser Asn His Met Gly Gln Met
            660                 665                 670

<210> SEQ ID NO 15
<211> LENGTH: 975
<212> TYPE: DNA
<213> ORGANISM: Homo sapiens

<400> SEQUENCE: 15

```
atgaactgca tgaaaggccc gcttcacttg gagcaccgag cagcggggac caagctgtcg    60
gccgtctcct catcttcctg tcaccatccc cagccgttag ccatggcttc ggttctggct   120
cccggtcagc cccggtcgct ggactcctcc aagcacaggc tggaggtgca ccatctcc    180
gacacctcca gcccggaggc cgcagagaaa gataaaagcc agcaggggaa gaatgaggac   240
gtgggcgccg aggacccgtc taagaagaag cggcaaaggc ggcagcggac tcactttacc   300
agccagcagc tccaggagct ggaggccact ttccagagga accgctaccc ggacatgtcc   360
acacgcgaag aaatcgctgt gtggaccaac cttacggaag cccgagtccg ggtttggttc   420
aagaatcgtc gggccaaatg gagaaagagg gagcgcaacc agcaggccga gctatgcaag   480
aatggcttcg ggccgcagtt caatgggctc atgcagccct acgacgacat gtacccaggc   540
tattcctaca caactgggc cgccaagggc cttacatccg cctccctatc caccaagagc   600
ttccccttct tcaactctat gaacgtcaac ccctgtcat cacagagcat gttttcccca   660
cccaactcta tctcgtccat gagcatgtcg tccagcatgg tgcctcagc agtgacaggc   720
gtcccgggct ccagtctcaa cagcctgaat aacttgaaca acctgagtag cccgtcgctg   780
aattccgcgg tgccgacgcc tgcctgtcct tacgcgccgc cgactcctcc gtatgtttat   840
agggacacgt gtaactcgag cctggccagc ctgagactga aagcaaagca gcactccagc   900
ttcggctacg ccagcgtgca gaacccggcc tccaacctga gtgcttgcca gtatgcagtg   960
gaccggcccg tgtga                                                    975
```

<210> SEQ ID NO 16
<211> LENGTH: 324
<212> TYPE: PRT
<213> ORGANISM: Homo sapiens

<400> SEQUENCE: 16

Met Asn Cys Met Lys Gly Pro Leu His Leu Glu His Arg Ala Ala Gly
1                5                  10                  15

Thr Lys Leu Ser Ala Val Ser Ser Ser Cys His His Pro Gln Pro
            20                  25                  30

Leu Ala Met Ala Ser Val Leu Ala Pro Gly Gln Pro Arg Ser Leu Asp
        35                  40                  45

Ser Ser Lys His Arg Leu Glu Val His Thr Ile Ser Asp Thr Ser Ser
    50                  55                  60

Pro Glu Ala Ala Glu Lys Asp Lys Ser Gln Gln Gly Lys Asn Glu Asp
65                  70                  75                  80

Val Gly Ala Glu Asp Pro Ser Lys Lys Lys Arg Gln Arg Arg Gln Arg

|     |     |     |     | 85  |     |     |     |     | 90  |     |     |     |     | 95  |
| --- | --- | --- | --- | --- | --- | --- | --- | --- | --- | --- | --- | --- | --- | --- |

Thr His Phe Thr Ser Gln Gln Leu Gln Glu Leu Glu Ala Thr Phe Gln
                                                    100                                         105                                          110

Arg Asn Arg Tyr Pro Asp Met Ser Thr Arg Glu Glu Ile Ala Val Trp
                115                                          120                                          125

Thr Asn Leu Thr Glu Ala Arg Val Arg Val Trp Phe Lys Asn Arg Arg
130                                          135                                          140

Ala Lys Trp Arg Lys Arg Glu Arg Asn Gln Gln Ala Glu Leu Cys Lys
145                                          150                                          155                                          160

Asn Gly Phe Gly Pro Gln Phe Asn Gly Leu Met Gln Pro Tyr Asp Asp
                                 165                                          170                                          175

Met Tyr Pro Gly Tyr Ser Tyr Asn Asn Trp Ala Ala Lys Gly Leu Thr
                                 180                                          185                                          190

Ser Ala Ser Leu Ser Thr Lys Ser Phe Pro Phe Phe Asn Ser Met Asn
                195                                          200                                          205

Val Asn Pro Leu Ser Ser Gln Ser Met Phe Ser Pro Pro Asn Ser Ile
210                                          215                                          220

Ser Ser Met Ser Met Ser Ser Met Val Pro Ser Ala Val Thr Gly
225                                          230                                          235                                          240

Val Pro Gly Ser Ser Leu Asn Ser Leu Asn Asn Leu Asn Asn Leu Ser
                                 245                                          250                                          255

Ser Pro Ser Leu Asn Ser Ala Val Pro Thr Pro Ala Cys Pro Tyr Ala
                260                                          265                                          270

Pro Pro Thr Pro Pro Tyr Val Tyr Arg Asp Thr Cys Asn Ser Ser Leu
                275                                          280                                          285

Ala Ser Leu Arg Leu Lys Ala Lys Gln His Ser Ser Phe Gly Tyr Ala
                290                                          295                                          300

Ser Val Gln Asn Pro Ala Ser Asn Leu Ser Ala Cys Gln Tyr Ala Val
305                                          310                                          315                                          320

Asp Arg Pro Val

<210> SEQ ID NO 17
<211> LENGTH: 3162
<212> TYPE: DNA
<213> ORGANISM: Homo sapiens

<400> SEQUENCE: 17

| | | |
|---|---|---|
| atgtcgaggc gcaagcaggc gaaaccccag cacatcaact cggaggagga ccagggcgag | 60 |
| cagcagccgc agcagcagac cccggagttt gcagatgcgg ccccagcggc gcccgcggcg | 120 |
| ggggagctgg gtgctccagt gaaccaccca gggaatgacg aggtggcgag tgaggatgaa | 180 |
| gccacagtaa agcggcttcg tcgggaggag acgcacgtct gtgagaaatg ctgtgcggag | 240 |
| ttcttcagca tctctgagtt cctggaacat aagaaaaatt gcactaaaaa tccacctgtc | 300 |
| ctcatcatga atgacagcga ggggcctgtg ccttcagaag acttctccgg agctgtactg | 360 |
| agccaccagc ccaccagtcc cggcagtaag gactgtcaca gggagaatgg cggcagctca | 420 |
| gaggacatga aggagaagcc ggatgcggag tctgtggtgt acctaaagac agagacagcc | 480 |
| ctgccaccca cccccaggga cataagctat ttagccaaag caaagtggc caacactaat | 540 |
| gtgaccttgc aggcactacg gggcaccaag gtggcggtga atcagcggag cgcggatgca | 600 |
| ctccctgccc ccgtgcctgg tgccaacagc atcccgtggg tcctcgagca gatcttgtgt | 660 |
| ctgcagcagc agcagctaca gcagatccag ctcaccgagc agatccgcat ccaggtgaac | 720 |
| atgtgggcct cccacgccct ccactcaagc ggggcagggg ccgacactct gaagaccttg | 780 |

```
ggcagccaca tgtctcagca ggtttctgca gctgtggctt tgctcagcca gaaagctgga    840
agccaaggtc tgtctctgga tgccttgaaa caagccaagc tacctcacgc aacatccct    900 tctgccacca gctccctgtc cccagggctg gcacccttca ctctgaagcc ggatgggacc    960
cgggtgctcc cgaacgtcat gtcccgcctc ccgagcgctt tgcttcctca ggccccgggc   1020
tcggtgctct tccagagccc tttctccact gtggcgctag acacatccaa gaaagggaag   1080
gggaagccac cgaacatctc cgcggtggat gtcaaaccca agacgaggc ggccctctac    1140 aagcacaagt gtaagtactg tagcaaggtt tttgggactg atagctcctt gcagatccac   1200
ctccgctccc acactggaga gagcccttc gtgtgctctg tctgtggtca tcgcttcacc    1260
accaagggca acctcaaggt gcactttcac cgacatcccc aggtgaaggc aaaccccccag  1320 ctgtttgccg agttccagga caaagtggcg gccggcaatg gcatccccta tgcactctct   1380
gtacctgacc ccatagatga accgagtctt tctttagaca gcaaacctgt ccttgtaacc   1440
acctctgtag ggctacctca gaatctttct tcggggacta atcccaagga cctcacgggt   1500
ggctccttgc ccggtgacct gcagcctggg ccttctccag aaagtgaggg tggacccaca   1560
ctccctgggg tgggaccaaa ctataattcc caagggctg gtggcttcca agggagtggg    1620
acccctgagc cagggtcaga gaccctgaaa ttgcagcagt tggtggagaa cattgacaag   1680
gccaccactg atcccaacga atgtctcatt tgccaccgag tcttaagctg tcagagctcc   1740
ctcaagatgc attatcgcac ccacaccggg gagagaccgt tccagtgtaa gatctgtggc   1800 cgagccttt ctaccaaagg taacctgaag acacaccttg gggttcaccg aaccaacaca    1860
tccattaaga cgcagcattc gtgccccatc tgccagaaga agttcactaa tgccgtgatg   1920
ctgcagcaac atattcggat gcacatgggc ggtcagattc ccaacacgcc cctgccagag   1980
aatccctgtg actttacggg ttctgagcca atgaccgtgg gtgagaacgg cagcaccggc   2040
gctatctgcc atgatgatgt catcgaaagc atcgatgtag aggaagtcag ctcccaggag   2100
gctcccagca gctcctccaa ggtccccacg cctcttccca gcatccactc ggcatcaccc   2160
acgctagggt ttgccatgat ggcttcctta gatgccccag ggaaagtggg tcctgcccct   2220
tttaacctgc agcgccaggg cagcagagaa acggttccg tggagagcga tggcttgacc    2280
aacgactcat cctcgctgat gggagaccag gagtatcaga gccgaagccc agatatcctg   2340
gaaaccacat ccttccaggc actctccccg gccaatagtc aagccgaaag catcaagtca   2400
aagtctcccg atgctgggag caaagcagag agctccgaga acagccgcac tgagatggaa   2460
ggtcggagca gtcccccttc cacgtttatc cgagccccgc cgacctatgt caaggttgaa   2520
gttcctggca catttgtggg accctcgaca ttgtccccag ggatgacccc tttgttagca   2580
gcccagccac gccgacaggc caagcaacat ggctgcacac ggtgtgggaa gaacttctcg   2640
tctgctagcg ctcttcagat ccacgagcgg actcacactg gagagaagcc ttttgtgtgc   2700
aacatttgtg ggcgagcttt taccaccaaa ggcaacttaa aggttcacta catgacacac   2760
ggggcgaaca ataactcagc ccgccgtgga aggaagttgg ccatcgagaa caccatggct   2820
ctgttaggta cggacggaaa aagagtctca gaaatctttc caaggaaat cctggcccct    2880 tcagtgaatg tggaccctgt tgtgtggaac cagtacacca gcatgctcaa tggcggtctg   2940
gccgtgaaga ccaatgagat ctctgtgatc cagagtgggg gggttcctac cctcccggtt   3000
tccttggggg ccacctccgt tgtgaataac gccactgtct ccaagatgga tggctcccag   3060
tcgggtatca gtgcagatgt ggaaaaacca agtgctactg acggcgttcc caaacaccag   3120
```
tttcctcact tcctggaaga aaacaagatt gcggtcagct aa              3162

<210> SEQ ID NO 18
<211> LENGTH: 1053
<212> TYPE: PRT
<213> ORGANISM: Homo sapiens

<400> SEQUENCE: 18

Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
            20                  25                  30

Ala Ala Pro Ala Ala Pro Ala Ala Gly Glu Leu Gly Ala Pro Val Asn
        35                  40                  45

His Pro Gly Asn Asp Glu Val Ala Ser Glu Asp Glu Ala Thr Val Lys
    50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Glu Gly Pro Val Pro Ser
            100                 105                 110

Glu Asp Phe Ser Gly Ala Val Leu Ser His Gln Pro Thr Ser Pro Gly
        115                 120                 125

Ser Lys Asp Cys His Arg Glu Asn Gly Gly Ser Ser Glu Asp Met Lys
    130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190

Val Asn Gln Arg Ser Ala Asp Ala Leu Pro Ala Pro Val Pro Gly Ala
        195                 200                 205

Asn Ser Ile Pro Trp Val Leu Glu Gln Ile Leu Cys Leu Gln Gln Gln
    210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Gly Ala Gly Ala Asp Thr
                245                 250                 255

Leu Lys Thr Leu Gly Ser His Met Ser Gln Gln Val Ser Ala Ala Val
            260                 265                 270

Ala Leu Leu Ser Gln Lys Ala Gly Ser Gln Gly Leu Ser Leu Asp Ala
        275                 280                 285

Leu Lys Gln Ala Lys Leu Pro His Ala Asn Ile Pro Ser Ala Thr Ser
    290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
            340                 345                 350

Leu Asp Thr Ser Lys Lys Gly Lys Gly Lys Pro Pro Asn Ile Ser Ala
        355                 360                 365

```
Val Asp Val Lys Pro Lys Asp Glu Ala Ala Leu Tyr Lys His Lys Cys
    370             375                 380

Lys Tyr Cys Ser Lys Val Phe Gly Thr Asp Ser Ser Leu Gln Ile His
385             390                 395                     400

Leu Arg Ser His Thr Gly Glu Arg Pro Phe Val Cys Ser Val Cys Gly
                405             410                 415

His Arg Phe Thr Thr Lys Gly Asn Leu Lys Val His Phe His Arg His
            420                 425                 430

Pro Gln Val Lys Ala Asn Pro Gln Leu Phe Ala Glu Phe Gln Asp Lys
            435                 440                 445

Val Ala Ala Gly Asn Gly Ile Pro Tyr Ala Leu Ser Val Pro Asp Pro
450                 455                 460

Ile Asp Glu Pro Ser Leu Ser Leu Asp Ser Lys Pro Val Leu Val Thr
465             470                 475                     480

Thr Ser Val Gly Leu Pro Gln Asn Leu Ser Ser Gly Thr Asn Pro Lys
                485                 490                 495

Asp Leu Thr Gly Gly Ser Leu Pro Gly Asp Leu Gln Pro Gly Pro Ser
            500                 505                 510

Pro Glu Ser Glu Gly Gly Pro Thr Leu Pro Gly Val Gly Pro Asn Tyr
            515                 520                 525

Asn Ser Pro Arg Ala Gly Gly Phe Gln Gly Ser Gly Thr Pro Glu Pro
530                 535                 540

Gly Ser Glu Thr Leu Lys Leu Gln Gln Leu Val Glu Asn Ile Asp Lys
545                 550                 555                 560

Ala Thr Thr Asp Pro Asn Glu Cys Leu Ile Cys His Arg Val Leu Ser
                565                 570                 575

Cys Gln Ser Ser Leu Lys Met His Tyr Arg Thr His Thr Gly Glu Arg
            580                 585                 590

Pro Phe Gln Cys Lys Ile Cys Gly Arg Ala Phe Ser Thr Lys Gly Asn
        595                 600                 605

Leu Lys Thr His Leu Gly Val His Arg Thr Asn Thr Ser Ile Lys Thr
    610                 615                 620

Gln His Ser Cys Pro Ile Cys Gln Lys Lys Phe Thr Asn Ala Val Met
625                 630                 635                 640

Leu Gln Gln His Ile Arg Met His Met Gly Gly Gln Ile Pro Asn Thr
                645                 650                 655

Pro Leu Pro Glu Asn Pro Cys Asp Phe Thr Gly Ser Glu Pro Met Thr
            660                 665                 670

Val Gly Glu Asn Gly Ser Thr Gly Ala Ile Cys His Asp Asp Val Ile
            675                 680                 685

Glu Ser Ile Asp Val Glu Glu Val Ser Ser Gln Glu Ala Pro Ser Ser
    690                 695                 700

Ser Ser Lys Val Pro Thr Pro Leu Pro Ser Ile His Ser Ala Ser Pro
705                 710                 715                 720

Thr Leu Gly Phe Ala Met Met Ala Ser Leu Asp Ala Pro Gly Lys Val
                725                 730                 735

Gly Pro Ala Pro Phe Asn Leu Gln Arg Gln Gly Ser Arg Glu Asn Gly
            740                 745                 750

Ser Val Glu Ser Asp Gly Leu Thr Asn Asp Ser Ser Ser Leu Met Gly
            755                 760                 765

Asp Gln Glu Tyr Gln Ser Arg Ser Pro Asp Ile Leu Glu Thr Thr Ser
770                 775                 780

Phe Gln Ala Leu Ser Pro Ala Asn Ser Gln Ala Glu Ser Ile Lys Ser
```

```
                785                 790                 795                 800
Lys Ser Pro Asp Ala Gly Ser Lys Ala Glu Ser Ser Glu Asn Ser Arg
                    805                 810                 815
Thr Glu Met Glu Gly Arg Ser Ser Leu Pro Ser Thr Phe Ile Arg Ala
                820                 825                 830
Pro Pro Thr Tyr Val Lys Val Glu Val Pro Gly Thr Phe Val Gly Pro
                835                 840                 845
Ser Thr Leu Ser Pro Gly Met Thr Pro Leu Leu Ala Ala Gln Pro Arg
        850                 855                 860
Arg Gln Ala Lys Gln His Gly Cys Thr Arg Cys Gly Lys Asn Phe Ser
865                 870                 875                 880
Ser Ala Ser Ala Leu Gln Ile His Glu Arg Thr His Thr Gly Glu Lys
                885                 890                 895
Pro Phe Val Cys Asn Ile Cys Gly Arg Ala Phe Thr Thr Lys Gly Asn
                900                 905                 910
Leu Lys Val His Tyr Met Thr His Gly Ala Asn Asn Asn Ser Ala Arg
                915                 920                 925
Arg Gly Arg Lys Leu Ala Ile Glu Asn Thr Met Ala Leu Leu Gly Thr
        930                 935                 940
Asp Gly Lys Arg Val Ser Glu Ile Phe Pro Lys Glu Ile Leu Ala Pro
945                 950                 955                 960
Ser Val Asn Val Asp Pro Val Val Trp Asn Gln Tyr Thr Ser Met Leu
                965                 970                 975
Asn Gly Gly Leu Ala Val Lys Thr Asn Glu Ile Ser Val Ile Gln Ser
                980                 985                 990
Gly Gly Val Pro Thr Leu Pro Val  Ser Leu Gly Ala Thr  Ser Val Val
        995                 1000                1005
Asn Asn  Ala Thr Val Ser Lys  Met Asp Gly Ser Gln  Ser Gly Ile
        1010                1015                1020
Ser Ala Asp Val Glu Lys Pro  Ser Ala Thr Asp Gly  Val Pro Lys
        1025                1030                1035
His Gln  Phe Pro His Phe Leu  Glu Glu Asn Lys Ile  Ala Val Ser
        1040                1045                1050

<210> SEQ ID NO 19
<211> LENGTH: 1173
<212> TYPE: DNA
<213> ORGANISM: Homo sapiens

<400> SEQUENCE: 19
atggcgcaaa ggtacgacga tctaccccat tacgggggca tggatggagt aggcatcccc       60
tccacgatgt atgggacccc gcatgcagcc aggtccatgc agccggtcca ccacctgaac      120
cacgggcctc ctctgcactc gcatcagtac ccgcacacag ctcataccaa cgccatggcc      180
cccagcatgg gctcctctgt caatgacgct ttaaagagag ataaagatgc catttatgga      240
caccccctct tccctctctt agcactgatt tttgagaaat gtgaattagc tacttgtacc      300
ccccgcgagc cgggggtggc gggcgggac gtctgctcgt cagagtcatt caatgaagat      360
atagccgtgt cgccaaaaca gattcgcgca gaaaaacctc tatttttcttc taatccagaa      420 ctggataact tgatgattca agccatacaa gtattaaggt ttcatctatt ggaattagag      480
aaggtacacg aattatgtga caatttctgc caccggtata ttagctgttt gaaagggaaa      540
atgcctatcg atttggtgat agacgataga aaggaggat caaaatcaga cagtgaagat      600
ataacaagat cagcaaatct aactgaccag ccctcttgga acagagatca tgatgacacg      660
```

```
gcatctactc gttcaggagg aaccccaggc ccttccagcg gtggccacac gtcacacagt    720
ggggacaaca gcagtgagca aggtgatggc ttggacaaca gtgtagcttc ccccagcaca    780
ggtgacgatg atgaccctga taaggacaaa aagcgtcaca aaaagcgtgg catctttccc    840
aaagtagcca caaatatcat gagggcgtgg ctgttccagc atctaacaca cccttaccct    900
tctgaagaac agaaaaagca gttggcacaa gacacgggac tcaccatcct tcaagtgaac    960
aattggttta ttaatgcccg gagaagaata gtgcagccca tgatagacca gtccaaccga   1020
gcagtaagtc aaggaacacc ttataatcct gatggacagc ccatgggagg tttcgtaatg   1080
gacggtcagc aacatatggg aattagagca ccaggaccta tgagtggaat gggcatgaat   1140
atgggcatgg aggggcagtg gcactacatg taa                                1173
```

<210> SEQ ID NO 20
<211> LENGTH: 390
<212> TYPE: PRT
<213> ORGANISM: Homo sapiens

<400> SEQUENCE: 20

```
Met Ala Gln Arg Tyr Asp Asp Leu Pro His Tyr Gly Gly Met Asp Gly
1               5                   10                  15

Val Gly Ile Pro Ser Thr Met Tyr Gly Asp Pro His Ala Ala Arg Ser
            20                  25                  30

Met Gln Pro Val His His Leu Asn His Gly Pro Pro Leu His Ser His
        35                  40                  45

Gln Tyr Pro His Thr Ala His Thr Asn Ala Met Ala Pro Ser Met Gly
    50                  55                  60

Ser Ser Val Asn Asp Ala Leu Lys Arg Asp Lys Asp Ala Ile Tyr Gly
65                  70                  75                  80

His Pro Leu Phe Pro Leu Leu Ala Leu Ile Phe Glu Lys Cys Glu Leu
                85                  90                  95

Ala Thr Cys Thr Pro Arg Glu Pro Gly Val Ala Gly Gly Asp Val Cys
            100                 105                 110

Ser Ser Glu Ser Phe Asn Glu Asp Ile Ala Val Phe Ala Lys Gln Ile
        115                 120                 125

Arg Ala Glu Lys Pro Leu Phe Ser Ser Asn Pro Glu Leu Asp Asn Leu
    130                 135                 140

Met Ile Gln Ala Ile Gln Val Leu Arg Phe His Leu Leu Glu Leu Glu
145                 150                 155                 160

Lys Val His Glu Leu Cys Asp Asn Phe Cys His Arg Tyr Ile Ser Cys
                165                 170                 175

Leu Lys Gly Lys Met Pro Ile Asp Leu Val Ile Asp Asp Arg Glu Gly
            180                 185                 190

Gly Ser Lys Ser Asp Ser Glu Asp Ile Thr Arg Ser Ala Asn Leu Thr
        195                 200                 205

Asp Gln Pro Ser Trp Asn Arg Asp His Asp Asp Thr Ala Ser Thr Arg
    210                 215                 220

Ser Gly Gly Thr Pro Gly Pro Ser Ser Gly Gly His Thr Ser His Ser
225                 230                 235                 240

Gly Asp Asn Ser Ser Glu Gln Gly Asp Gly Leu Asp Asn Ser Val Ala
                245                 250                 255

Ser Pro Ser Thr Gly Asp Asp Asp Pro Asp Lys Asp Lys Lys Arg
            260                 265                 270

His Lys Lys Arg Gly Ile Phe Pro Lys Val Ala Thr Asn Ile Met Arg
```

```
                 275                 280                 285
Ala Trp Leu Phe Gln His Leu Thr His Pro Tyr Pro Ser Glu Glu Gln
         290                 295                 300

Lys Lys Gln Leu Ala Gln Asp Thr Gly Leu Thr Ile Leu Gln Val Asn
305                 310                 315                 320

Asn Trp Phe Ile Asn Ala Arg Arg Arg Ile Val Gln Pro Met Ile Asp
             325                 330                 335

Gln Ser Asn Arg Ala Val Ser Gln Gly Thr Pro Tyr Asn Pro Asp Gly
             340                 345                 350

Gln Pro Met Gly Gly Phe Val Met Asp Gly Gln Gln His Met Gly Ile
             355                 360                 365

Arg Ala Pro Gly Pro Met Ser Gly Met Gly Met Asn Met Gly Met Glu
         370                 375                 380

Gly Gln Trp His Tyr Met
385                 390

<210> SEQ ID NO 21
<211> LENGTH: 1521
<212> TYPE: DNA
<213> ORGANISM: Homo sapiens

<400> SEQUENCE: 21
atggcttctg gggacccttta cgaggttgaa aggattgtag acaagaggaa gaacaagaaa      60
ggaaaatggg agtatcttat ccgatggaaa ggctacggga gcaccgagga cacgtgggag     120
ccggagcacc acctcttgca ctgtgaggag tttattgatg aattcaatgg gttgcacatg     180
tccaaggaca gaggatcaa gtcagggaag cagtccagta cctccaagct gctgcgtgac      240
agtcgaggcc cgtcggttga gaaactgtcc cacagacctt cagatcctgg aaagagcaag     300
gggacctccc ataaacggaa gcgaattaac cctcccctgg ccaagccaaa aaagggtat     360 tcaggcaagc cctcttcagg aggtgacagg gccaccaaga cggtgtctta caggactacc     420
cccagtggtt tgcaaataat gcccctgaaa agtctcaga cgggatgga aaatgggac       480 gccggctctg agaaggatga gaggcacttt ggaaatgggt cccatcagcc tggcttggat     540
ttgaatgatc atgttggaga gcaagatatg ggtgaatgtg acgtgaatca cgctacactg     600
gcggagaacg ggctcggctc tgctctgacc aacgggggat tgaacctgca cagtccagtg     660
aagaggaagc tggaagcgga aaggactac gtctttgaca aaaggctcag atacagtgtc     720
cgccagaatg aaagcaactg tcggtttcga cacatcgttg tgcggaagga agaagggttc     780
acgcacatcc tgctgtccag tcagacctcg gataacaatg ccctgacacc tgagatcatg     840
aaagaagtcc ggcgagcgct ctgcaacgca gccacagacg acagcaaact gctgctcctc     900
agcgcagtgg ggagcgtgtt ctgcagcggc ctggattatt cctacctaat ggccggttg    960 tccagcgacc ggcgaaagga gagcactcgg attgcagaag ccatcaggga ctttgtgaag    1020
gcctttatcc agtttaagaa gcctatcgtg gtggccatca atgggccggc cctgggcctg    1080
ggtgcctcca tcctgccct ctgtgacatc gtgtgggcca gtgagaaggc ctggttccag    1140
acgccctacg ccaccatccg cctcacgcct gctggctgct cctcctacac cttccccag     1200 atcctgggcg tcgcgctggc caatgagatg ctgttctgtg gcggaagct caccgcccag   1260 gaggcctgca gcaggggct ggtgtcgcag gtcttctggc ccaccacgtt cagccaggag   1320
gtcatgctgc gggtcaagga gatggcatcc tgcagtgccg tggtgttaga ggagtccaaa  1380
tgcctcgtgc ggagcttcct gaaatcagtg ctggaagacg tgaacgagaa ggaatgcctc  1440
```

```
atgctcaagc agctctggag ctcctccaaa ggccttgact cccttttcag ctacctgcag    1500
gacaaaattt atgaagtctg a                                              1521
```

<210> SEQ ID NO 22
<211> LENGTH: 506
<212> TYPE: PRT
<213> ORGANISM: Homo sapiens

<400> SEQUENCE: 22

```
Met Ala Ser Gly Asp Leu Tyr Glu Val Glu Arg Ile Val Asp Lys Arg
1               5                   10                  15

Lys Asn Lys Lys Gly Lys Trp Glu Tyr Leu Ile Arg Trp Lys Gly Tyr
            20                  25                  30

Gly Ser Thr Glu Asp Thr Trp Glu Pro Glu His His Leu Leu His Cys
        35                  40                  45

Glu Glu Phe Ile Asp Glu Phe Asn Gly Leu His Met Ser Lys Asp Lys
    50                  55                  60

Arg Ile Lys Ser Gly Lys Gln Ser Ser Thr Ser Lys Leu Leu Arg Asp
65                  70                  75                  80

Ser Arg Gly Pro Ser Val Glu Lys Leu Ser His Arg Pro Ser Asp Pro
                85                  90                  95

Gly Lys Ser Lys Gly Thr Ser His Lys Arg Lys Arg Ile Asn Pro Pro
            100                 105                 110

Leu Ala Lys Pro Lys Lys Gly Tyr Ser Gly Lys Pro Ser Ser Gly Gly
        115                 120                 125

Asp Arg Ala Thr Lys Thr Val Ser Tyr Arg Thr Thr Pro Ser Gly Leu
130                 135                 140

Gln Ile Met Pro Leu Lys Lys Ser Gln Asn Gly Met Glu Asn Gly Asp
145                 150                 155                 160

Ala Gly Ser Glu Lys Asp Glu Arg His Phe Gly Asn Gly Ser His Gln
                165                 170                 175

Pro Gly Leu Asp Leu Asn Asp His Val Gly Glu Gln Asp Met Gly Glu
            180                 185                 190

Cys Asp Val Asn His Ala Thr Leu Ala Glu Asn Gly Leu Gly Ser Ala
        195                 200                 205

Leu Thr Asn Gly Gly Leu Asn Leu His Ser Pro Val Lys Arg Lys Leu
210                 215                 220

Glu Ala Glu Lys Asp Tyr Val Phe Asp Lys Arg Leu Arg Tyr Ser Val
225                 230                 235                 240

Arg Gln Asn Glu Ser Asn Cys Arg Phe Arg Asp Ile Val Val Arg Lys
                245                 250                 255

Glu Glu Gly Phe Thr His Ile Leu Leu Ser Ser Gln Thr Ser Asp Asn
            260                 265                 270

Asn Ala Leu Thr Pro Glu Ile Met Lys Glu Val Arg Arg Ala Leu Cys
        275                 280                 285

Asn Ala Ala Thr Asp Asp Ser Lys Leu Leu Leu Ser Ala Val Gly
        290                 295                 300

Ser Val Phe Cys Ser Gly Leu Asp Tyr Ser Tyr Leu Ile Gly Arg Leu
305                 310                 315                 320

Ser Ser Asp Arg Arg Lys Glu Ser Thr Arg Ile Ala Glu Ala Ile Arg
                325                 330                 335

Asp Phe Val Lys Ala Phe Ile Gln Phe Lys Lys Pro Ile Val Val Ala
            340                 345                 350

Ile Asn Gly Pro Ala Leu Gly Leu Gly Ala Ser Ile Leu Pro Leu Cys
```

```
                355                 360                 365
Asp Ile Val Trp Ala Ser Glu Lys Ala Trp Phe Gln Thr Pro Tyr Ala
    370                 375                 380

Thr Ile Arg Leu Thr Pro Ala Gly Cys Ser Ser Tyr Thr Phe Pro Gln
385                 390                 395                 400

Ile Leu Gly Val Ala Leu Ala Asn Glu Met Leu Phe Cys Gly Arg Lys
                405                 410                 415

Leu Thr Ala Gln Glu Ala Cys Ser Arg Gly Leu Val Ser Gln Val Phe
            420                 425                 430

Trp Pro Thr Thr Phe Ser Gln Glu Val Met Leu Arg Val Lys Glu Met
        435                 440                 445

Ala Ser Cys Ser Ala Val Val Leu Glu Glu Ser Lys Cys Leu Val Arg
    450                 455                 460

Ser Phe Leu Lys Ser Val Leu Glu Asp Val Asn Glu Lys Glu Cys Leu
465                 470                 475                 480

Met Leu Lys Gln Leu Trp Ser Ser Ser Lys Gly Leu Asp Ser Leu Phe
                485                 490                 495

Ser Tyr Leu Gln Asp Lys Ile Tyr Glu Val
            500                 505

<210> SEQ ID NO 23
<211> LENGTH: 1461
<212> TYPE: DNA
<213> ORGANISM: Homo sapiens

<400> SEQUENCE: 23
```

| | | | | | |
|---|---|---|---|---|---|
| atgattcaga | ctgtcccgga | cccagcagct | catatcaagg | aagccttatc | agttgtgagt | 60 |
| gaggaccagt | cgttgtttga | gtgtgcctac | ggaacgccac | acctggctaa | gacagagatg | 120 |
| accgcgtcct | cctccagcga | ctatggacag | acttccaaga | tgagcccacg | cgtccctcag | 180 |
| caggattggc | tgtctcaacc | cccagccagg | gtcaccatca | aaatggaatg | taaccctagc | 240 |
| caggtgaatg | gctcaaggaa | ctctcctgat | gaatgcagtg | tggccaaagg | cgggaagatg | 300 |
| gtgggcagcc | cagacaccgt | tgggatgaac | tacggcagct | acatggagga | gaagcacatg | 360 |
| ccaccccaa | acatgaccac | gaacgagcgc | agagttatcg | tgccagcaga | tcctacgcta | 420 |
| tggagtacag | accatgtgcg | gcagtggctg | gagtgggcgg | tgaaagaata | tggccttcca | 480 |
| gacgtcaaca | tcttgttatt | ccagaacatc | gatgggaagg | aactgtgcaa | gatgaccaag | 540 |
| gacgacttcc | agaggctcac | ccccagctac | aacgccgaca | tccttctctc | acatctccac | 600 |
| tacctcagag | agactcctct | tccacatttg | acttcagatg | atgttgataa | agccttacaa | 660 |
| aactctccac | ggttaatgca | tgctagaaac | acaggggtg | cagcttttat | tttcccaaat | 720 |
| acttcagtat | atcctgaagc | tacgcaaaga | attacaacta | ggccagattt | accatatgag | 780 |
| ccccccagga | gatcagcctg | gaccggtcac | ggccacccca | cgcccagtc | gaaagctgct | 840 |
| caaccatctc | cttccacagt | gcccaaaact | gaagaccagc | gtcctcagtt | agatccttat | 900 |
| cagattcttg | gaccaacaag | tagccgcctt | gcaaatccag | gcagtggcca | gatccagctt | 960 |
| tggcagttcc | tcctggagct | cctgtcggac | agctccaact | ccagctgcat | cacctgggaa | 1020 |
| ggcaccaacg | gggagttcaa | gatgacggat | cccgacgagg | tggcccggcg | ctggggagag | 1080 |
| cggaagagca | aacccaacat | gaactacgat | aagctcagcc | gcgccctccg | ttactactat | 1140 |
| gacaagaaca | tcatgaccaa | ggtccatggg | aagcgctacg | cctacaagtt | cgacttccac | 1200 |
| gggatcgccc | aggccctcca | gccccacccc | ccggagtcat | ctctgtacaa | gtaccctca | 1260 |

-continued

```
gacctcccgt acatgggctc ctatcacgcc cacccacaga agatgaactt tgtggcgccc    1320
caccctccag ccctccccgt gacatcttcc agttttttttg ctgccccaaa cccatactgg    1380
aattcaccaa ctgggggtat ataccccaac actaggctcc ccaccagcca tatgccttct    1440
catctgggca cttactacta a                                              1461
```

<210> SEQ ID NO 24
<211> LENGTH: 486
<212> TYPE: PRT
<213> ORGANISM: Homo sapiens

<400> SEQUENCE: 24

```
Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Gly His
            260                 265                 270

Pro Thr Pro Gln Ser Lys Ala Ala Gln Pro Ser Pro Ser Thr Val Pro
        275                 280                 285

Lys Thr Glu Asp Gln Arg Pro Gln Leu Asp Pro Tyr Gln Ile Leu Gly
    290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335
```

```
Ile Thr Trp Glu Gly Thr Asn Gly Glu Phe Lys Met Thr Asp Pro Asp
                    340                 345                 350

Glu Val Ala Arg Arg Trp Gly Arg Lys Ser Lys Pro Asn Met Asn
            355                 360                 365

Tyr Asp Lys Leu Ser Arg Ala Leu Arg Tyr Tyr Asp Lys Asn Ile
        370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Glu Ser Ser Leu Tyr
                405                 410                 415

Lys Tyr Pro Ser Asp Leu Pro Tyr Met Gly Ser Tyr His Ala His Pro
        420                 425                 430

Gln Lys Met Asn Phe Val Ala Pro His Pro Pro Ala Leu Pro Val Thr
            435                 440                 445

Ser Ser Ser Phe Phe Ala Ala Pro Asn Pro Tyr Trp Asn Ser Pro Thr
        450                 455                 460

Gly Gly Ile Tyr Pro Asn Thr Arg Leu Pro Thr Ser His Met Pro Ser
465                 470                 475                 480

His Leu Gly Thr Tyr Tyr
                485

<210> SEQ ID NO 25
<211> LENGTH: 816
<212> TYPE: DNA
<213> ORGANISM: Homo sapiens

<400> SEQUENCE: 25
atgttacagg cgtgcaaaat ggaagggttt cccctcgtcc ccctcagcc atcagaagac      60
ctggtgccct atgacacgga tctataccaa cgccaaacgc acgagtatta ccctatctc    120
agcagtgatg gggagagcca tagcgaccat tactgggact ccacccca ccacgtgcac      180
agcgagttcg agagcttcgc cgagaacaac ttcacggagc tccagagcgt gcagcccccg    240
cagctgcagc agctctaccg ccacatggag ctggagcaga tgcacgtcct cgatacccc    300
atggtgccac cccatcccag tcttggccac caggtctcct acctgccccg gatgtgcctc    360
cagtacccat ccctgtcccc agcccagccc agctcagatg aggaggaggg cgagcggcag    420
agcccccac tggaggtgtc tgacggcgag gcggatggcc tggagcccgg gcctgggctc    480
ctgcctgggg agacaggcag caagaagaag atccgcctgt accagttcct gttggacctg    540
ctccgcagcg gcgacatgaa ggacagcatc tggtgggtgg acaaggacaa gggcaccttc    600
cagttctcgt ccaagcacaa ggaggcgctg gcgcaccgct ggggcatcca gaagggcaac    660
cgcaagaaga tgacctacca gaagatggcg cgcgcgctgc gcaactacgg caagacgggc    720
gaggtcaaga aggtgaagaa gaagctcacc taccagttca gcggcgaagt gctgggccgc    780
gggggcctgg ccgagcggcg ccaccgcc cactga                                816

<210> SEQ ID NO 26
<211> LENGTH: 271
<212> TYPE: PRT
<213> ORGANISM: Homo sapiens

<400> SEQUENCE: 26

Met Leu Gln Ala Cys Lys Met Glu Gly Phe Pro Leu Val Pro Pro Gln
1               5                   10                  15

Pro Ser Glu Asp Leu Val Pro Tyr Asp Thr Asp Leu Tyr Gln Arg Gln
            20                  25                  30
```

| | | | | | | | | | | | | |
|---|---|---|---|---|---|---|---|---|---|---|---|---|
|Thr|His|Glu|Tyr|Tyr|Pro|Tyr|Leu|Ser|Ser|Asp|Gly|Glu|Ser|His|Ser|
| | |35| | | |40| | | |45| | | | | |

Asp His Tyr Trp Asp Phe His Pro His Val His Ser Glu Phe Glu
    50              55              60

Ser Phe Ala Glu Asn Asn Phe Thr Glu Leu Gln Ser Val Gln Pro Pro
65              70              75              80

Gln Leu Gln Gln Leu Tyr Arg His Met Glu Leu Glu Gln Met His Val
            85              90              95

Leu Asp Thr Pro Met Val Pro Pro His Pro Ser Leu Gly His Gln Val
            100             105             110

Ser Tyr Leu Pro Arg Met Cys Leu Gln Tyr Pro Ser Leu Ser Pro Ala
            115             120             125

Gln Pro Ser Ser Asp Glu Glu Gly Glu Arg Gln Ser Pro Pro Leu
        130             135             140

Glu Val Ser Asp Gly Glu Ala Asp Gly Leu Glu Pro Gly Pro Gly Leu
145             150             155             160

Leu Pro Gly Glu Thr Gly Ser Lys Lys Lys Ile Arg Leu Tyr Gln Phe
                165             170             175

Leu Leu Asp Leu Leu Arg Ser Gly Asp Met Lys Asp Ser Ile Trp Trp
            180             185             190

Val Asp Lys Asp Lys Gly Thr Phe Gln Phe Ser Ser Lys His Lys Glu
            195             200             205

Ala Leu Ala His Arg Trp Gly Ile Gln Lys Gly Asn Arg Lys Lys Met
            210             215             220

Thr Tyr Gln Lys Met Ala Arg Ala Leu Arg Asn Tyr Gly Lys Thr Gly
225             230             235             240

Glu Val Lys Lys Val Lys Lys Lys Leu Thr Tyr Gln Phe Ser Gly Glu
                245             250             255

Val Leu Gly Arg Gly Gly Leu Ala Glu Arg Arg His Pro Pro His
            260             265             270

<210> SEQ ID NO 27
<211> LENGTH: 828
<212> TYPE: DNA
<213> ORGANISM: Homo sapiens

<400> SEQUENCE: 27

```
atgcccaaag tcttcctggt gaagaggagg agcctggggg tctcggtccg cagctgggat     60
gagctcccgg atgagaaaag ggcagacacc tacatcccag tgggcctagg ccgcctgctc    120
cacgaccccc ccgaggactg ccgcagcgac ggcggcagca gcagcggcag cggcagcagc    180
agcgcggggg agcctggagg agcagagagc agctcgtccc cgcacgcccc cgagagcgaa    240
accccgagc  ccggcgacgc cgagggcccc gatggacacc tggcgaccaa gcagcgcccg    300
gtcgccagat cgaaaatcaa gttcaccaca ggcacgtgca cgactcggt  ggttcacagc    360
tgtgacctgt gtggcaaggg cttccgtctg cagcgcatgc tgaaccgtca cctcaagtgc    420
cacaaccagg tgaaaagaca cctgtgcacc ttctgcggca agggcttcaa cgacaccttc    480
gacctgaaga ggcacgtccg cacacacaca ggcattcgtc cctacaaatg caacgtctgc    540
aataaagcct tcacccagcg ctgctctctg gagtccaccc tgaagaaaat ccatgggtg    600
cagcagcagt atgcctataa gcagcggcgg gacaagctct acgtctgcga ggattgcggc    660
tacacgggcc ccacccagga ggacctgtac ctgcacgtga acagtgccca tccgggcagc    720
tcgtttctca aaaagacatc taaaaaactg gcagcccttc tgcagggcaa gctgacatcc    780
```
gcacaccagg agaataccag cctgagtgag gaggaggaga ggaagtga        828

<210> SEQ ID NO 28
<211> LENGTH: 275
<212> TYPE: PRT
<213> ORGANISM: Homo sapiens

<400> SEQUENCE: 28

```
Met Pro Lys Val Phe Leu Val Lys Arg Arg Ser Leu Gly Val Ser Val
1               5                   10                  15

Arg Ser Trp Asp Glu Leu Pro Asp Glu Lys Arg Ala Asp Thr Tyr Ile
            20                  25                  30

Pro Val Gly Leu Gly Arg Leu Leu His Asp Pro Pro Glu Asp Cys Arg
        35                  40                  45

Ser Asp Gly Gly Ser Ser Gly Ser Gly Ser Ser Ala Gly Glu
    50                  55                  60

Pro Gly Gly Ala Glu Ser Ser Ser Pro His Ala Pro Glu Ser Glu
65                  70                  75                  80

Thr Pro Glu Pro Gly Asp Ala Glu Gly Pro Asp Gly His Leu Ala Thr
                85                  90                  95

Lys Gln Arg Pro Val Ala Arg Ser Lys Ile Lys Phe Thr Thr Gly Thr
            100                 105                 110

Cys Ser Asp Ser Val Val His Ser Cys Asp Leu Cys Gly Lys Gly Phe
        115                 120                 125

Arg Leu Gln Arg Met Leu Asn Arg His Leu Lys Cys His Asn Gln Val
    130                 135                 140

Lys Arg His Leu Cys Thr Phe Cys Gly Lys Gly Phe Asn Asp Thr Phe
145                 150                 155                 160

Asp Leu Lys Arg His Val Arg Thr His Thr Gly Ile Arg Pro Tyr Lys
                165                 170                 175

Cys Asn Val Cys Asn Lys Ala Phe Thr Gln Arg Cys Ser Leu Glu Ser
            180                 185                 190

His Leu Lys Lys Ile His Gly Val Gln Gln Gln Tyr Ala Tyr Lys Gln
        195                 200                 205

Arg Arg Asp Lys Leu Tyr Val Cys Glu Asp Cys Gly Tyr Thr Gly Pro
    210                 215                 220

Thr Gln Glu Asp Leu Tyr Leu His Val Asn Ser Ala His Pro Gly Ser
225                 230                 235                 240

Ser Phe Leu Lys Lys Thr Ser Lys Leu Ala Ala Leu Leu Gln Gly
                245                 250                 255

Lys Leu Thr Ser Ala His Gln Glu Asn Thr Ser Leu Ser Glu Glu
            260                 265                 270

Glu Arg Lys
        275
```

<210> SEQ ID NO 29
<211> LENGTH: 942
<212> TYPE: DNA
<213> ORGANISM: Homo sapiens

<400> SEQUENCE: 29
atgtacgtga gctacctcct ggacaaggac gtgagcatgt accctagctc cgtgcgccac        60
tctggcggcc tcaacctggc gccgcagaac ttcgtcagcc cccgcagta cccggactac       120 ggcggttacc acgtggcggc cgcagctgca gcggcagcga acttggacag cgcgcagtcc       180

```
ccggggccat cctggccggc agcgtatggc gccccactcc gggaggactg gaatggctac    240
gcgcccggag gcgccgcggc cgccgccaac gccgtggctc acggcctcaa cggtggctcc    300
ccggccgcag ccatgggcta cagcagcccc gcagactacc atccgcacca ccacccgcat    360
caccacccgc accacccggc cgccgcgcct tcctgcgctt ctgggctgct gcaaacgctc    420
aaccccggcc ctcctgggcc cgccgccacc gctgccgccg agcagctgtc tcccggcggc    480
cagcggcgga acctgtgcga gtggatgcgg aagccggcgc agcagtccct cggcagccaa    540
gtgaaaacca ggacgaaaga caaatatcga gtggtgtaca cggaccacca gcggctggag    600
ctggagaagg agtttcacta cagtcgctac atcaccatcc ggaggaaagc cgagctagcc    660
gccacgctgg ggctctctga gaggcaggtt aaaatctggt ttcagaaccg cagagcaaag    720
gagaggaaaa tcaacaagaa gaagttgcag cagcaacagc agcagcagcc accacagccg    780
cctccgccgc caccacagcc tccccagcct cagccaggtc ctctgagaag tgtcccagag    840
cccttgagtc cggtgtcttc cctgcaagcc tcagtgcctg gctctgtccc tggggttctg    900
gggccaactg ggggggtgct aaaccccacc gtcacccagt ga                       942
```

```

<210> SEQ ID NO 30
<211> LENGTH: 313
<212> TYPE: PRT
<213> ORGANISM: Homo sapiens

<400> SEQUENCE: 30

Met Tyr Val Ser Tyr Leu Leu Asp Lys Asp Val Ser Met Tyr Pro Ser
1               5                   10                  15

Ser Val Arg His Ser Gly Gly Leu Asn Leu Ala Pro Gln Asn Phe Val
            20                  25                  30

Ser Pro Pro Gln Tyr Pro Asp Tyr Gly Gly Tyr His Val Ala Ala Ala
        35                  40                  45

Ala Ala Ala Ala Ala Asn Leu Asp Ser Ala Gln Ser Pro Gly Pro Ser
    50                  55                  60

Trp Pro Ala Ala Tyr Gly Ala Pro Leu Arg Glu Asp Trp Asn Gly Tyr
65                  70                  75                  80

Ala Pro Gly Gly Ala Ala Ala Ala Asn Ala Val Ala His Gly Leu
                85                  90                  95

Asn Gly Gly Ser Pro Ala Ala Ala Met Gly Tyr Ser Ser Pro Ala Asp
            100                 105                 110

Tyr His Pro His His His Pro His His His Pro His His Pro Ala Ala
        115                 120                 125

Ala Pro Ser Cys Ala Ser Gly Leu Leu Gln Thr Leu Asn Pro Gly Pro
    130                 135                 140

Pro Gly Pro Ala Ala Thr Ala Ala Ala Glu Gln Leu Ser Pro Gly Gly
145                 150                 155                 160

Gln Arg Arg Asn Leu Cys Glu Trp Met Arg Lys Pro Ala Gln Gln Ser
                165                 170                 175

Leu Gly Ser Gln Val Lys Thr Arg Thr Lys Asp Lys Tyr Arg Val Val
            180                 185                 190

Tyr Thr Asp His Gln Arg Leu Glu Leu Glu Lys Glu Phe His Tyr Ser
        195                 200                 205

Arg Tyr Ile Thr Ile Arg Arg Lys Ala Glu Leu Ala Ala Thr Leu Gly
    210                 215                 220

Leu Ser Glu Arg Gln Val Lys Ile Trp Phe Gln Asn Arg Arg Ala Lys
225                 230                 235                 240
```

Glu Arg Lys Ile Asn Lys Lys Lys Leu Gln Gln Gln Gln Gln Gln
            245                 250                 255

Pro Pro Gln Pro Pro Pro Pro Pro Gln Pro Gln Pro Gln Pro
        260                 265                 270

Gly Pro Leu Arg Ser Val Pro Glu Pro Leu Ser Pro Val Ser Ser Leu
        275                 280                 285

Gln Ala Ser Val Pro Gly Ser Val Pro Gly Val Leu Gly Pro Thr Gly
        290                 295                 300

Gly Val Leu Asn Pro Thr Val Thr Gln
305                 310

<210> SEQ ID NO 31
<211> LENGTH: 1038
<212> TYPE: DNA
<213> ORGANISM: Homo sapiens

<400> SEQUENCE: 31

```
atgcaacgcc tggtggcctg ggacccagca tgtctccccc tgccgccgcc gccgcctgcc      60
tttaaatcca tggaagtggc caacttctac tacgaggcgg actgcttggc tgctgcgtac     120
ggcggcaagg cggcccccgc ggcgcccccc gcggccagac ccggccgcg cccccccgcc      180
ggcgagctgg gcagcatcgg cgaccacgag cgcgccatcg acttcagccc gtacctggag     240
ccgctgggcg cgccgcaggc cccggcgccc gccacggcca cggacacctt cgaggcggct     300
ccgccccgcgc ccgccccgc gccgcctcc tccgggcagc accacgactt cctctccgac     360
ctcttctccg acgactacgg gggcaagaac tgcaagaagc cggccgagta cggctacgtg     420
agcctggggc gcctggggc cgccaagggc gcgctgcacc ccggctgctt cgcgcccctg     480
cacccaccgc cccgccgcc gccgccgcc gccgagctca aggcggagcc gggcttcgag      540
cccgcggact gcaagcggaa ggaggaggcc ggggcgccgg gcggcggcgc aggcatggcg     600
gcgggcttcc cgtacgcgct gcgcgcttac ctcggctacc aggcggtgcc gagcggcagc     660
agcgggagcc tctccacgtc ctcctcgtcc agcccgcccg gcacgccgag cccgctgac     720
gccaaggcgc cccgaccgc ctgctacgcg ggggccgcgc cggcgccctc gcaggtcaag     780
agcaaggcca agaagaccgt ggacaagcac agcgacgagt acaagatccg cgcgagcgc     840
aacaacatcg ccgtgcgcaa gagccgcgac aaggccaaga tgcgcaacct ggagacgcag     900
cacaaggtcc tggagctcac ggccgagaac gagcggctgc agaagaaggt ggagcagctg     960
tcgcgcgagc tcagcaccct gcggaacttg ttcaagcagc tgcccgagcc cctgctcgcc    1020
tcctccggcc actgctag                                                  1038
```

<210> SEQ ID NO 32
<211> LENGTH: 345
<212> TYPE: PRT
<213> ORGANISM: Homo sapiens

<400> SEQUENCE: 32

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

```
Ser Ile Gly Asp His Glu Arg Ala Ile Asp Phe Ser Pro Tyr Leu Glu
 65                  70                  75                  80

Pro Leu Gly Ala Pro Gln Ala Pro Ala Pro Thr Ala Thr Asp Thr
                 85                  90                  95

Phe Glu Ala Ala Pro Ala Pro Ala Pro Ala Pro Ala Ser Ser Gly
            100                 105                 110

Gln His His Asp Phe Leu Ser Asp Leu Phe Ser Asp Tyr Gly Gly
        115                 120                 125

Lys Asn Cys Lys Lys Pro Ala Glu Tyr Gly Tyr Val Ser Leu Gly Arg
130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
            260                 265                 270

Glu Tyr Lys Ile Arg Arg Glu Arg Asn Asn Ile Ala Val Arg Lys Ser
        275                 280                 285

Arg Asp Lys Ala Lys Met Arg Asn Leu Glu Thr Gln His Lys Val Leu
290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
            340                 345

<210> SEQ ID NO 33
<211> LENGTH: 1530
<212> TYPE: DNA
<213> ORGANISM: Homo sapiens

<400> SEQUENCE: 33
atgaatctcc tggacccctt catgaagatg accgacgagc aggagaaggg cctgtccggc      60
gcccccagcc ccaccatgtc cgaggactcc gcgggctcgc cctgcccgtc gggctccggc     120
tcggacaccg agaacacgcg gccccaggag aacacgttcc ccaagggcga gcccgatctg     180
aagaaggaga gcgaggagga caagttcccc gtgtgcatcc gcgaggcggt cagccaggtg     240
ctcaaaggct acgactggac gctggtgccc atgccggtgc cgtcaacgg ctccagcaag     300 aacaagccgc acgtcaagcg gcccatgaac gccttcatgg tgtgggcgca ggcggcgcgc     360
aggaagctcg cggaccagta cccgcacttg cacaacgccg agctcagcaa gacgctgggc     420
aagctctgga gacttctgaa cgagagcgag aagcggccct tcgtggagga ggcggagcgg     480
ctgcgcgtgc agcacaagaa ggaccacccg gattacaagt accagccgcg gcggaggaag     540
```

```
tcggtgaaga acgggcaggc ggaggcagag gaggccacgg agcagacgca catctccccc    600
aacgccatct tcaaggcgct gcaggccgac tcgccacact cctcctccgg catgagcgag    660
gtgcactccc ccggcgagca ctcggggcaa tcccagggcc accgacccc acccaccacc    720 cccaaaaccg acgtgcagcc gggcaaggct gacctgaagc gagaggggcg cccttgcca    780 gagggggca gacagccccc tatcgacttc cgcgacgtgg acatcggcga gctgagcagc    840
gacgtcatct ccaacatcga gaccttcgat gtcaacgagt tgaccagta cctgccgccc    900 aacggccacc cggggtgcc ggccacgcac ggccaggtca cctacacggg cagctacggc    960
atcagcagca ccgcggccac cccggcgagc gcgggccacg tgtggatgtc caagcagcag   1020
gcgccgccgc cacccccgca gcagccccca caggccccgc cggccccgca ggcgccccg    1080 cagccgcagg cggcgccccc acagcagccg gcggcacccc cgcagcagcc acaggcgcac   1140
acgctgacca cgctgagcag cgagccgggc cagtcccagc gaacgcacat caagacggag   1200
cagctgagcc ccagccacta cagcgagcag cagcagcact cgcccaaca gatcgcctac    1260 agccccttca acctcccaca ctacagcccc tcctacccgc ccatcacccg ctcacagtac   1320
gactacaccg accaccagaa ctccagctcc tactacagcc acgcggcagg ccagggcacc   1380
ggcctctact ccaccttcac ctacatgaac cccgctcagc gccccatgta cacccccatc   1440
gccgacacct ctggggtccc ttccatcccg cagacccaca gccccagca ctgggaacaa   1500 cccgtctaca cacagctcac tcgaccttga                                    1530
```

```
<210> SEQ ID NO 34
<211> LENGTH: 509
<212> TYPE: PRT
<213> ORGANISM: Homo sapiens

<400> SEQUENCE: 34

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190
```

-continued

```
Thr Glu Gln Thr His Ile Ser Pro Asn Ala Ile Phe Lys Ala Leu Gln
        195                 200                 205

Ala Asp Ser Pro His Ser Ser Gly Met Ser Glu Val His Ser Pro
    210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
            275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
            340                 345                 350

Pro Pro Ala Pro Gln Ala Pro Pro Gln Pro Gln Ala Ala Pro Pro Gln
            355                 360                 365

Gln Pro Ala Ala Pro Pro Gln Gln Pro Gln Ala His Thr Leu Thr Thr
    370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln Gln His Ser Pro Gln
                405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
            435                 440                 445

Ser Ser Tyr Tyr Ser His Ala Ala Gly Gln Gly Thr Gly Leu Tyr Ser
450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
            500                 505
```